United States Patent
Presley et al.

(10) Patent No.: US 11,148,115 B2
(45) Date of Patent: Oct. 19, 2021

(54) SULFURIC ACID ALKYLATION REACTOR SYSTEM AND CONVERSION OF A HYDROGEN FLUORIDE ALKYLATION UNIT TO A SULFURIC ACID ALKYLATION UNIT

(71) Applicant: Refining Technology Solutions, LLC, Overland Park, KS (US)

(72) Inventors: Christopher Shane Presley, Leawood, KS (US); Diwakar Rana, Overland Park, KS (US); Jason Brent Nunez, Lees Summit, MO (US); Arthur William Etchells, Philadelphia, PA (US); Ken Kranz, Wilmington, DE (US); Cody Jensen, Wilmington, DE (US)

(73) Assignee: Refining Technology Solutions, LLC, Overland Park, KS (US)

( * ) Notice: Subject to any disclaimer, the term of this patent is extended or adjusted under 35 U.S.C. 154(b) by 0 days.

(21) Appl. No.: 16/641,827

(22) PCT Filed: Aug. 30, 2018

(86) PCT No.: PCT/US2018/048810
§ 371 (c)(1),
(2) Date: Feb. 25, 2020

(87) PCT Pub. No.: WO2019/046558
PCT Pub. Date: Mar. 7, 2019

(65) Prior Publication Data
US 2021/0154640 A1    May 27, 2021

Related U.S. Application Data

(60) Provisional application No. 62/552,496, filed on Aug. 31, 2017.

(51) Int. Cl.
*B01J 19/00* (2006.01)
*B01J 19/24* (2006.01)
(Continued)

(52) U.S. Cl.
CPC ............. *B01J 14/00* (2013.01); *B01J 19/006* (2013.01); *B01J 19/0013* (2013.01); *B01J 19/24* (2013.01);
(Continued)

(58) Field of Classification Search
CPC ........ B01J 14/00; B01J 19/00; B01J 19/0006; B01J 19/0013; B01J 19/0053;
(Continued)

(56) References Cited

U.S. PATENT DOCUMENTS 2,311,144 A    2/1943    Wickham et al.
2,429,205 A    10/1947    Jenny et al.
(Continued)

FOREIGN PATENT DOCUMENTS

CN    104549087 A    4/2015
CN    104560143 A    4/2015
(Continued)

OTHER PUBLICATIONS

International Search Report, PCT/US2018/048810, dated Oct. 18, 2018, 3 pages.
(Continued)

*Primary Examiner* — Natasha E Young

(57) ABSTRACT

This disclosure relates to SA alkylation reactor systems. The reactor system involves a closed reactor vessel comprising a shell, a vapor outlet, and an emulsion outlet. The reactor system also involves a distributor located at the lower portion of the reactor vessel, a mixer fluidly connected with the distributor, and an emulsion pump fluidly connected with the mixer and the emulsion outlet, wherein the emulsion (Continued)

pump is located outside the reactor vessel. This disclosure also relates to a split SA alkylation reactor system wherein a single horizontal reactor vessel is divided to accommodate two reactor systems. This disclosure also relates to alkylation processes using the reactor systems. This disclosure also relates to methods of converting an HF alkylation unit to a SA alkylation unit. This disclosure also relates to converted SA alkylation units and alkylation processes performed in the converted SA alkylation units.

20 Claims, 20 Drawing Sheets

(51) Int. Cl.
  *B01J 14/00* (2006.01)
  *B01J 27/053* (2006.01)
  *B01J 27/12* (2006.01)
  *C07C 2/62* (2006.01)

(52) U.S. Cl.
  CPC ......... *B01J 19/2465* (2013.01); *B01J 27/053* (2013.01); *B01J 27/12* (2013.01); *C07C 2/62* (2013.01); *B01J 2219/0011* (2013.01); *B01J 2219/00024* (2013.01); *B01J 2219/00768* (2013.01); *C07C 2527/054* (2013.01)

(58) Field of Classification Search
  CPC ...... B01J 19/006; B01J 19/24; B01J 19/2455; B01J 19/2465; B01J 27/00; B01J 27/02; B01J 27/053; B01J 27/06; B01J 27/08; B01J 27/12; B01J 2219/00; B01J 2219/00002; B01J 2219/00018; B01J 2219/00024; B01J 2219/00049; B01J 2219/00051; B01J 2219/00074; B01J 2219/00105; B01J 2219/0011; B01J 2219/00761; B01J 2219/00763; B01J 2219/00765; B01J 2219/00768; C07C 2/00; C07C 2/54; C07C 2/56; C07C 2/58; C07C 2/62; C07C 2527/00; C07C 2527/02; C07C 2527/053; C07C 2527/054

See application file for complete search history.

(56) References Cited

U.S. PATENT DOCUMENTS

| | | | |
|---|---|---|---|
| 2,760,850 A | 8/1956 | Lambert et al. | |
| 2,828,348 A | 3/1958 | Stiles et al. | |
| 2,903,344 A * | 9/1959 | Rollman | B01J 19/1862 |
| | | | 422/605 |
| 3,759,318 A | 9/1973 | Putney et al. | |
| 4,018,846 A | 4/1977 | Mayer | |
| 4,225,740 A | 9/1980 | Chapman et al. | |
| 4,276,731 A | 7/1981 | Henggeler et al. | |
| 4,371,731 A | 2/1983 | Washer | |
| 4,383,977 A | 5/1983 | Hutson, Jr. et al. | |
| 4,404,418 A | 9/1983 | Hutson, Jr. et al. | |
| 4,467,131 A | 8/1984 | Washer et al. | |
| 4,513,165 A | 4/1985 | Van Pool | |
| 4,777,323 A | 10/1988 | Hann et al. | |
| 5,157,196 A | 10/1992 | Crossland et al. | |
| 5,284,990 A | 2/1994 | Peterson et al. | |
| 5,785,933 A * | 7/1998 | Cunningham | B01J 4/004 |
| | | | 422/215 |
| 5,841,014 A | 11/1998 | Graves et al. | |
| 6,194,625 B1 | 2/2001 | Graves et al. | |
| 7,285,698 B2 | 10/2007 | Liu et al. | |
| 7,850,929 B2 | 12/2010 | Smith, Jr. et al. | |
| 8,034,988 B2 | 10/2011 | Loescher et al. | |
| 9,580,366 B2 | 2/2017 | Puett et al. | |
| 2014/0128654 A1* | 5/2014 | Fang | B01J 14/00 |
| | | | 585/730 |

FOREIGN PATENT DOCUMENTS

| | | |
|---|---|---|
| CN | 105018134 B | 6/2017 |
| WO | 9948845 A1 | 9/1999 |
| WO | 2011015662 A2 | 2/2011 |

OTHER PUBLICATIONS

Written Opinion, PCT/US2018/048810, dated Oct. 18, 2018, 5 pages.
International Preliminary Report on Patentability, PCT/US2018/048810, dated Mar. 3, 2020, 6 pages.
"Catalytic Alkylation", Petro/Chem Engineer, Dec. 1961 and Jan. 1962.
"Alkylation will be key process in reformulated gasoline era", Oil & Gas Journal, Nov. 12, 1990, pp. 79-92.
"H2SO4, HF processes compared, and new technologies revealed", Oil & Gas Journal, Nov. 26, 1990, pp. 70-77.
"Which alkylation—HF or H2SO4?", Hydrocarbon Processing, Sep. 1985.
Cross, W. et al., "Safer with Sulfur", Hydrocarbon Engineering, Sep. 2010.
Peterson, J.R. et al., "STRATCO's ConvEx(TM) Process: Low Cost Conversion/Expansion from HF to H2SO4 Alkylation", presented at 1994 NPRA Annual Meeting, AM-94-17, San Antonio, TX, Mar. 1994.

* cited by examiner

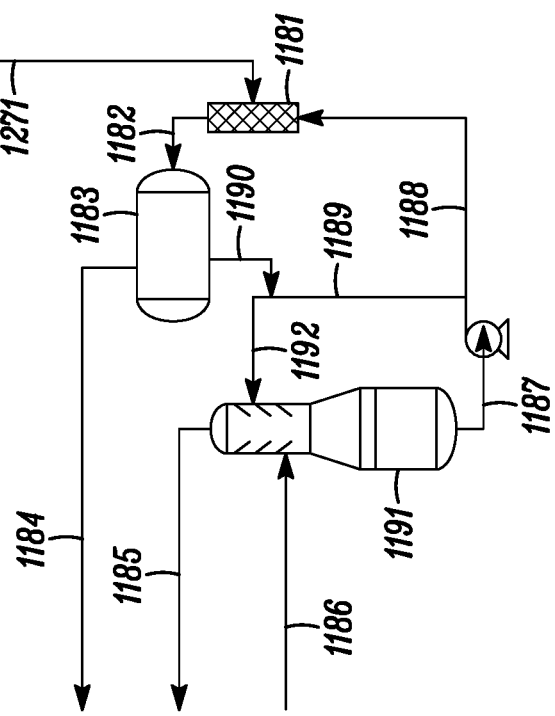
FIG. 12 (Prior Art) Cont.

ced alkylation unit. Most alkylate is produced in refineries by combining

SULFURIC ACID ALKYLATION REACTOR SYSTEM AND CONVERSION OF A HYDROGEN FLUORIDE ALKYLATION UNIT TO A SULFURIC ACID ALKYLATION UNIT

CROSS-REFERENCE TO RELATED APPLICATION

This application is a national stage application claiming priority to PCT/US2018/048810, now WO 2019/046558, filed on Aug. 30, 2018, which claims priority of U.S. Patent Application 62/552,496 filed on Aug. 31, 2017, the disclosure of which is incorporated herein by reference in its entirety for all purposes.

BACKGROUND

Field of the Disclosure

The present disclosure relates to a sulfuric acid alkylation reactor system and method of use, for example, in an alkylation process. The present disclosure also relates to methods for conversion of a hydrogen fluoride (HF) catalyzed alkylation unit to a sulfuric acid (SA) catalyzed alkylation unit. The present disclosure also relates to apparatus and systems for use in SA catalyzed alkylation units which are newly added or retained from an existing HF catalyzed alkylation unit.

Description of Related Art

Because of its clean-fuel properties (iso-paraffinic, high-octane, low-vapor pressure and very low sulfur), alkylate is considered one of the most desired components in the gasoline pool. As mandates for cleaner-burning fuel in the US and abroad have started to become fully realized, refiners are relying more than ever on alkylate to meet stringent gasoline specifications. With increasing pressure to reduce tailpipe emissions, the rapid decline of diesel in Europe and the modernization of automobiles worldwide, alkylate is well-positioned to be in steady demand for decades to come.

Most alkylate is produced in refineries by combining $C_3$-$C_5$ light olefins from the fluid catalytic cracker (FCC) with isobutane in a process called alkylation. In an alkylation process, the $C_3$-$C_5$ light olefins react with isobutane in the presence of an acid catalyst such as sulfuric acid to form desired alkylation products. In order to maximize the reaction efficiency, an alkylation reactor is typically designed to cause intimate contact between the reactants and the catalyst. Various sulfuric acid alkylation reactors have been disclosed. For example, U.S. Pat. Nos. 3,759,318 and 9,580,366 described a horizontal reactor such as a DuPont STRATCO® Contactor™ reactor. U.S. Pat. No. 7,850,929 described a vertical sulfuric acid alkylation reactor.

Predominant alkylation technologies utilized by refiners require either sulfuric acid ($H_2SO_4$, SA) or hydrofluoric acid (HF) to catalyze the reaction. Although grassroots construction of sulfuric acid alkylation units has dominated the industry for the last 20 years, a very large number of HF alkylation units remain in operation. For example, in the US, approximately 100 alkylation units are in operation, with about half of them utilizing HF alkylation technology. Due to the volatile and toxic nature of HF, refiners have long sought out cost-effective solutions to convert HF alkylation units to safer sulfuric acid alkylation technology. However, with the perceived high cost of conversion and a lack of a regulatory requirement to make this change, refiners have yet to convert an HF alkylation unit to a sulfuric acid alkylation unit.

Whether involving an expansion of existing alkylation units, refinery grassroots alkylation units or stand-alone alkylation complexes utilizing feedstocks from nontraditional petrochemical sources, alkylation projects are of high interest in the energy sector. For refiners that operate HF alkylation units, the regulatory and community pressures to eliminate the use of HF have never been greater. This is especially a concern in those refineries operating near large metropolitan areas. Therefore, there is a need for cost-effective methods to convert existing HF catalyzed alkylation units to sulfuric acid (SA) catalyzed alkylation units.

BRIEF SUMMARY OF THE DISCLOSURE

The present disclosure provides a sulfuric acid alkylation reactor system. The reactor system comprises: (a) a closed reactor vessel comprising a shell, a vapor outlet, and an emulsion outlet; (b) a distributor located at the lower portion of the reactor vessel; (c) a mixer fluidly connected with the distributor; and (d) an emulsion pump fluidly connected with the mixer and the emulsion outlet; wherein the emulsion pump is located outside the reactor vessel.

The present disclosure also provides a split sulfuric acid alkylation reactor system. The reactor system comprises: (a) a closed horizontal reactor vessel comprising a shell, a vapor outlet, a first emulsion outlet, a second emulsion outlet, a first partition baffle, a first coalescing media, a second partition baffle, a second coalescing media, a spent acid outlet, and a net effluent outlet; (b) a first distributor located at the lower portion of the reactor vessel; (c) a second distributor located at the lower portion of the reactor vessel; (d) a first mixer fluidly connected with the first distributor; (e) a second mixer fluidly connected with the second distributor; (f) a first emulsion pump fluidly connected with the first mixer, the first emulsion outlet, and the spent acid outlet; and (g) a second emulsion pump fluidly connected with the second mixer, the second emulsion outlet, and the spent acid outlet; wherein the first partition baffle, the second partition baffle, the first coalescing media, and the second coalescing media extend upwardly from the bottom of the reactor vessel respectively, the first coalescing media is downstream of the first partition baffle, the second coalescing media is downstream of the second partition baffle, the first coalescing media and the second coalescing media define a first reaction zone, a second reaction zone and an acid settling zone inside the reactor vessel, the first reaction zone is upstream of the first coalescing media, the second reaction zone is upstream of the second coalescing media, the acid settling zone is between the first coalescing media and the second coalescing media, the first distributor is located at the first reaction zone, the second distributor is located at the second reaction zone, the first emulsion pump and the second emulsion pump are located outside the reactor vessel.

The present disclosure also provides an alkylation process comprising contacting an olefin with an isoparaffin in the presence of a sulfuric acid catalyst to produce a product mixture comprising an alkylate wherein the contacting is performed in a sulfuric acid alkylation reactor system or a split sulfuric acid alkylation reactor system as disclosed in this disclosure.

The present disclosure also provides a method for converting a hydrogen fluoride alkylation unit which utilizes hydrogen fluoride as a reaction catalyst to a sulfuric acid alkylation unit, the method comprising: (a) substituting sulfuric acid for hydrogen fluoride as the reaction catalyst; and (b) modifying a suitable vessel in the hydrogen fluoride alkylation unit to provide a sulfuric acid alkylation reactor system or a split sulfuric acid alkylation reactor system as disclosed in this disclosure, wherein the suitable vessel is retained as the reactor vessel in the sulfuric acid alkylation reactor system or the split sulfuric acid alkylation reactor system.

The present disclosure also provides a method for converting a hydrogen fluoride alkylation unit which utilizes hydrogen fluoride as a reaction catalyst to a sulfuric acid alkylation unit, the method comprising: (a) substituting sulfuric acid for hydrogen fluoride as the reaction catalyst; and (b) providing a sulfuric acid alkylation reactor system or a split sulfuric acid alkylation reactor system as disclosed in this disclosure, wherein a new vessel is provided as the reactor vessel in the sulfuric acid alkylation reactor system or the split sulfuric acid alkylation reactor system.

The present disclosure also provides a converted sulfuric acid alkylation unit comprising a sulfuric acid alkylation reactor system or a split sulfuric acid alkylation reactor system as disclosed in this disclosure.

The present disclosure further provides an alkylation process performed in a converted sulfuric acid alkylation unit as disclosed in this disclosure.

BRIEF DESCRIPTION OF THE FIGURES

Embodiments are illustrated in the accompanying figures to improve understanding of concepts as presented herein.

Figure 1:
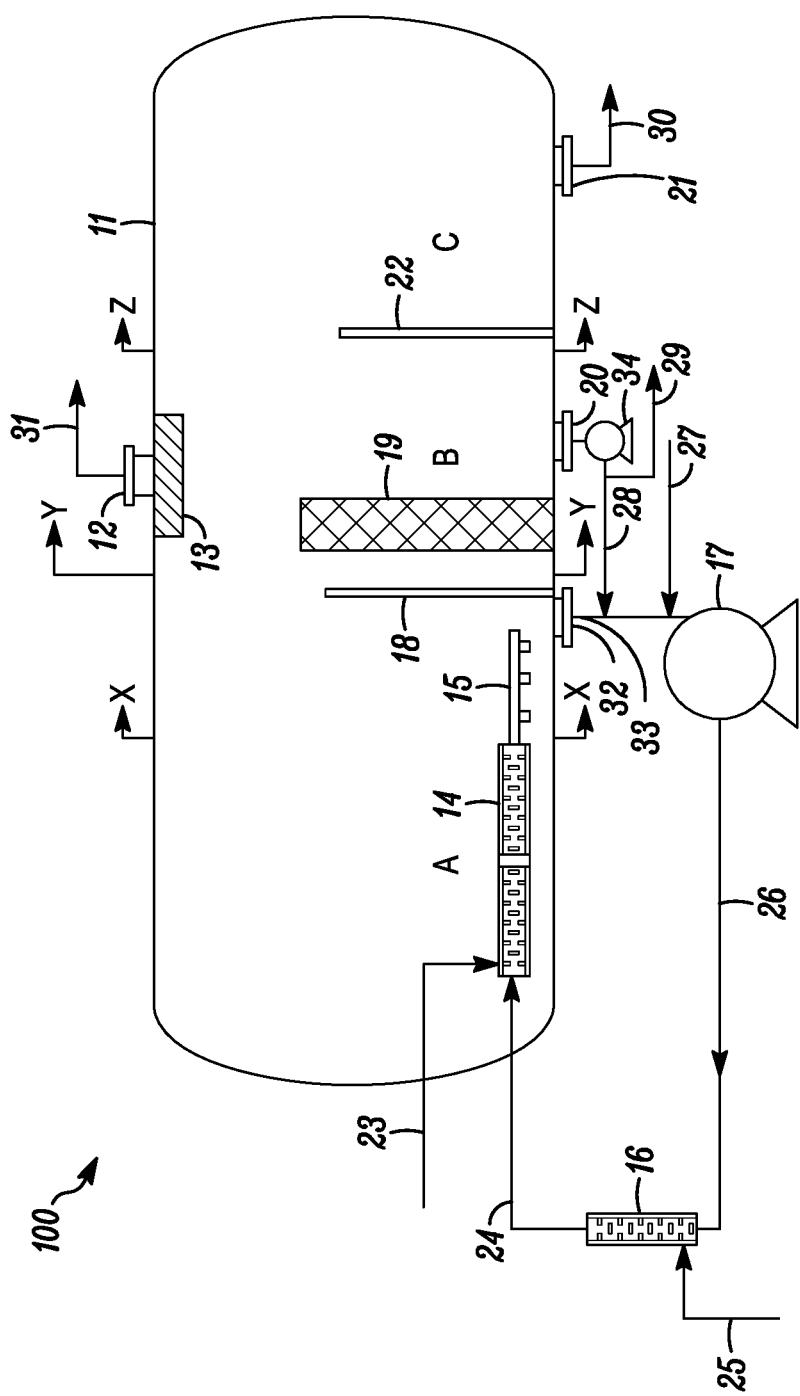
FIG. 1 is a schematic illustration of a sulfuric acid alkylation reactor system with a closed horizontal reactor vessel.

Corresponding reference characters indicate corresponding parts throughout the drawings. Skilled artisans appreciate that objects in the figures are illustrated for simplicity and clarity and have not necessarily been drawn to scale. For example, the dimensions of some of the objects in the figures may be exaggerated relative to other objects to help to improve understanding of embodiments. Certain detailed features, such as pumps, heat exchangers or other ancillary equipment are not shown for the sake of simplicity and in order to demonstrate the main features of the alkylation unit or process.

DETAILED DESCRIPTION

The foregoing general description and the following detailed description are exemplary and explanatory only and are not restrictive of the invention, as defined in the appended claims. Other features and benefits of any one or more of the embodiments will be apparent from the following detailed description, and from the claims.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Also, use of "a" or "an" are employed to describe elements and components described herein. This is done merely for convenience and to give a general sense of the scope of the invention. This description should be read to include one or at least one and the singular also includes the plural unless it is obvious that it is meant otherwise.

Unless otherwise defined, all technical and scientific terms used herein have the same meaning as commonly understood by one of ordinary skill in the art to which this invention belongs. In case of conflict, the present specification, including definitions, will control. Although methods and materials similar or equivalent to those described herein can be used in the practice or testing of embodiments of the present invention, suitable methods and materials are described below. In addition, the materials, methods, and examples are illustrative only and not intended to be limiting.

When an amount, concentration, or other value or parameter is given as a range, preferred range or a list of upper preferable values and/or lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range.

Before addressing details of embodiments described below, some terms are defined or clarified.

The terms "retaining" or "retained", when used together with an equipment or a vessel in this disclosure, means the equipment or the vessel in an existing HF alkylation unit is kept, utilized or modified to become an equipment or a vessel in the converted SA alkylation unit. The equipment or the vessel from the existing HF alkylation unit can be used as it is or modified to fit in the converted SA alkylation unit. In some embodiments, the equipment or the vessel in the existing HF alkylation unit can be reused, modified or retrofitted to become the same kind of equipment or vessel in the converted SA alkylation unit. In some embodiments, the equipment or the vessel in the existing HF alkylation unit can be repurposed or modified to become a different kind of equipment or vessel in the converted SA alkylation unit.

The terms "decommissioning" or "decommissioned", when used together with an equipment or a vessel in this disclosure, means the equipment or the vessel in an existing HF alkylation unit is abandoned or no longer used in the converted SA alkylation unit during an alkylation process. The equipment or the vessel can remain in or be moved away from the site of the converted SA alkylation unit.

The term "new", when used together with an equipment or a vessel in this disclosure, means the equipment or the vessel added or provided to the converted SA alkylation unit is not previously present in the existing HF alkylation unit.

The term "converted SA alkylation unit(s)", as used herein, means a SA catalyzed alkylation unit provided by converting a HF catalyzed alkylation unit.

The term "remote HF storage tank", as used herein, means an HF storage tank located outside the battery limits of an HF alkylation unit.

The term "remote HF blowdown drum", as used herein, means an HF blowdown drum located outside the battery limits of an HF alkylation unit.

The term "sulfuric acid alkylation reactor systems disposed in sequence", as used herein, means that the spent acid solution from at least one non-final alkylation reactor system is sent to the immediately subsequent alkylation reactor system as part or all of the sulfuric acid solution therein, that is, spent acid solution from a non-final alkylation reactor system can be reused as catalyst in the immediately subsequent alkylation reactor system. A portion of the spent acid solution from the final alkylation reactor system can be recycled to the final alkylation reactor system, and the rest is purged, that is, the spent acid solution from the final alkylation reactor system is not reused in another alkylation reactor system. In some embodiments, the spent acid solution from each non-final alkylation reactor system is sent to the immediately subsequent alkylation reactor system as part or all of the sulfuric acid solution therein. Fresh sulfuric acid is fed into the first alkylation reactor system. In some embodiments, fresh sulfuric acid can also be fed into other non-final alkylation reactor system. Fresh sulfuric acid is typically not fed into the final alkylation reactor system.

The terms "reactor system(s)", "alkylation reactor system(s)" and "sulfuric acid alkylation reactor system(s)" can be used interchangeably. They include both SA alkylation reactor system and split SA alkylation reactor system.

The term "olefin", as used herein, means an unsaturated hydrocarbon comprising one or more carbon-carbon double bonds. The unsaturated hydrocarbon herein does not include aromatic compounds. In some embodiments, the olefin has a single carbon-carbon double bond. In some embodiments, the olefin is a $C_3$ to $C_5$ olefin selected from the group consisting of propene, butenes, pentenes, and combinations thereof. In some embodiments, the olefin comprises propene. In some embodiments, the olefin comprises a butene selected from the group consisting of 1-butene, 2-butene, isobutene, and combinations thereof. 2-butene includes cis-2-butene and trans-2-butene. In some embodiments, the olefin comprises a pentene selected from the group consisting of 1-pentene and its branched isomers, 2-pentene and its branched isomers, and combinations thereof. 2-pentene includes cis-2-pentene and trans-2-pentene. In some embodiments, the olefin comprises a mixture of propene, butene and pentene.

The term "isoparaffin", as used herein, means isobutane, isopentane, or their mixtures. In some embodiments, the isoparaffin comprises, consists essentially of, or consists of an isobutane. In some embodiments, the isoparaffin comprises a mixture of isobutane and isopentane. In some embodiments, the isoparaffin is isobutane.

The term "recycled isoparaffin", as used herein, means the unreacted isoparaffin contained in the net effluent which is separated and recovered from the net effluent and recycled to the alkylation reactor. In some embodiments, the recycled isoparaffin is recovered as an isoparaffin fraction generated in a fractionator. In some embodiments, the recycled isoparaffin is a recycled isobutane.

The term "makeup isoparaffin", as used herein, means isoparaffin fed to the alkylation reactor system or alkylation unit to replenish the isoparaffin consumed during the alkylation reaction. In some embodiments, the makeup isoparaffin is a makeup isobutane.

The term "spent acid", as used herein, means the sulfuric acid phase of the alkylate product mixture generated at the end of the alkylation reaction. Typically, the spent acid comprises sulfuric acid, water, acid soluble oils, and reaction intermediates such as sulfate esters.

The term "fresh acid", as used herein, means a sulfuric acid solution which has not been used as the catalyst in an alkylation reaction. The fresh acid solution is essentially free of acid soluble oils and alkylation intermediates such as sulfate esters. In some embodiments, the acid strength of the fresh acid is in the range of from about 96.5 wt % to about 99.5 wt %.

The term "net effluent", as used herein, means the liquid hydrocarbon phase of the alkylate product mixture generated at the end of the alkylation reaction in a SA alkylation reactor system or a split SA alkylation reactor system. The net effluent typically comprises unreacted isoparaffin (e.g., isobutane), alkylate, and sulfur-containing contaminants such as residual sulfuric acid, alkyl sulfates, etc. In some embodiments, the net effluent further comprises propane and/or n-butane. The net effluent can be purified and fractionated to produce an alkylate product.

The term "alkylate", as used herein, means the reaction products generated in alkylation reactions between an olefin and an isoparaffin in the presence of a sulfuric acid catalyst or an HF catalyst. Alkylates typically are highly branched paraffinic hydrocarbons. Refiners use alkylate as a gasoline blend stock to boost octane, reduce Reid vapor pressure ("RVP"), and reduce olefin content in the final gasoline blend.

The term "acid strength", as used herein, means the concentration of the sulfuric acid solution which is expressed in weight percent $H_2SO_4$ as determined by titration with standardized sodium hydroxide. Diluents that can reduce the acid strength of a sulfuric acid solution include water, acid soluble oils formed by side reactions during an alkylation process, and reaction intermediates such as sulfate esters formed during an alkylation reaction.

The term "capacity", when used in connection with an alkylation unit, means the amount of alkylate the alkylation unit can produce per day.

The term, "directly connected", as used herein, means that two devices are directly fluidly connected without an intermediate device in between such as a cooling or heating device (e.g., a heat exchanger), a purification or treatment device, a separation device (e.g., a liquid/vapor separator), a mixer, or a storage vessel. In some embodiments, the two devices can be directly connected with a conduit.

The terms "upstream", "downstream", "sequence", etc., as used herein, are all defined with respect to the flow direction of the process liquid. Depending on the process steps, the process liquid can be hydrocarbon, sulfuric acid, or their mixture (e.g., emulsion or alkylate product mixture).

In this disclosure, the distributor is inside the reactor vessel. The term "distributor", as used herein, means a perforated device located at the lower portion of the reactor vessel, that is, the distributor is below the liquid level (i.e., liquid surface) in the reactor vessel during an alkylation process using the reactor system. The distributor has a plurality of perforations on it. In alkylation process, the sulfuric acid/hydrocarbon emulsion generated in the mixer (e.g., internal static mixer, external static mixer, and/or homogenizer) flows into the distributor and is injected into the reactor vessel through the perforations in the form of a plurality of jets. In some embodiments, the distributor is a relatively elongated device. In some embodiments, the distributor is a pipe. In some embodiments, the distributor is a perforated substantially cylindrical pipe with a plurality of perforations on it. The perforations can be holes or nozzles. In some embodiments, the perforations face down. In some embodiments, the perforated substantially cylindrical pipe has one open end and one closed end. In some embodiments, the closed end can have one or more perforations on it. The open end can be directly connected with a mixer (e.g., internal static mixer or homogenizer). In some embodiments, the open end is mounted directly on the outlet end of the internal static mixer. In some embodiments, the distributor is empty inside, that is, the distributor has no internal structure, packing or components inside. In some embodiments, the distributor extends substantially along the bottom interior surface of the reactor vessel. In some embodiments, the distributor is substantially horizontal. In some embodiments, the distributor is substantially less than about 8 inches, or less than about 5 inches, or less than about 4 inches, or less than about 3 inches, or less than about 2 inches, or less than about 1 inch from the bottom interior surface of the reactor vessel.

The perforations on distributor can have any shapes. For example, the perforations can be round, oval, square or rectangular. In some embodiments, the perforations are substantially oval. In some embodiments, the perforations have open area in the range of from about 0.049 square inches to about 1.77 square inches, or from about 0.2 square inches to about 0.79 square inches, or from about 0.28 square inches to about 0.64 square inches. In some embodiments, the perforations are substantially round, and the diameter of the perforations is in the range of from about 0.25 inch to about 1.50 inch, or from about 0.5 inch to about 1.0 inch, or from about 0.6 inch to about 0.9 inch. In some embodiments, perforations on same distributor have substantially same shape and substantially same open area. The pressure inside the distributor is higher than the pressure outside the distributor. In some embodiments, the pressure difference across the perforations of the distributor is in the range of from about 5 psi (pound per square inch) to about 75 psi, or from about 5 psi to about 50 psi, or from about 5 psi to about 35 psi, or from about 5 psi to about 20 psi, or from about 10 psi to about 20 psi.

In some embodiments, the distributor is directly connected with or extends from an internal static mixer. In some embodiments, the length of the internal static mixer ranges from about 5% to about 50% of the total length of the distributor and the internal static mixer. In some embodiments, the length of the internal static mixer ranges from about 10% to about 30% of the total length of the distributor and the internal static mixer. In some embodiments, the length of the internal static mixer ranges from about 15% to about 25% of the total length of the distributor and the internal static mixer.

The term "horizontal reactor" or "horizontal reactor vessel", as used herein, means a reactor vessel having a longitudinal axis which is substantially horizontal.

The term "vertical reactor" or "vertical reactor vessel", as used herein, means a reactor vessel having a longitudinal axis which is substantially vertical.

The term "static mixer", as used herein, means a device for the continuous mixing of hydrocarbon with sulfuric acid to form an emulsion without moving components inside.

The term "internal static mixer", as used herein, means a static mixer located inside the reactor vessel. The internal static mixer comprises essentially no coalescing media or coalescing fiber. In some embodiments, the internal static mixer extends substantially along the bottom interior surface of the reactor vessel. In some embodiments, the internal static mixer is substantially horizontal. In some embodiments, the internal static mixer is at substantially the same elevation as the distributor.

The term "external static mixer", as used herein, means a static mixer located outside the reactor vessel. The external static mixer comprises essentially no coalescing media or coalescing fiber. In some embodiments, the external static mixer is directly connected with the emulsion pump, and the emulsion pump is fluidly connected with the spent acid outlet, the emulsion outlet and a fresh acid source. In such embodiments, the external static mixer is also fluidly connected with the refrigeration section of the sulfuric acid alkylation unit to receive a refrigerant recycle stream comprising isoparaffin (e.g., isobutane) so that the refrigerant recycle stream is mixed with the emulsion/spent acid/fresh acid mixture from the emulsion pump to generate an emulsion with higher isoparaffin content and lower temperature before being introduced into the reactor vessel.

The term "homogenizer", as used herein, means a mechanical device with moving component(s) that can effectively mix hydrocarbon with sulfuric acid to form an emulsion. In some embodiments, the homogenizer comprises an electric motor. In some embodiments, the homogenizer is a rotor stator mixer.

The term "rotor stator mixer", as used herein, means a high-shear mixer that comprises one or more generator comprising a rotor/stator combination. There is a gap between rotor and stator which forms the high-shear zone for fluids to be mixed. The rotor stator mixer has an inlet and an outlet for the fluids to go through and get mixed.

The term "raised sump", as used herein, means a tank or a container inside the reactor vessel for collecting the liquid hydrocarbon phase formed or separated out in the acid settling zone. In some embodiments, the raised sump is located at the acid settling zone. The raised sump typically has an open top and an outlet. The top is below the liquid hydrocarbon phase level in the acid settling zone so that the liquid hydrocarbon phase can flow over the top to enter the raised sump. The top is above the sulfuric acid phase level in the acid settling zone. In some embodiments, the top is no more than 4 inches, or no more than 3 inches, or no more than 2 inches, or no more than 1 inch, or no more than 0.5 inch below the liquid hydrocarbon phase level in the acid settling zone. In some embodiments, the outlet of the raised sump is the net effluent outlet. In some embodiments, the outlet of the raised sump is directly connected with the net effluent outlet by a conduit (e.g., a pipe). In some embodiments, the outlet is at the lower end or the bottom of the raised sump.

The raised sump can be fixed or secured in the reactor vessel in various ways. In some embodiments, the raised sump can be fixed with supporting bars or beams welded to an interior wall of the reactor vessel. By "interior wall of the reactor vessel", it is meant herein the interior wall of the shell. In some embodiments, the raised sump can be welded to the interior wall of the reactor vessel. In some embodiments, the raised sump can be sealingly attached to an interior wall of the reactor vessel, and such interior wall can serve as part of the interior wall of the raised sump. In some embodiments, the bottom of the raised sump is the bottom of the reactor vessel, and the raised sump has enclosed vertical wall(s) extending upwardly from the bottom of the reactor vessel. Such raised sump can have the shape of a standing pipe, and its outlet can be at the bottom of the raised sump as the net effluent outlet.

The term "wt %", as used herein, means percentage by weight.

Alkylation processes in general are well known to those of skill in the art. For example, see "Catalytic Alkylation", Petri/Chem Engineer, December 1961 and January 1962, "Alkylation will be key process in reformulated gasoline era", Oil & Gas Journal, Nov. 12, 1990, pp. 79-92, "$H_2SO_4$, HF processes compared, and new technologies revealed", Oil & Gas Journal, Nov. 26, 1990, pp. 70-77, and "Which alkylation—HF or $H_2SO_4$?", Hydrocarbon Processing, September 1985, all herein incorporated by reference in its entirety for all purposes. Additionally, alkylation is generally disclosed in U.S. Pat. Nos. 4,018,846; 4,225,740; 4,276,731; 4,371,731; 4,383, 977; 4,404,418; 4,467,131; 4,513,165; 4,777,323; and 5,157,196; all herein also incorporated by reference in its entirety for all purposes.

Most conventional alkylation reactors use stirrers or impellers to generate emulsion. Such stirrers or impellers are typically driven by motors. The present disclosure provides a sulfuric acid alkylation reactor system wherein there is no stirrer or impeller inside the reactor vessel to create and maintain an emulsion. In some embodiments, there is no moving parts inside the reactor vessel to create and maintain an emulsion.

The present disclosure provides a sulfuric acid (SA) alkylation reactor system for alkylating at least one isoparaffin reactant with at least one olefin reactant, in the presence of sulfuric acid catalyst, to produce alkylate products. The reactor system comprises: (a) a closed reactor vessel comprising a shell, a vapor outlet, and an emulsion outlet; (b) a distributor located at the lower portion of the reactor vessel; (c) a mixer fluidly connected with the distributor; and (d) an emulsion pump fluidly connected with the mixer and the emulsion outlet; wherein the emulsion pump is located outside the reactor vessel. In some embodiments, the reactor vessel may comprise two or more emulsion outlets for emulsion recycle, and the emulsion pump is fluidly connected with each of them. In some embodiments, the emulsion pump is also fluidly connected with a fresh acid source. In some embodiments, the emulsion pump is fluidly connected with a fresh acid feed pipe. In some embodiments, the mixer is an internal static mixer, an external static mixer, or a homogenizer directly connected with the distributor. In some embodiments, when the mixer is an external static mixer, the distance between the mixer and the distributor is no more than 30 feet, or no more than 10 feet, or no more than 5 feet, or no more than 3 feet, or no more than 2 feet, or no more than 1 feet.

In some embodiments, the sulfuric acid alkylation reactor system or the split sulfuric acid alkylation reactor system is part of a sulfuric acid alkylation unit which also comprises a refrigeration section, a fractionation section, and a net effluent treatment section. The refrigeration section helps to keep the reaction temperature low in the reactor system by sending a refrigerant recycle stream comprising isoparaffin reactant back to the reactor system. The fractionation section recovers and recycles unreacted isoparaffin reactant to the reactor system. The net effluent treatment section purifies the net effluent stream generated in the reactor system. In some embodiments, the sulfuric acid alkylation unit also comprises an acid blowdown section which is used to remove and/or recover residual hydrocarbons from the spent acid before sending the spent acid to storage.

In this disclosure, the reactor vessel is closed, that is, there is no mass (e.g., reactants and products) transfer in or out of the reactor vessel except through specified inlets or outlets or through specified conduits connecting inside and outside of the reactor vessel. The pressure inside the reactor vessel is higher than the atmospheric pressure outside the reactor vessel. In some embodiments, the reactor vessel is substantially cylindrical. In some embodiments, the reactor vessel is a horizontal reactor vessel. In some embodiments, the reactor vessel is a relatively elongated horizontal cylindrical reactor vessel. In some embodiments, the reactor vessel is a vertical reactor vessel.

The closed reactor vessel comprises a shell having a wall which is closed and encloses the shell space. The closed reactor vessel also comprises a vapor outlet. In some embodiments, the vapor outlet is at the upper portion of the reactor vessel, that is, the vapor outlet is above the liquid level (i.e., liquid surface) in the reactor vessel during an alkylation process using the reactor system. In some embodiments, the vapor outlet is at the upper end of the reactor vessel. The closed reactor vessel has a top and a bottom. In some embodiments, the vapor outlet is at the top of the reactor vessel. The vapor exiting the vapor outlet comprises light hydrocarbon which comprises unreacted isoparaffin such as isobutane. In some embodiments, the vapor outlet is fluidly connected with the refrigeration section of the sulfuric acid alkylation unit. In some embodiments, the vapor outlet is fluidly connected with a refrigerant compressor. In some embodiments, the vapor outlet is fluidly connected with a refrigerant compressor which is fluidly connected with a refrigerant condenser. In some embodiments, the vapor outlet is fluidly connected with a compressor K/O (knockout) drum upstream of the refrigerant compressor with respect to the flow direction of the vapor stream. In some embodiments, the vapor outlet is directly connected with the compressor K/O drum. In some embodiments, there is no compressor K/O drum in the refrigeration section, and the vapor outlet is directly connected with the refrigerant compressor. In some embodiments, the vapor outlet is equipped with a demister to remove suspended liquid droplets entrained in the vapor stream. In some embodiments, the demister comprises, consists essentially of, or consists of a mesh pad comprising a coalescing media.

The refrigeration section typically comprises a refrigerant compressor and a refrigerant condenser downstream of the refrigerant compressor with respect to the flow direction of the vapor stream. In some embodiments, the refrigeration section further comprises a compressor K/O drum upstream of the refrigerant compressor to remove suspended liquid droplets entrained in a vapor stream before the vapor stream is introduced into the refrigerant compressor. Vapors evaporated in the reactor vessel leave the reactor vessel through the vapor outlet and are sent to the refrigerant compressor where the vapors are compressed. The compressed vapor is then cooled and condensed in the refrigerant condenser to form a refrigerant recycle stream which is sent back to the reactor vessel.

In some embodiments, the mixer is an internal static mixer inside the reactor vessel. In some embodiments, the reactor system comprises: (a) a closed reactor vessel comprising a shell, a vapor outlet, and an emulsion outlet; (b) an internal static mixer; (c) a distributor directly connected with the internal static mixer; and (d) an emulsion pump fluidly connected with the internal static mixer and the emulsion outlet; wherein the emulsion pump is located outside the reactor vessel, and the distributor is located at the lower portion of the reactor vessel. In some embodiments, the reactor system comprises no homogenizer. In some embodiments, the reactor system comprises no rotor stator mixer. In some embodiments, the internal static mixer is located at the lower portion of the reactor vessel. The distributor is downstream of the internal static mixer. In some embodiments, the distributor extends from the internal static mixer.

In some embodiments, the sulfuric acid alkylation reactor system further comprises an external static mixer located outside the reactor vessel. The internal static mixer and the external static mixer can independently comprise, consist essentially of, or consist of one or more static mixers. When the internal static mixer or the external static mixer comprises, consists essentially of, or consists of two or more static mixers, the two or more static mixers are disposed in sequence and directly connected with each other in a head-to-tail fashion. In this disclosure, when an internal static mixer or an external static mixer consists of two or more static mixers disposed in sequence and directly connected with each other in a head-to-tail fashion, such internal static mixer or external static mixer is deemed as a single one internal static mixer or a single one external static mixer respectively. The internal static mixer and the external static mixer each independently has an inlet and an outlet. The inlet end of the internal static mixer or the external static mixer is the inlet end of the first static mixer in the sequence, and the outlet end of the internal static mixer or the external static mixer is the outlet end of the final static mixer in the sequence. In some embodiments, the one or more static mixers are cylindrical or generally cylindrical tubes having non-moving mixing elements fixed inside the tube. In some embodiments, such non-moving mixing elements can be a series of baffles such as twists of metal, corrugated sheets, or tabs sticking out from the interior wall of the tube.

The static mixers are used herein to facilitate the intimate contact between hydrocarbon reactants and sulfuric acid catalysts. In some embodiments, both the internal static mixer and the distributor are located at the lower portion of the reactor vessel, that is, the internal static mixer and the distributor are below the liquid level in the reactor vessel during an alkylation process using the reactor system. The internal static mixer and the distributor are submerged by the sulfuric acid/hydrocarbon emulsion in the reactor so that heat generated from the alkylation reactions inside the internal static mixer and the distributor can be dissipated.

In some embodiments, there is no external static mixer in the reactor system, the internal static mixer is directly connected with the emulsion pump, and a refrigerant recycle stream from the refrigeration section is introduced into the connecting conduit between the internal static mixer and the emulsion pump. In some embodiments, the internal static mixer is fluidly connected with a refrigerant recycle pump in the refrigeration section.

In some embodiments, the reactor system further comprises an external static mixer fluidly connected with the internal static mixer and the emulsion pump. In some embodiments, the reactor system comprises: (a) a closed reactor vessel comprising a shell, a vapor outlet, and an emulsion outlet; (b) an internal static mixer located at the lower portion of the reactor vessel; (c) a distributor directly connected with the internal static mixer; (d) an external static mixer fluidly connected with the internal static mixer; and (e) an emulsion pump fluidly connected with the emulsion outlet and the external static mixer; wherein the emulsion pump is located outside the reactor vessel. In some embodiments, the reactor system comprises no homogenizer. In some embodiments, the reactor system comprises no rotor stator mixer. In some embodiments, the distributor extends from the internal static mixer.

In some embodiments, the external static mixer is directly connected with the internal static mixer. In some embodiments, the external static mixer is directly connected with the emulsion pump. In some embodiments, the outlet end of the external static mixer is directly connected with the inlet end of the internal static mixer. In some embodiments, the external static mixer is fluidly connected with the internal static mixer through a connecting conduit sealingly extending through the wall of the shell. In some embodiments, the inlet end of the external static mixer is directly connected with the emulsion pump.

The olefin and isoparaffin reactants, including recycled isoparaffin and makeup isoparaffin, as well as refrigerant recycle stream, can be fed into the reactor system or the reactor vessel in various ways. In some embodiments, the olefin, makeup isoparaffin and recycled isoparaffin can be fed into the inlet end of the internal static mixer separately or as a mixture of any two or three of them. In some embodiments, the refrigerant recycle stream can be fed into the inlet end of the external static mixer. In some embodiments, olefin, makeup isoparaffin and/or recycled isoparaffin can be fed into the inlet end of the external static mixer or fed into a conduit upstream of and directly connected with the external static mixer. In some embodiments, olefin, makeup isoparaffin, recycled isoparaffin and/or refrigerant recycle stream can be fed to the emulsion pump or fed into a conduit upstream of and directly connected with the emulsion pump. In some embodiments, the emulsion pump is also fluidly connected with an olefin feed conduit, a conduit for recycling isoparaffin, a conduit for feeding makeup isoparaffin, and/or a conduit for transporting refrigerant recycle stream from the refrigeration section, all upstream of the emulsion pump.

In some embodiments, the internal static mixer is fluidly connected with an olefin source. In some embodiments, the internal static mixer is fluidly connected with an olefin feed conduit. In some embodiments, the internal static mixer is fluidly connected with a feed dryer wherein water contained in the olefin feed is removed. In some embodiments, the internal static mixer is fluidly connected with a recycled isoparaffin source. In some embodiments, the internal static mixer is fluidly connected with the fractionation section to receive the recycled isoparaffin. In some embodiments, the internal static mixer is fluidly connected with the isoparaffin fraction outlet of a fractionator wherein an isoparaffin fraction is generated. In some embodiments, the recycled isoparaffin is a recycled isobutane. In some embodiments, the internal static mixer is fluidly connected with a makeup isoparaffin (e.g., isobutane) source.

The olefin, makeup isoparaffin and recycled isoparaffin can be introduced into the internal static mixer separately or as a mixture of any two or three of them. In some embodiments, the internal static mixer has two inlets connected with the olefin feed conduit and the recycled isoparaffin conduit respectively, and the makeup isoparaffin is fed through the olefin feed conduit or the recycled isoparaffin conduit. In some embodiments, the internal static mixer has one inlet connected with a conduit transporting the mixture of olefin, makeup isoparaffin and recycled isoparaffin. These one or two inlets are typically located at the inlet end or upstream end of the internal static mixer. The conduit(s) for transporting olefin, makeup isoparaffin, and/or recycled isoparaffin can sealingly extend through the wall of the shell to be connected with the internal static mixer.

In some embodiments, the external static mixer is also fluidly connected with the refrigeration section of the sulfuric acid alkylation unit to receive a refrigerant recycle stream comprising isoparaffin (e.g., isobutane). In some embodiments, the refrigeration section further comprises a refrigerant recycle pump which is used to send the refrigerant recycle stream to the reactor system, and the external static mixer is fluidly connected with the refrigerant recycle pump. In some embodiments, the external static mixer has an inlet connected with a conduit transporting the refrigerant recycle stream. Such inlet is typically located at the inlet end or upstream end of the external static mixer. In some embodiments, the external static mixer is also fluidly connected with an olefin source, a recycled isoparaffin source and/or a makeup isoparaffin source, all upstream of the external static mixer. In some embodiments, the external static mixer is also fluidly connected with an olefin feed conduit, a conduit for recycling isoparaffin, and/or a conduit for feeding makeup isoparaffin, all upstream of the external static mixer.

A distributor can be directly connected with the internal static mixer. In some embodiments, the distributor extends from the internal static mixer substantially along the bottom interior surface of the reactor vessel. In some embodiments, the distributor is mounted directly on the outlet end of the internal static mixer. In some embodiments, both the internal static mixer and the distributor are cylindrical and in some embodiments can have substantially the same inner diameter. In some embodiments, the longitudinal axis of the internal static mixer is generally coincident with the longitudinal axis of the distributor.

The reactor system can comprise one or more internal static mixers and one or more distributors. For example, two or more distributors can be directly connected with a single internal static mixer. The reactor system can also comprise two or more sets of internal static mixer and distributor. In some embodiments, the reactor system comprises two or more sets of internal static mixer and distributor, each set has one internal static mixer and one distributor directly connected with each other, and a different emulsion pump is provided for each set respectively. In some embodiments, the reactor system comprises one to three internal static mixers in combination with one to ten distributors.

In some embodiments, the reactor system further comprises a plurality of draft tubes inside the reactor vessel to help mixing hydrocarbon phase with sulfuric acid phase. The plurality of draft tubes extends upwardly from above the distributor to an elevation below the liquid level (i.e., liquid surface) in the reactor vessel during an alkylation process. Each of the draft tubes independently has a bottom end and a top end, and both ends are open. The bottom end is above the distributor, and the top end is below the liquid level in the reactor vessel during an alkylation process. In some embodiments, the top end of the draft tube is no more than 20 inches below the liquid level, or no more than 15 inches below the liquid level, or no more than 10 inches below the liquid level, or no more than 5 inches below the liquid level, or no more than 3 inches below the liquid level. In some embodiments, the bottom end of the draft tube is no more than 30 inches above the distributor, or no more than 25 inches above the distributor, or no more than 20 inches above the distributor, or no more than 15 inches above the distributor, or no more than 10 inches above the distributor, or no more than 6 inches above the distributor.

In some embodiments, the draft tubes are hollow or empty inside, that is, the draft tubes have no internal structure, packing or components inside. In some embodiments, the draft tube has no perforation on the wall. The draft tubes can have various shapes. In some embodiments, the draft tubes are substantially cylindrical. In some embodiments, the draft tubes are straight and have same inner diameters from top to bottom. In some embodiments, the draft tubes have inner diameters in the range of from about 1 inch to about 10 inches, or from about 2 inches to about 8 inches, or from about 3 inches to about 6 inches.

In some embodiments, the draft tubes are fixed above the perforations of the distributor so that bubbles generated from the perforations can enter and pass through the draft tubes. In some embodiments, the longitudinal axis of each draft tube is substantially perpendicular to the distributor. In some embodiments, the longitudinal axes of the draft tubes and the distributor substantially lie in the same vertical plane. The draft tubes can be fixed or secured in the reactor vessel in various ways. In some embodiments, the draft tubes can be fixed with supporting bars welded to the bottom of the reactor vessel.

The sulfuric acid/hydrocarbon emulsion generated in the reactor vessel can egress via an emulsion outlet. In some embodiments, the emulsion outlet is located at the lower portion of the reactor vessel, that is, the emulsion outlet is below the liquid level in the reactor vessel during an alkylation process. In some embodiments, the emulsion outlet is located at the lower end of the reactor vessel. In some embodiments, the emulsion outlet is at the bottom of the reactor vessel. The emulsion pump is fluidly connected with the emulsion outlet to provide emulsion recycle stream to the reactor vessel. In some embodiments, the emulsion pump is directly connected with the emulsion outlet.

In some embodiments, the reactor vessel further comprises a second emulsion outlet fluidly connected with a sulfuric acid settler outside the reactor vessel, and a portion of the sulfuric acid/hydrocarbon emulsion generated in the reactor vessel exits from the second emulsion outlet and is sent to the sulfuric acid settler wherein the hydrocarbon phase is separated from the sulfuric acid phase (i.e., spent acid). In such embodiments, the emulsion outlet fluidly connected with the emulsion pump as disclosed above is the first emulsion outlet. In some embodiments, the reactor system comprises: (a) a closed reactor vessel comprising a shell, a vapor outlet, a first emulsion outlet and a second emulsion outlet; (b) an internal static mixer located at the lower portion of the reactor vessel; (c) a distributor directly connected with the internal static mixer; and (d) an emulsion pump fluidly connected with the internal static mixer and the first emulsion outlet; wherein the emulsion pump is located outside the reactor vessel, the distributor is located at the lower portion of the reactor vessel, and the second emulsion outlet is fluidly connected with a sulfuric acid settler outside the reactor vessel. In such embodiments, typically there is no partition baffle inside the reactor vessel, and the internal static mixer and distributor can extend substantially the entire horizontal length of the reactor vessel. In some embodiments, the emulsion pump is also fluidly connected with the sulfuric acid settler outside the reactor vessel to receive the spent acid separated out in the sulfuric acid settler and recycle the spent acid to the reactor vessel. In some embodiments, the second emulsion outlet is at a higher elevation than the first emulsion outlet. In some embodiments, the first emulsion outlet is at the lower end or at the bottom of the reactor vessel, while the second emulsion outlet is at the downstream end of the reactor vessel.

In some embodiments, the mixer is a homogenizer outside the reactor vessel, that is, the homogenizer can be used in lieu of the internal static mixer for mixing hydrocarbon reactants with sulfuric acid catalyst. In some embodiments, the sulfuric acid alkylation reactor system comprises: (a) a closed reactor vessel comprising a shell, a vapor outlet, and an emulsion outlet; (b) a distributor located at the lower portion of the reactor vessel; (c) a homogenizer fluidly connected with the distributor; and (d) an emulsion pump fluidly connected with the homogenizer and the emulsion outlet; wherein the homogenizer and the emulsion pump are located outside the reactor vessel. In some embodiments, there is a mixer between the homogenizer and the distributor, and the mixer can be an internal static mixer, an external static mixer, or their combination. In some embodiments, there is no mixer between the homogenizer and the distributor, and the homogenizer is directly connected with the distributor. In some embodiments, the reactor system comprises no internal static mixer inside the reactor vessel, and the homogenizer is directly connected with the distributor. In some embodiments, the homogenizer is a rotor stator mixer. In some embodiments, the homogenizer is an in-line rotor stator mixer.

The homogenizer is upstream of the distributor. The reactor system can comprise one or more distributors. In some embodiments, the reactor system comprises two or more distributors. In some embodiments, said two or more distributors are respectively directly connected with a single homogenizer. In some embodiments, each of said two or more distributors is directly connected with a different homogenizer. In some embodiments, each set of distributor and homogenizer is fluidly connected with a different emulsion pump. In some embodiments, the reactor system comprises one to ten distributors.

In some embodiments, the homogenizer is fluidly connected with an olefin source upstream of the homogenizer with respect to the flow direction of olefin. In some embodiments, the homogenizer is fluidly connected with an olefin feed conduit upstream of the homogenizer with respect to the flow direction of olefin. In some embodiments, the homogenizer is fluidly connected with a feed dryer wherein water contained in the olefin feed is removed. In some embodiments, the homogenizer is fluidly connected with a recycled isoparaffin source upstream of the homogenizer with respect to the flow direction of isoparaffin. In some embodiments, the homogenizer is fluidly connected with the fractionation section to receive the recycled isoparaffin. In some embodiments, the homogenizer is fluidly connected with the isoparaffin fraction outlet of a fractionator wherein an isoparaffin fraction is generated. In some embodiments, the recycled isoparaffin is a recycled isobutane. In some embodiments, the homogenizer is fluidly connected with a makeup isoparaffin (e.g., isobutane) source. The olefin, makeup isoparaffin and recycled isoparaffin can be introduced into the homogenizer separately or as a mixture of any two or three of them.

In some embodiments, there is no external static mixer in the reactor system, the homogenizer is directly connected with the emulsion pump, and a refrigerant recycle stream from the refrigeration section is introduced into the connecting conduit between the homogenizer and the emulsion pump. In some embodiments, the homogenizer is fluidly connected with a refrigerant recycle pump in the refrigeration section.

In some embodiments, the reactor system further comprises an external static mixer fluidly connected with the homogenizer and the emulsion pump, and the external static mixer is located outside the reactor vessel. In some embodiments, the reactor system comprises: (a) a closed reactor vessel comprising a shell, a vapor outlet, and an emulsion outlet; (b) a distributor located at the lower portion of the reactor vessel; (c) a homogenizer fluidly connected with the distributor; (d) an external static mixer fluidly connected with the homogenizer; and (e) an emulsion pump fluidly connected with the emulsion outlet and the external static mixer; wherein the emulsion pump is located outside the reactor vessel. In some embodiments, the external static mixer is directly connected with the homogenizer and is also directly connected with the emulsion pump, and the homogenizer is directly connected with the distributor.

In some embodiments, the external static mixer is also fluidly connected with the refrigeration section of the sulfuric acid alkylation unit to receive a refrigerant recycle stream comprising isoparaffin (e.g., isobutane). In some embodiments, the refrigeration section further comprises a refrigerant recycle pump which is used to send the refrigerant recycle stream to the reactor system, and the external static mixer is fluidly connected with the refrigerant recycle pump. In some embodiments, the external static mixer has an inlet connected with a conduit transporting the refrigerant recycle stream. Such inlet is typically located at the upstream end of the external static mixer.

The emulsion pump is fluidly connected with the emulsion outlet to provide emulsion recycle stream to the reactor vessel. In some embodiments, the emulsion pump is directly connected with the emulsion outlet. In some embodiments, the emulsion outlet is located at the lower portion of the reactor vessel. In some embodiments, the emulsion outlet is located at the lower end of the reactor vessel. In some embodiments, the emulsion outlet is at the bottom of the reactor vessel.

In some embodiments, the reactor vessel further comprises a second emulsion outlet fluidly connected with a sulfuric acid settler outside the reactor vessel, and a portion of the sulfuric acid/hydrocarbon emulsion generated in the reactor vessel exits from the second emulsion outlet and is sent to the sulfuric acid settler wherein the hydrocarbon phase is separated from the sulfuric acid phase (i.e., spent acid). In some embodiments, the reactor system comprises: (a) a closed reactor vessel comprising a shell, a vapor outlet, a first emulsion outlet and a second emulsion outlet; (b) a distributor located at the lower portion of the reactor vessel; (c) a homogenizer fluidly connected with the distributor; and (d) an emulsion pump fluidly connected with the homogenizer and the first emulsion outlet; wherein the homogenizer and the emulsion pump are located outside the reactor vessel, and the second emulsion outlet is fluidly connected with a sulfuric acid settler outside the reactor vessel. In such embodiments, typically there is no partition baffle inside the reactor vessel, and the distributor can extend substantially the entire horizontal length of the reactor vessel. In some embodiments, the emulsion pump is also fluidly connected with the sulfuric acid settler outside the reactor vessel to receive the spent acid separated out in the sulfuric acid settler and recycle the spent acid to the reactor vessel. In some embodiments, the second emulsion outlet is at a higher elevation than the first emulsion outlet. In some embodiments, the first emulsion outlet is at the lower end or at the bottom of the reactor vessel, while the second emulsion outlet is at the downstream end of the reactor vessel.

In some embodiments, the reactor vessel further comprises a partition baffle and a coalescing media. In such embodiments, both the reaction zone and the acid settling zone reside in the same reactor vessel, and in some embodiments, there is no sulfuric acid settler outside the reactor vessel. The emulsion pump is fluidly connected with the spent acid outlet to receive the spent acid separated out in the acid settling zone and mix it with the emulsion to be sent back to the reactor vessel.

In some embodiments, the reactor system comprises: (a) a closed reactor vessel comprising a shell, a vapor outlet, an emulsion outlet, a partition baffle, a coalescing media, a spent acid outlet, and a net effluent outlet; (b) a distributor located at the lower portion of the reactor vessel; (c) a mixer fluidly connected with the distributor; and (d) an emulsion pump fluidly connected with the mixer, the emulsion outlet and the spent acid outlet; wherein the emulsion pump is located outside the reactor vessel, the partition baffle and the coalescing media extend upwardly from the bottom of the reactor vessel respectively, the coalescing media is downstream of the partition baffle and defines a reaction zone and an acid settling zone inside the reactor vessel, the reaction zone is upstream of the coalescing media, the acid settling zone is downstream of the coalescing media, and the distributor is located at the reaction zone and is upstream of the partition baffle.

In some embodiments, the emulsion outlet is at the lower portion of the reaction zone. In some embodiments, the emulsion outlet is at the lower end of the reaction zone. In some embodiments, the emulsion outlet is at the bottom of the reaction zone. In some embodiments, the spent acid outlet is at the lower portion of the acid settling zone below the liquid level of the sulfuric acid phase. In some embodiments, the spent acid outlet is at the lower end of the acid settling zone. In some embodiments, the spent acid outlet is at the bottom of the acid settling zone. In some embodiments, the reactor system further comprises a spent acid pump outside the reactor vessel directly connected with the spent acid outlet, the spent acid pump is upstream of the emulsion pump and is fluidly connected with the emulsion pump to send the spent acid to the emulsion pump. In some embodiments, the spent acid pump is directly connected with the emulsion pump.

The liquid hydrocarbon phase leaves the reactor vessel through the net effluent outlet to be purified and fractionated to produce an alkylate product. In some embodiments, the net effluent outlet is downstream of the coalescing media. In some embodiments, there is no second partition baffle in the reactor vessel, and the net effluent outlet is located in the acid settling zone. In such embodiments, the net effluent outlet is above the acid phase level but below the liquid hydrocarbon phase level. In some embodiments, the net effluent outlet is fluidly connected with a feed/effluent heat exchanger for cooling a hydrocarbon feed stream and heating the net effluent stream. In some embodiments, the net effluent outlet is fluidly connected with a net effluent treatment section of the sulfuric acid alkylation unit where the net effluent is purified. In some embodiments, the net effluent outlet is fluidly connected with a fractionator in the fractionation section to generate recycled isoparaffin and/or alkylate product.

When the reactor vessel is a vertical reactor vessel, in some embodiments, the reactor system further comprises a raised sump inside the reactor vessel to collect the liquid hydrocarbon phase formed or separated out in the acid settling zone.

In some embodiments, the mixer is an internal static mixer. In some embodiments, the reactor system comprises: (a) a closed reactor vessel comprising a shell, a vapor outlet, an emulsion outlet, a partition baffle, a coalescing media, a spent acid outlet, and a net effluent outlet; (b) an internal static mixer; (c) a distributor directly connected with the internal static mixer; and (d) an emulsion pump fluidly connected with the internal static mixer, the emulsion outlet and the spent acid outlet; wherein the emulsion pump is located outside the reactor vessel, the partition baffle and the coalescing media extend upwardly from the bottom of the reactor vessel respectively, the coalescing media is downstream of the partition baffle and defines a reaction zone and an acid settling zone inside the reactor vessel, the reaction zone is upstream of the coalescing media, the acid settling zone is downstream of the coalescing media, both the internal static mixer and the distributor are located at the lower portion of the reaction zone, and the distributor is downstream of the internal static mixer and is upstream of the partition baffle. In some embodiments, the internal static mixer and distributor can extend substantially the entire horizontal length of the reaction zone. In some embodiments, as disclosed above, there is no external static mixer in the reactor system. In some embodiments, as disclosed above, the reactor system further comprises an external static mixer fluidly connected with the internal static mixer and the emulsion pump.

In some embodiments, the mixer is a homogenizer outside the reactor vessel. In some embodiments, the reactor system comprises: (a) a closed reactor vessel comprising a shell, a vapor outlet, an emulsion outlet, a partition baffle, a coalescing media, a spent acid outlet, and a net effluent outlet; (b) a distributor; (c) a homogenizer fluidly connected with the distributor; and (d) an emulsion pump fluidly connected with the homogenizer, the emulsion outlet and the spent acid outlet; wherein the homogenizer and the emulsion pump are located outside the reactor vessel, the partition baffle and the coalescing media extend from the bottom of the reactor vessel respectively, the coalescing media is downstream of the partition baffle and defines a reaction zone and an acid settling zone inside the reactor vessel, the reaction zone is upstream of the coalescing media, the acid settling zone is downstream of the coalescing media, and the distributor is located at the lower portion of the reaction zone and is upstream of the partition baffle. In some embodiments, the distributor can extend substantially the entire horizontal length of the reaction zone. In some embodiments, as disclosed above, there is no external static mixer in the reactor system. In some embodiments, as disclosed above, the reactor system further comprises an external static mixer fluidly connected with the internal static mixer and the emulsion pump.

The partition baffle is downstream from the distributor, and the coalescing media is downstream from the partition baffle. In some embodiments, the partition baffle and the coalescing media extend through the shell respectively at the lower portion of the reactor vessel. In some embodiments, the partition baffle and the coalescing media are substantially parallel to each other, and the partition baffle is spaced a distance D upstream from the coalescing media. In some embodiments, the distance D is no more than 50%, or 40%, or 30%, or 20%, or 10% of the horizontal length of the reactor vessel. In some embodiments, the distance D is no more than 10 feet, or 9 feet, or 8 feet, or 7 feet, or 6 feet, or 5 feet, or 4 feet, or 3 feet, or 2 feet.

In some embodiments, the reactor vessel further comprises a second partition baffle downstream from the coalescing media. In such embodiments, the partition baffle upstream of the coalescing media is the first partition baffle. The second partition baffle extends upwardly from the bottom of the reactor vessel. The second partition baffle extends through the shell at the lower portion of the reactor vessel. In some embodiments, the second partition baffle is substantially parallel to the coalescing media. In some embodiments, the first partition baffle, the coalescing media, and the second partition baffle are substantially parallel to each other. The second partition baffle defines an effluent zone downstream of the second partition baffle, that is, the second partition baffle further divides the acid settling zone into an acid settling zone and an effluent zone. The acid settling zone is downstream of the coalescing media and upstream of the second partition baffle. The effluent zone is downstream of the second partition baffle. In some embodiments, the net effluent outlet is at the effluent zone and is below the liquid level. In some embodiments, the net effluent outlet is at the lower end of the effluent zone or at the bottom of the effluent zone.

In some embodiments, the reactor system comprises: (a) a closed reactor vessel comprising a shell, a vapor outlet, an emulsion outlet, a first partition baffle, a coalescing media, a second partition baffle, a spent acid outlet, and a net effluent outlet; (b) an internal static mixer; (c) a distributor directly connected with the internal static mixer; (d) an external static mixer directly connected with the internal static mixer; and (e) an emulsion pump directly connected with the external static mixer and the emulsion outlet and fluidly connected with the spent acid outlet; wherein the emulsion pump is located outside the reactor vessel; the first partition baffle, the second partition baffle and the coalescing media respectively extends upwardly from the bottom of the reactor vessel and respectively extends through the shell at the lower portion of the reactor vessel; the coalescing media is downstream of the first partition baffle and upstream of the second partition baffle; the coalescing media and the second partition baffle define a reaction zone, an acid settling zone, and an effluent zone inside the reactor vessel, the reaction zone is upstream of the coalescing media, the effluent zone is downstream of the second partition baffle, the acid settling zone is between the coalescing media and the second partition baffle; both the internal static mixer and the distributor are located at the lower portion of the reaction zone, the distributor is downstream of the internal static mixer and is upstream of the first partition baffle; the emulsion outlet is at the lower end of the reaction zone, the spent acid outlet is at the lower end of the acid settling zone, the net effluent outlet is at the lower end of the effluent zone, and the vapor outlet is at the upper end of the reactor vessel.

In some embodiments, the reactor system comprises: (a) a closed reactor vessel comprising a shell, a vapor outlet, an emulsion outlet, a first partition baffle, a coalescing media, a second partition baffle, a spent acid outlet, and a net effluent outlet; (b) a distributor upstream of the first partition baffle; (c) a homogenizer directly connected with the distributor; (d) an external static mixer directly connected with the homogenizer; and (e) an emulsion pump directly connected with the external static mixer and the emulsion outlet and fluidly connected with the spent acid outlet; wherein the emulsion pump is located outside the reactor vessel; the first partition baffle, the second partition baffle and the coalescing media respectively extends upwardly from the bottom of the reactor vessel and respectively extends through the shell at the lower portion of the reactor vessel; the coalescing media is downstream of the first partition baffle and upstream of the second partition baffle; the coalescing media and the second partition baffle define a reaction zone, an acid settling zone, and an effluent zone inside the reactor vessel, the reaction zone is upstream of the coalescing media, the effluent zone is downstream of the second partition baffle, the acid settling zone is between the coalescing media and the second partition baffle; the distributor is located at the lower portion of the reaction zone and is downstream of the homogenizer; the emulsion outlet is at the lower end of the reaction zone, the spent acid outlet is at the lower end of the acid settling zone, the net effluent outlet is at the lower end of the effluent zone, and the vapor outlet is at the upper end of the reactor vessel.

Both the first partition baffle and the second partition baffle are liquid impermeable. The sulfuric acid/hydrocarbon emulsion in the reaction zone passes through the coalescing media to enter the acid settling zone, and the coalescing media acts to separate the sulfuric acid phase from the hydrocarbon phase. In some embodiments, the first partition baffle is a transverse baffle having a top. In some embodiments, the top is substantially horizontal and has a distance below the top interior surface of the reactor vessel. The top of the first partition baffle is below the liquid level in the reaction zone so that the emulsion egressing from the distributor flows over the top of the first partition baffle and then passes through the coalescing media to enter the acid settling zone.

In some embodiments, the coalescing media is a transverse coalescing media having a top. In some embodiments, the top is substantially horizontal and has a distance below the top interior surface of the reactor vessel. In some embodiments, the top of the coalescing media is above the liquid level in the reaction zone so that the emulsion in the reaction zone passes through the coalescing media to enter the acid settling zone. In some embodiments, the coalescing media is higher in height than the first partition baffle. In some embodiments, the coalescing media has substantially the same height as the first partition baffle. In some embodiments, the coalescing media is a transverse coalescing media substantially occupying a cross-sectional area of the reactor vessel, and the periphery of the coalescing media is attached to the interior wall of the reactor vessel. In some embodiments, the coalescing media may comprise one or more layers of coalescing fiber or coalescing media. For example, the coalescing media may comprise, consist essentially of, or consist of two layers, the first layer coalescing media serves to coalesce small droplets of sulfuric acid into large droplets, and the second layer coalescing media directs the large coalesced droplets toward the bottom of the reactor vessel.

In the acid settling zone, the sulfuric acid/hydrocarbon emulsion separates into a sulfuric acid phase at the bottom and a liquid hydrocarbon phase above the sulfuric acid phase. In some embodiments, the second partition baffle is a transverse baffle having a top. In some embodiments, the top is substantially horizontal and has a distance below the top interior surface of the reactor vessel. The top of the second partition baffle is above the sulfuric acid phase level but below the liquid hydrocarbon phase level in the acid settling zone so that the liquid hydrocarbon phase flows over the top of the second partition baffle moving from the acid settling zone to the effluent zone. In some embodiments, the second partition baffle is lower in height than the first partition baffle. In some embodiments, the second partition baffle has substantially the same height as the first partition baffle.

In some embodiments, the reactor vessel is horizontal, and the coalescing media, the first partition baffle and the second partition baffle are substantially perpendicular to the longitudinal axis of the reactor vessel. In some embodiments, the reactor vessel is vertical and substantially cylindrical, and the coalescing media, the first partition baffle and the second partition baffle are substantially perpendicular to a horizontal diameter line.

The present disclosure also provides a split sulfuric acid alkylation reactor system wherein a single relatively elongated horizontal reactor vessel is split to accommodate two reactor systems. The reactor system comprises: (a) a closed horizontal reactor vessel comprising a shell, a vapor outlet, a first emulsion outlet, a second emulsion outlet, a first partition baffle, a first coalescing media, a second partition baffle, a second coalescing media, a spent acid outlet, and a net effluent outlet; (b) a first distributor located at the lower portion of the reactor vessel; (c) a second distributor located at the lower portion of the reactor vessel; (d) a first mixer fluidly connected with the first distributor; (e) a second mixer fluidly connected with the second distributor; (f) a first emulsion pump fluidly connected with the first mixer, the first emulsion outlet, and the spent acid outlet; and (g) a second emulsion pump fluidly connected with the second mixer, the second emulsion outlet, and the spent acid outlet; wherein the first partition baffle, the second partition baffle, the first coalescing media, and the second coalescing media extend upwardly from the bottom of the reactor vessel respectively, the first coalescing media is downstream of the first partition baffle, the second coalescing media is downstream of the second partition baffle, the first coalescing media and the second coalescing media define a first reaction zone, a second reaction zone and an acid settling zone inside the reactor vessel, the first reaction zone is upstream of the first coalescing media, the second reaction zone is upstream of the second coalescing media, the acid settling zone is between the first coalescing media and the second coalescing media, the first distributor is located at the first reaction zone, the second distributor is located at the second reaction zone, the first emulsion pump and the second emulsion pump are located outside the reactor vessel.

Features and embodiments disclosed in this disclosure for various reactor systems and various components or elements such as the closed reactor vessel, shell, vapor outlet, emulsion outlet, partition baffle, coalescing media, spent acid outlet, net effluent outlet, distributor, draft tubes, mixer, internal static mixer, external static mixer, homogenizer, rotor stator mixer, emulsion pump, spent acid pump, raised sump, reaction zone, acid settling zone and effluent zone are also applicable to the split reactor system.

The two reactor systems on two sides of the reactor vessel can be same or different. In some embodiments, the first mixer and the second mixer is independently an internal static mixer, an external static mixer, or a homogenizer directly connected with the first distributor and the second distributor respectively. In some embodiments, both the first mixer and the second mixer are internal static mixers. In some embodiments, both the first mixer and the second mixer are homogenizers. In some embodiments, the first internal static mixer, the second internal static mixer, the first distributor and the second distributor all extend at the longitudinal direction of the reactor vessel.

In some embodiments, the split sulfuric acid alkylation reactor system is part of a sulfuric acid alkylation unit, and the sulfuric acid alkylation unit also comprises a refrigeration section, a fractionation section, and a net effluent treatment section. In some embodiments, the refrigeration section comprises a refrigerant compressor, a refrigerant condenser and a refrigerant recycle pump. In some embodiments, the vapor outlet is fluidly connected with the refrigeration section.

In some embodiments, the first distributor and/or the second distributor is substantially horizontal. In some embodiments, the first distributor and/or the second distributor extends substantially along the bottom interior surface of the reactor vessel. In some embodiments, the first mixer and/or the second mixer is an internal static mixer. In some embodiments, the first mixer is a first internal static mixer located at the lower portion of the first reaction zone, the first distributor is downstream of the first internal static mixer and is directly connected with the first internal static mixer. In some embodiments, the first distributor extends from the first internal static mixer. In some embodiments, the second mixer is a second internal static mixer located at the lower portion of the second reaction zone, the second distributor is downstream of the second internal static mixer and is directly connected with the second internal static mixer. In some embodiments, the second distributor extends from the second internal static mixer.

The first partition baffle is downstream from the first distributor, and the second partition baffle is downstream from the second distributor. In some embodiments, the first internal static mixer and the first distributor can extend substantially the entire horizontal length of the first reaction zone. In some embodiments, the second internal static mixer and the second distributor can extend substantially the entire horizontal length of the second reaction zone.

In some embodiments, the split sulfuric acid alkylation reactor system further comprises a first external static mixer fluidly connected with the first internal static mixer and the first emulsion pump. In some embodiments, the reactor system further comprises a second external static mixer fluidly connected with the second internal static mixer and the second emulsion pump. In some embodiments, the first external static mixer is directly connected with the first internal static mixer and is also directly connected with the first emulsion pump. In some embodiments, the second external static mixer is directly connected with the second internal static mixer and is also directly connected with the second emulsion pump.

In some embodiments, the first internal static mixer and/or the second internal static mixer is fluidly connected with an olefin source. They can be connected with the same or different olefin source. In some embodiments, the first internal static mixer and/or the second internal static mixer is fluidly connected with a recycled isoparaffin source. They can be connected with the same or different recycled isoparaffin source. In some embodiments, the first external static mixer and/or the second external static mixer is fluidly connected with the refrigerant recycle pump. They can be connected with the same or different refrigerant recycle pump. In some embodiments, the first external static mixer and/or the second external static mixer is also fluidly connected with an olefin source, a recycled isoparaffin source and/or a makeup isoparaffin source. The sources are upstream of the first external static mixer and/or the second external static mixer respectively and can be the same or different to the first and second external static mixers. In some embodiments, the first external static mixer and/or the second external static mixer is also fluidly connected with an olefin feed conduit, a conduit for recycling isoparaffin, and/or a conduit for feeding makeup isoparaffin. The conduits are upstream of the first external static mixer and/or the second external static mixer respectively and can be the same or different to the first and second external static mixers. In some embodiments, the reactor system comprises one to three first internal static mixers in combination with one to ten first distributors. In some embodiments, the reactor system comprises one to three second internal static mixers in combination with one to ten second distributors.

In some embodiments, the first mixer and/or the second mixer is a homogenizer. In some embodiments, the first mixer is a first homogenizer fluidly connected with the first distributor, and the first homogenizer is located outside the reactor vessel and is upstream of the first distributor. In some embodiments, the second mixer is a second homogenizer fluidly connected with the second distributor, and the second homogenizer is located outside the reactor vessel and is upstream of the second distributor. In some embodiments, the first homogenizer is a first rotor stator mixer or a first in-line rotor stator mixer. In some embodiments, the second homogenizer is a second rotor stator mixer or a second in-line rotor stator mixer. In some embodiments, the first in-line rotor stator mixer is directly connected with the first distributor. In some embodiments, the second in-line rotor stator mixer is directly connected with the second distributor. In some embodiments, there is no internal static mixer insider the reactor vessel, the first distributor can extend substantially the entire horizontal length of the first reaction zone, and the second distributor can extend substantially the entire horizontal length of the second reaction zone.

In some embodiments, the split sulfuric acid alkylation reactor system further comprises a first external static mixer fluidly connected with the first in-line rotor stator mixer and the first emulsion pump. In some embodiments, the first external static mixer is directly connected with the first in-line rotor stator mixer and is also directly connected with the first emulsion pump. In some embodiments, the reactor system further comprises a second external static mixer fluidly connected with the second in-line rotor stator mixer and the second emulsion pump. In some embodiments, the second external static mixer is directly connected with the second in-line rotor stator mixer and is also directly connected with the second emulsion pump.

In some embodiments, the first in-line rotor stator mixer is fluidly connected with an olefin source upstream of the first in-line rotor stator mixer with respect to the flow direction of olefin. In some embodiments, the second in-line rotor stator mixer is fluidly connected with an olefin source upstream of the second in-line rotor stator mixer with respect to the flow direction of olefin. The first in-line rotor stator mixer and the second in-line rotor stator mixer can be connected with same or different olefin source. In some embodiments, the first in-line rotor stator mixer is fluidly connected with a recycled isoparaffin source upstream of the first in-line rotor stator mixer with respect to the flow direction of isoparaffin. In some embodiments, the second in-line rotor stator mixer is fluidly connected with a recycled isoparaffin source upstream of the second in-line rotor stator mixer with respect to the flow direction of isoparaffin. The first in-line rotor stator mixer and the second in-line rotor stator mixer can be connected with same or different recycled isoparaffin source. In some embodiments, the first external static mixer and/or the second external static mixer is fluidly connected with the refrigerant recycle pump. They can be connected with same or different refrigerant recycle pump.

In some embodiments, the reactor system further comprises a plurality of first draft tubes extending upwardly from above the first distributor. In some embodiments, the reactor system further comprises a plurality of second draft tubes extending upwardly from above the second distributor. The draft tubes are located inside the reactor vessel to help mixing hydrocarbon phase with sulfuric acid phase. The draft tubes extend upwardly from above the distributor to an elevation below the liquid level (i.e., liquid surface) in the reactor vessel during an alkylation process. Each of the draft tubes independently has a bottom end and a top end, and both ends are open. The bottom end is above the distributor, and the top end is below the liquid level in the reactor vessel during an alkylation process. In some embodiments, the top end of the first draft tubes and/or the second draft tubes is no more than 20 inches below the liquid level, or no more than 15 inches below the liquid level, or no more than 10 inches below the liquid level, or no more than 5 inches below the liquid level, or no more than 3 inches below the liquid level. In some embodiments, the bottom end of the first draft tubes and/or the second draft tubes is no more than 30 inches above the distributor, or no more than 25 inches above the distributor, or no more than 20 inches above the distributor, or no more than 15 inches above the distributor, or no more than 10 inches above the distributor, or no more than 6 inches above the distributor.

In some embodiments, the reactor system further comprises a spent acid pump outside the reactor vessel directly connected with the spent acid outlet. The spent acid pump is upstream of the first emulsion pump and is fluidly connected with the first emulsion pump. The spent acid pump is also upstream of the second emulsion pump and is fluidly connected with the second emulsion pump. In some embodiments, the spent acid pump is directly connected with the first emulsion pump and the second emulsion pump respectively. In some embodiments, the first emulsion pump and/or the second emulsion pump is fluidly connected with a fresh acid source. They can be connected with same or different fresh acid source.

In some embodiments, the first partition baffle and the first coalescing media are substantially parallel to each other and extend through the shell respectively at the lower portion of the reactor vessel. The first partition baffle is spaced a distance D1 upstream from the first coalescing media. In some embodiments, the distance D1 is no more than 25%, or 20%, or 15%, or 10%, or 5% of the horizontal length of the reactor vessel. In some embodiments, the distance D1 is no more than 10 feet, or 9 feet, or 8 feet, or 7 feet, or 6 feet, or 5 feet, or 4 feet, or 3 feet, or 2 feet.

In some embodiments, the second partition baffle and the second coalescing media are substantially parallel to each other and extend through the shell respectively at the lower portion of the reactor vessel. The second partition baffle is spaced a distance D2 upstream from the second coalescing media. In some embodiments, the distance D2 is no more than 25%, or 20%, or 15%, or 10%, or 5% of the horizontal length of the reactor vessel. In some embodiments, the distance D2 is no more than 10 feet, or 9 feet, or 8 feet, or 7 feet, or 6 feet, or 5 feet, or 4 feet, or 3 feet, or 2 feet. In some embodiments, the first partition baffle, the first coalescing media, the second partition baffle, and the second coalescing media are all substantially parallel to each other.

In some embodiments, the vapor outlet is at the upper end or the top of the reactor vessel. In some embodiments, the first emulsion outlet and/or the second emulsion outlet is at the lower portion of the first reaction zone and/or the second reaction zone respectively. In some embodiments, the first emulsion outlet and/or the second emulsion outlet is at the lower end of the first reaction zone and/or the second reaction zone respectively. In some embodiments, the first emulsion outlet and/or the second emulsion outlet is at the bottom of the first reaction zone and/or the second reaction zone respectively. In some embodiments, the spent acid outlet is at the lower portion of the acid settling zone below the liquid level of the sulfuric acid phase. In some embodiments, the spent acid outlet is at the lower end of the acid settling zone. In some embodiments, the spent acid outlet is at the bottom of the acid settling zone.

In some embodiments, there is no third and fourth partition baffles in the reactor vessel, and the net effluent outlet is located in the acid settling zone. In some embodiments, the reactor system further comprises a raised sump inside the reactor vessel to collect the liquid hydrocarbon phase formed or separated out in the acid settling zone. The raised sump has an open top and an outlet. The top is below the liquid hydrocarbon phase level in the acid settling zone so that the liquid hydrocarbon phase can flow over the top to enter the raised sump. The top is also above the sulfuric acid phase level in the acid settling zone. In some embodiments, the outlet is the net effluent outlet. In some embodiments, the outlet is directly connected with the net effluent outlet. In some embodiments, the outlet is at the lower end or the bottom of the raised sump.

In some embodiments, the reactor system further comprises a third partition baffle and a fourth partition baffle. The third partition baffle and the fourth partition baffle extend upwardly from the bottom of the reactor vessel respectively. The third partition baffle is downstream of the first coalescing media, and the fourth partition baffle is downstream of the second coalescing media. The third partition baffle and the fourth partition baffle further divide the acid settling zone into a first acid settling zone, a second acid settling zone and an effluent zone. The first acid settling zone is between the first coalescing media and the third partition baffle, the second acid settling zone is between the second coalescing media and the fourth partition baffle, and the effluent zone is between the third partition baffle and the fourth partition baffle.

When there are third partition baffle and fourth partition baffle in the reactor vessel to separate the acid settling zone into a first acid settling zone and a second acid settling zone, the spent acid outlet comprises a first spent acid outlet and a second spent acid outlet. In some embodiments, the first spent acid outlet is at the lower end or at the bottom of the first acid settling zone. In some embodiments, the second spent acid outlet is at the lower end or at the bottom of the second acid settling zone. In some embodiments, the first emulsion pump is fluidly connected with the first spent acid outlet. In some embodiments, the second emulsion pump is fluidly connected with the second spent acid outlet. In some embodiments, the spent acid pump comprises a first spent acid pump and a second spent acid pump. The first spent acid pump is directly connected with the first spent acid outlet. The first spent acid pump is upstream of the first emulsion pump and is fluidly connected with the first emulsion pump. The second spent acid pump is directly connected with the second spent acid outlet. The second spent acid pump is upstream of the second emulsion pump and is fluidly connected with the second emulsion pump. In some embodiments, the net effluent outlet is at the effluent zone and is below the liquid level. In some embodiments, the net effluent outlet is at the lower end of the effluent zone or at the bottom of the effluent zone.

In some embodiments, the third partition baffle is substantially parallel to the first coalescing media. In some embodiments, the fourth partition baffle is substantially parallel to the second coalescing media. The third partition baffle and the fourth partition baffle extends through the shell at the lower portion of the reactor vessel respectively. Both the third partition baffle and the fourth partition baffle are liquid impermeable. In some embodiments, the four partition baffles and the two coalescing media in the reactor vessel are all substantially parallel to each other. In some embodiments, the four partition baffles and the two coalescing media in the reactor vessel are substantially perpendicular to the longitudinal axis of the reactor vessel.

In some embodiments, the first partition baffle, the second partition baffle, the third partition baffle, and/or the fourth partition baffle is a transverse baffle having a top. In some embodiments, the first coalescing media and/or the second coalescing media is a transverse coalescing media having a top. In some embodiments, the first coalescing media is higher in height than the first partition baffle. In some embodiments, the second coalescing media is higher in height than the second partition baffle. In some embodiments, the third partition baffle is lower in height than the first partition baffle. In some embodiments, the fourth partition baffle is lower in height than the second partition baffle.

The present disclosure also provides an alkylation process. The alkylation process comprises contacting an olefin with an isoparaffin in the presence of a sulfuric acid catalyst to produce a product mixture comprising an alkylate wherein the contacting is performed in the sulfuric acid alkylation reactor systems or the split sulfuric acid alkylation reactor systems as disclosed in this disclosure.

Alkylation reactions of this disclosure are carried out with molar ratio of isoparaffin to olefin introduced into the reactor system of greater than 1 to minimize undesired polymerization reactions. The term "molar ratio of isoparaffin to olefin introduced into the reactor system", as used herein, means the molar ratio of the total amount of isoparaffin to the total amount of olefin introduced into the reactor system. In some embodiments, the molar ratio of isoparaffin to olefin introduced into the reactor system is in the range of from about 2:1 to about 50:1, or in the range of from about 4:1 to about 20:1, or in the range of from about 5:1 to about 12:1.

In some embodiments, during an alkylation process, the ratio of the emulsion recycle stream flow rate to the olefin feed rate is in the range of from about 10 to about 150. In some embodiments, during an alkylation process, the ratio of the emulsion recycle stream flow rate to the olefin feed rate is in the range of from about 25 to about 100. By "emulsion recycle stream flow rate", it is meant herein the volumetric flow rate of the emulsion from the emulsion outlet being recycled to the reactor vessel by the emulsion pump. By "olefin feed rate", it is meant herein the volumetric rate of the olefin fed into the reactor system.

The sulfuric acid catalyst in this disclosure comprises a sulfuric acid. Typically, the sulfuric acid catalyst in this disclosure comprises, consists essentially of, or consists of an aqueous solution of sulfuric acid. The acid strength of the sulfuric acid solution in the reactor system is generally maintained high enough to avoid dilution of the acid catalyst and excessive side reactions, but low enough to avoid high viscosity acid (freezing acid). In some embodiments, the acid strength of the sulfuric acid solution in the reactor vessel is in the range of about 80 wt % to about 99.5 wt %, or in the range of about 86 wt % to about 99 wt %.

The volume percentage of the sulfuric acid solution in the reaction zone based on the total volume of sulfuric acid solution and hydrocarbons in the reaction zone is in the range of from about 5% to about 70%, or from about 5% to about 50%, or from about 5% to about 30%, or from about 10% to about 20%. The sulfuric acid solution comprises sulfuric acid and water and may also comprise acid soluble diluents such as acid soluble oils and sulfate esters if they are present.

The alkylation reactions can be carried out at effective conditions in the reactor vessel to generate a product mixture comprising alkylate. For example, the temperature in the reactor vessel can be in the range of from about 0° C. to about 30° C. In some embodiments, the temperature in the reactor vessel is in the range of from about 4° C. to about 20° C. In some embodiments, the temperature in the reactor vessel is in the range of from about 7° C. to about 12° C. The pressure in the reactor vessel can be in the range of from about 1 to about 100 psig, or in the range of from about 2 to about 50 psig, or in the range of from about 3 to about 20 psig.

In some embodiments, the reactor system comprises: (a) a closed reactor vessel comprising a shell, a vapor outlet, and an emulsion outlet; (b) a distributor located at the lower portion of the reactor vessel; (c) a mixer fluidly connected with the distributor; and (d) an emulsion pump fluidly connected with the mixer and the emulsion outlet; wherein the emulsion pump is located outside the reactor vessel. In such embodiments, the alkylation process may comprise: (a) mixing the olefin and/or the isoparaffin with the sulfuric acid catalyst in the mixer to generate an emulsion; (b) directing the emulsion to the distributor and injecting the emulsion into the reactor vessel through the distributor; and (c) recycling a portion of the emulsion through the emulsion pump. In some embodiments, another portion of the emulsion can be sent to a sulfuric acid settler outside the reactor vessel.

In some embodiments, the reactor system comprises: (a) a closed reactor vessel comprising a shell, a vapor outlet, an emulsion outlet, a partition baffle, a coalescing media, a spent acid outlet, and a net effluent outlet; (b) a distributor located at the lower portion of the reactor vessel; (c) a mixer fluidly connected with the distributor; and (d) an emulsion pump fluidly connected with the mixer, the emulsion outlet and the spent acid outlet; wherein the emulsion pump is located outside the reactor vessel, the partition baffle and the coalescing media extend upwardly from the bottom of the reactor vessel respectively, the coalescing media is downstream of the partition baffle and defines a reaction zone and an acid settling zone inside the reactor vessel, the reaction zone is upstream of the coalescing media, the acid settling zone is downstream of the coalescing media, and the distributor is located at the reaction zone and is upstream of the partition baffle. In such embodiments, the alkylation process may comprise: (a) mixing the olefin and/or the isoparaffin with the sulfuric acid catalyst in the mixer to generate an emulsion; (b) directing the emulsion to the distributor and injecting the emulsion into the reaction zone through the distributor; (c) recycling a portion of the emulsion through the emulsion pump; (d) passing the portion of the emulsion not recycled over the partition baffle and through the coalescing media into the acid settling zone; (e) separating a hydrocarbon phase from a sulfuric acid phase in the acid settling zone; (f) recycling at least a portion of the sulfuric acid phase to the mixer and the reaction zone; and (g) directing at least a portion of the hydrocarbon phase to a net effluent treatment section.

In some embodiments, the reactor system comprises: (a) a closed reactor vessel comprising a shell, a vapor outlet, an emulsion outlet, a first partition baffle, a coalescing media, a second partition baffle, a spent acid outlet, and a net effluent outlet; (b) a distributor; (c) a mixer fluidly connected with the distributor; and (d) an emulsion pump fluidly connected with the mixer, the emulsion outlet and the spent acid outlet; wherein the emulsion pump is located outside the reactor vessel; the first partition baffle, the second partition baffle and the coalescing media respectively extends upwardly from the bottom of the reactor vessel and respectively extends through the shell at the lower portion of the reactor vessel; the coalescing media is downstream of the first partition baffle and upstream of the second partition baffle; the coalescing media and the second partition baffle define a reaction zone, an acid settling zone, and an effluent zone inside the reactor vessel, the reaction zone is upstream of the coalescing media, the effluent zone is downstream of the second partition baffle, the acid settling zone is between the coalescing media and the second partition baffle; the distributor is located at the lower portion of the reaction zone, the distributor is downstream of the mixer and is upstream of the first partition baffle. In such embodiments, the alkylation process may comprise: (a) mixing the olefin and/or the isoparaffin with the sulfuric acid catalyst in the mixer to generate an emulsion; (b) directing the emulsion to the distributor and injecting the emulsion into the reaction zone through the distributor; (c) recycling a portion of the emulsion through the emulsion pump; (d) passing the portion of the emulsion not recycled over the first partition baffle and through the coalescing media into the acid settling zone; (e) separating a hydrocarbon phase from a sulfuric acid phase in the acid settling zone; (f) recycling at least a portion of the sulfuric acid phase to the mixer and the reaction zone; (g) passing the hydrocarbon phase over the second partition baffle moving from the acid settling zone into the effluent zone; and (h) directing at least a portion of the hydrocarbon phase to a net effluent treatment section.

In some embodiments, the mixer is selected from the group consisting of an internal static mixer, an external static mixer, a homogenizer, and combinations thereof. In some embodiments, the emulsion injected into the reactor vessel through the distributor is partially flashed to generate vapor bubbles rising to the upper portion of the reactor vessel. The flashing helps to keep the reaction temperature low, and the rising vapor bubbles helps to keep the hydrocarbon phase and the sulfuric acid phase mixed and finely dispersed in the reaction zone or in the reactor vessel. In some embodiments, the reactor system comprises a plurality of draft tubes extending upwardly from above the distributor, and at least a portion of the vapor bubbles rise into and pass through the draft tubes. The draft tubes can improve the mixing efficiency of the rising vapor bubbles.

In some embodiments, the split sulfuric acid alkylation reactor system comprises: (a) a closed horizontal reactor vessel comprising a shell, a vapor outlet, a first emulsion outlet, a second emulsion outlet, a first partition baffle, a first coalescing media, a second partition baffle, a second coalescing media, a spent acid outlet, and a net effluent outlet; (b) a first distributor located at the lower portion of the reactor vessel; (c) a second distributor located at the lower portion of the reactor vessel; (d) a first mixer fluidly connected with the first distributor; (e) a second mixer fluidly connected with the second distributor; (f) a first emulsion pump fluidly connected with the first mixer, the first emulsion outlet, and the spent acid outlet; and (g) a second emulsion pump fluidly connected with the second mixer, the second emulsion outlet, and the spent acid outlet; wherein the first partition baffle, the second partition baffle, the first coalescing media, and the second coalescing media extend upwardly from the bottom of the reactor vessel respectively, the first coalescing media is downstream of the first partition baffle, the second coalescing media is downstream of the second partition baffle, the first coalescing media and the second coalescing media define a first reaction zone, a second reaction zone and an acid settling zone inside the reactor vessel, the first reaction zone is upstream of the first coalescing media, the second reaction zone is upstream of the second coalescing media, the acid settling zone is between the first coalescing media and the second coalescing media, the first distributor is located at the first reaction zone, the second distributor is located at the second reaction zone, the first emulsion pump and the second emulsion pump are located outside the reactor vessel. In such embodiments, the alkylation process may comprise: (a) mixing a first olefin and/or a first isoparaffin with a first sulfuric acid catalyst in the first mixer to generate a first emulsion; (b) directing the first emulsion to the first distributor and injecting the first emulsion into the first reaction zone through the first distributor; (c) recycling a portion of the first emulsion to the first reaction zone through the first emulsion pump; (d) passing the portion of the first emulsion not recycled over the first partition baffle and through the first coalescing media into the acid settling zone; (e) mixing a second olefin and/or a second isoparaffin with a second sulfuric acid catalyst in the second mixer to generate a second emulsion; (f) directing the second emulsion to the second distributor and injecting the second emulsion into the second reaction zone through the second distributor; (g) recycling a portion of the second emulsion to the second reaction zone through the second emulsion pump; (h) passing the portion of the second emulsion not recycled over the second partition baffle and through the second coalescing media into the acid settling zone; (i) separating a hydrocarbon phase from a sulfuric acid phase in the acid settling zone; (j) recycling a portion of the sulfuric acid phase to the first mixer and the first reaction zone; (k) recycling another portion of the sulfuric acid phase to the second mixer and the second reaction zone; and (l) directing at least a portion of the hydrocarbon phase to a net effluent treatment section.

In some embodiments, the first mixer and the second mixer are independently selected from the group consisting of an internal static mixer, an external static mixer, a homogenizer, and combinations thereof. In some embodiments, the first emulsion and the second emulsion injected into the first reaction zone and the second reaction zone respectively are partially flashed to generate vapor bubbles rising to the upper portion of the first reaction zone and the second reaction zone respectively. In some embodiments, the reactor system further comprises a plurality of first draft tubes extending upwardly from above the first distributor, and at least a portion of the vapor bubbles generated in the first reaction zone rise into and pass through the first draft tubes. In some embodiments, the reactor system further comprises a plurality of second draft tubes extending upwardly from above the second distributor, and at least a portion of the vapor bubbles generated in the second reaction zone rise into and pass through the second draft tubes.

In some embodiments, a vapor comprising isoparaffin is generated in the reactor vessel, and said vapor exits the reactor vessel through the vapor outlet and is directed to a refrigeration section.

U.S. Pat. No. 5,284,990 to Peterson et al. disclosed a method for converting an HF alkylation unit to a SA alkylation unit, the disclosure of which is incorporated herein by reference in its entirety for all purposes.

The present disclosure provides a method for converting a hydrogen fluoride alkylation unit which utilizes hydrogen fluoride as a reaction catalyst to a sulfuric acid alkylation unit, the method comprising: (a) substituting sulfuric acid for hydrogen fluoride as the reaction catalyst; and (b) modifying a suitable vessel in the hydrogen fluoride alkylation unit to provide a sulfuric acid alkylation reactor system or a split sulfuric acid alkylation reactor system as disclosed in this disclosure, wherein the suitable vessel is retained as the reactor vessel in the sulfuric acid alkylation reactor system or the split sulfuric acid alkylation reactor system.

In some embodiments, the HF alkylation unit is a gravity-flow HF alkylation unit (Phillips HF alkylation unit). In some embodiments, the HF alkylation unit is a pumped-flow HF alkylation unit (UOP HF alkylation unit). In some embodiments, a suitable vessel in an HF alkylation unit can be retained or modified to provide a reactor vessel in the SA alkylation reactor system or the split SA alkylation reactor system, and such suitable vessel can be retained or modified to provide the SA alkylation reactor system or the split SA alkylation reactor system as disclosed in this disclosure.

In some embodiments, the suitable vessel is selected from the group consisting of HF acid settlers and HF storage tanks. In some embodiments, the HF acid settler is a horizontal HF acid settler, for example, in a pumped-flow HF alkylation unit, and said horizontal HF acid settler is retained or modified to provide a closed horizontal reactor vessel in the SA alkylation reactor system or the split SA alkylation reactor system. In some embodiments, the HF acid settler is a vertical HF acid settler, for example, in a gravity-flow HF alkylation unit, and said vertical HF acid settler is retained or modified to provide a closed vertical reactor vessel in the SA alkylation reactor system. In some embodiments, the suitable vessel is an HF storage tank. In some embodiments, such HF storage tank is a remote HF storage tank. In some embodiments, the HF storage tank is horizontal, and said horizontal HF storage tank is retained or modified to provide a closed horizontal reactor vessel in the SA alkylation reactor system or the split SA alkylation reactor system.

In some embodiments, an HF acid settler can be retained or modified to provide a sulfuric acid settler in the converted SA alkylation unit to be used in combination with the alkylation reactor system therein. In some embodiments, a horizontal HF acid settler can be retained or modified to provide a horizontal SA settler in the converted SA alkylation unit to be used in combination with the alkylation reactor system therein. In some embodiments, a vertical HF acid settler can be retained or modified to provide a vertical SA settler in the converted SA alkylation unit to be used in combination with the alkylation reactor system therein.

In some embodiments, the remote HF storage tank can be retained or modified to provide a sulfuric acid blowdown drum (e.g., 1709 in FIG. 21) or a spent acid aftersettler (e.g., 1707 in FIG. 21) in the converted SA alkylation unit. The spent acid aftersettler is used to further separate the hydrocarbon phase or remove the residual hydrocarbons from the sulfuric acid phase. In some embodiments, the remote HF storage tank is retrofitted to provide the sulfuric acid blowdown drum by installing a vertical baffle in the tank to separate the acid and hydrocarbon zones. In some embodiments, the existing HF alkylation unit further comprises a remote HF blowdown drum, and said remote HF blowdown drum can be retained or modified to provide a sulfuric acid blowdown drum or a spent acid aftersettler in the converted SA alkylation unit.

The present disclosure also provides a method for converting a hydrogen fluoride alkylation unit which utilizes hydrogen fluoride as a reaction catalyst to a sulfuric acid alkylation unit, the method comprising: (a) substituting sulfuric acid for hydrogen fluoride as the reaction catalyst; and (b) providing a sulfuric acid alkylation reactor system or a split sulfuric acid alkylation reactor system as disclosed in this disclosure, wherein a new vessel is provided as the reactor vessel in the sulfuric acid alkylation reactor system or the split sulfuric acid alkylation reactor system. The new vessel can be horizontal or vertical. In some embodiments, a new closed horizontal reactor vessel is provided for the SA alkylation reactor system or the split SA alkylation reactor system. In some embodiments, a new closed vertical reactor vessel is provided for the SA alkylation reactor system.

Figure 13:
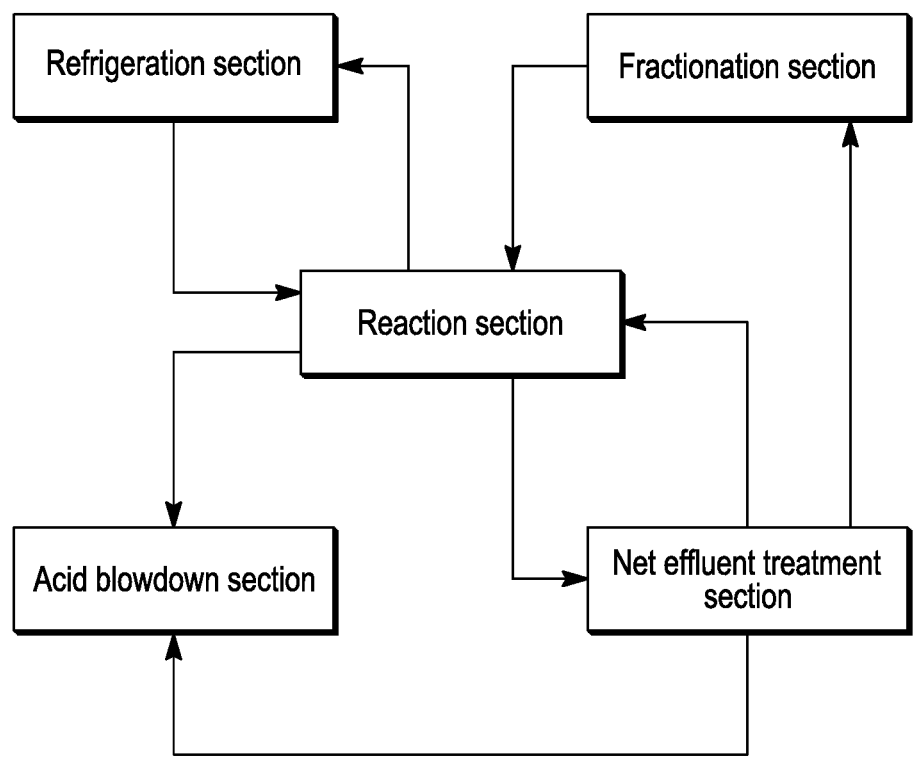
FIG. 13 is a block-flow diagram showing sections of grassroots and/or converted SA alkylation units.

In some embodiments, a converted SA alkylation unit comprises a reaction section, a refrigeration section, a fractionation section, a net effluent treatment section and an acid blowdown section as shown in FIG. 13. The reaction section typically comprises a SA alkylation reactor system or a split SA alkylation reactor system. The refrigeration section helps to keep the reaction temperature low in the reaction section by sending a refrigerant recycle stream comprising isoparaffin reactant back to the reaction section. The fractionation section generates alkylate product and recovers and recycles unreacted isoparaffin reactant to the reaction section. The net effluent treatment section purifies the net effluent stream. The acid blowdown section is used to remove and/or recover residual hydrocarbons from the spent acid before sending the spent acid to storage.

Figure 15:
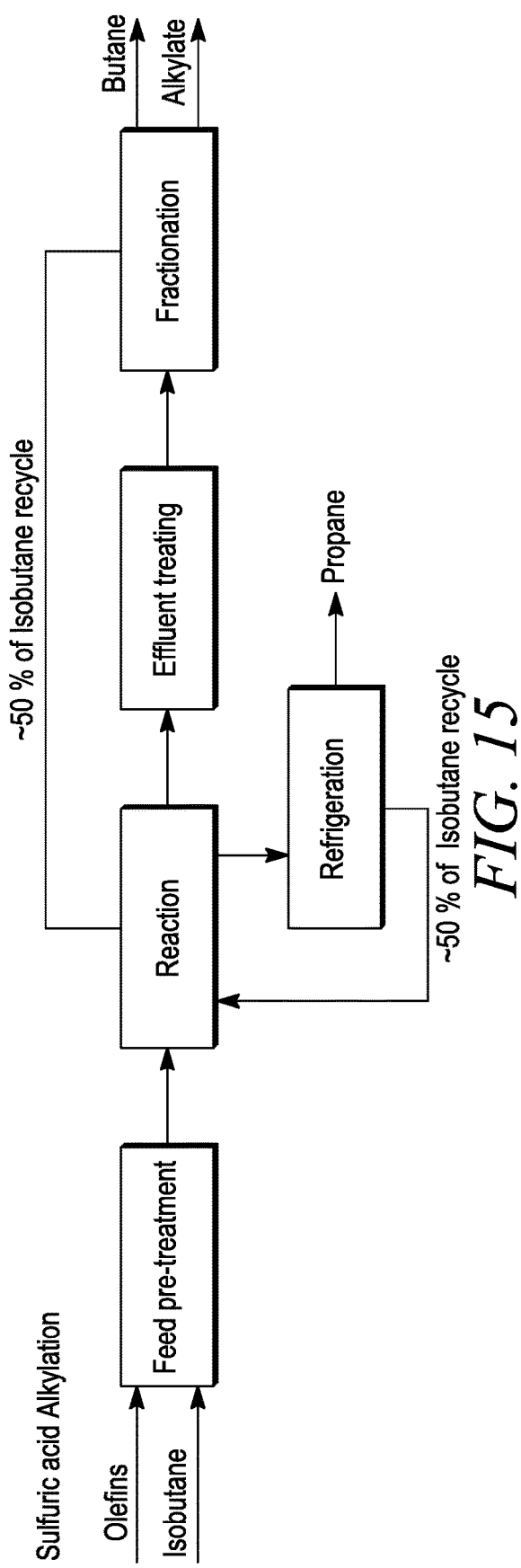
FIG. 15 shows an overall process flow of a converted SA alkylation unit.

An HF alkylation unit comprises an HF alkylation reactor, an HF alkylation fractionation section comprising one or more fractionators, and an HF acid relief neutralizer vessel. In some embodiments, the HF alkylation reactor is decommissioned. In some embodiments, a refrigeration section is added or provided in a converted SA alkylation unit to satisfy the lower reaction temperature requirement comparing with an HF alkylation unit. The refrigeration section is fluidly connected with the reactor vessel in the SA alkylation reactor system to receive the vapor stream (e.g., 31 in FIG. 1) comprising isoparaffin (e.g., isobutane) from the reactor vessel and compresses and condenses the vapor stream to form a refrigerant recycle stream. At least a portion of the refrigerant recycle stream comprising isoparaffin (e.g., isobutane) is recycled to the reactor system (FIG. 15).

The refrigeration section typically comprises a refrigerant compressor and a refrigerant condenser for condensing a vapor stream from the refrigerant compressor. In some embodiments, the refrigeration section further comprises a compressor K/O (knockout) drum upstream of the refrigerant compressor to remove suspended liquid droplets entrained in a vapor stream before the vapor stream is introduced into the refrigerant compressor. In some embodiments, the refrigeration section further comprises a refrigerant accumulator vessel downstream of the refrigerant condenser to collect the refrigerant condensate. In some embodiments, the refrigeration section further comprises a heat exchanger which can be used to cool a liquid stream from the refrigerant accumulator. In some embodiments, the refrigeration section further comprises a refrigerant recycle pump to send the refrigerant recycle stream to the reactor system. In some embodiments, a refrigeration section is added or provided in a converted SA alkylation unit, and the refrigeration section comprises a compressor K/O drum, a refrigerant compressor and a refrigerant condenser for condensing a vapor stream from the refrigerant compressor.

In some embodiments, the equipment or vessel(s) provided in the refrigeration section are new equipment or vessel(s). In some embodiments, a new refrigerant compressor is provided for the refrigeration section in the converted SA alkylation unit. In some embodiments, a new compressor K/O drum is provided for the refrigeration section in the converted SA alkylation unit. In some embodiments, a new refrigerant condenser for condensing a vapor stream from the refrigerant compressor is provided for the refrigeration section in the converted SA alkylation unit. In some embodiments, a new refrigerant recycle pump is provided for the refrigeration section in the converted SA alkylation unit. In some embodiments, a new refrigerant accumulator vessel is provided for the refrigeration section in the converted SA alkylation unit. In some embodiments, a conduit is added to or provided in a converted SA alkylation unit to transport the refrigerant recycle stream from the refrigeration section to the sulfuric acid alkylation reactor system. In some embodiments, a conduit is added to or provided in a converted SA alkylation unit to connect a refrigerant recycle pump with the reactor system.

In some embodiments, the existing HF alkylation unit further comprises a fractionator (e.g., isostripper) receiver acting as a surge drum for the isobutane recycle pump. Such fractionator receiver can be retained or modified to provide a refrigerant accumulator vessel for the refrigeration section in the converted SA alkylation unit.

In some embodiments, the HF alkylation fractionation section is retained or modified to provide a sulfuric acid alkylation fractionation section in a converted SA alkylation unit. In some embodiments, the fractionation section of the existing HF alkylation unit comprises one or more fractionators, and said one or more fractionators are retained to provide one or more fractionators for the fractionation section in the converted SA alkylation unit. In some embodiments, the existing HF alkylation unit comprises a fractionation section comprising a main fractionator and a debutanizer, and in some embodiments, a nozzle is added to the main fractionator above the isobutane fraction outlet for the side draw (where the isobutane fraction exits the fractionation column) to provide a feed stream comprising the refrigerant condensate from the refrigeration section, which allows for a refrigeration system propane purge.

The fractionation section in a converted SA alkylation unit or an existing HF alkylation unit can have several different configurations or designs. In one configuration, the fractionation section comprises a single main fractionator which generates a propane fraction, an isobutane fraction, a normal butane (n-butane) fraction, and an alkylate fraction. In another configuration, the fractionation section comprises two fractionators. The first fractionator (e.g., main fractionator or depropanizer) generates a propane fraction, an isobutane fraction, and a bottom fraction comprising n-butane and alkylate. The bottom fraction is sent to the second fractionator (e.g., debutanizer) which generates a n-butane fraction and an alkylate fraction. In another configuration, the fractionation section comprises two fractionators. The first fractionator (e.g., main fractionator) generates a top fraction comprising propane and isobutane, an isobutane fraction, a n-butane fraction, and an alkylate fraction. The top fraction is sent to the second fractionator (e.g., depropanizer) which generates a propane fraction and an isobutane fraction. In another configuration, the fractionation section comprises two fractionators. The first fractionator (e.g., depropanizer) generates a propane fraction, an isobutane fraction, and a bottom fraction comprising isobutane, n-butane and alkylate. The bottom fraction is sent to the second fractionator (e.g., isostripper) which generates an isobutane fraction, a n-butane fraction and an alkylate fraction. In some embodiments, the HF alkylation fractionation section is retained or modified to provide a sulfuric acid alkylation fractionation section in a converted SA alkylation unit, and the HF alkylation fractionation section and the sulfuric acid alkylation fractionation section have same configuration, that is, the configuration of the HF alkylation fractionation section is retained in the conversion process.

In some embodiments, the HF alkylation unit further comprises a feed dryer, and one or more feed dryers in the existing HF alkylation unit can be retained or modified to provide one or more feed dryers in a converted SA alkylation unit. Feed dryers are used to dry hydrocarbons such as olefin and isoparaffin in hydrocarbon feed streams to an alkylation reactor. In some embodiments, a drying agent such as activated alumina is provided to be used in the feed dryer for the converted SA alkylation unit. The drying agent from an existing HF alkylation unit can be retained, reused or replaced. In some embodiments, one or more feed dryers in an existing HF alkylation unit can be decommissioned.

In some embodiments, the HF alkylation unit further comprises one or more feed coalescers, and said one or more feed coalescers are retained or modified to provide one or more feed coalescers upstream of the one or more feed dryers respectively in a converted SA alkylation unit. The feed coalescers are used to remove suspended water droplets entrained in a hydrocarbon stream. In some embodiments, a coalescing media is provided to be used in a feed coalescer for the converted SA alkylation unit. The coalescing media from an existing HF alkylation unit can be retained, reused or replaced. In some embodiments, one or more feed coalescers in an existing HF alkylation unit can be decommissioned.

In some embodiments, the HF alkylation unit further comprises an HF acid cooler, and the HF acid cooler is decommissioned. In some embodiments, the HF alkylation unit further comprises an HF storage tank under the vertical HF acid settler, and the HF storage tank under the vertical HF acid settler is decommissioned. In some embodiments, the HF alkylation unit further comprises an HF regenerator, and the HF regenerator is decommissioned. In some embodiments, the HF alkylation unit further comprises an HF regenerator condenser, and the HF regenerator condenser is decommissioned. In some embodiments, the HF alkylation unit further comprises an HF regenerator isobutane superheater, and the HF regenerator isobutane superheater is decommissioned. In some embodiments, the HF alkylation unit further comprises an HF regenerator overhead pump, and the HF regenerator overhead pump is decommissioned.

In some embodiments, one or more feed/effluent heat exchangers are added or provided in a converted SA alkylation unit to reduce the temperature of hydrocarbon feed streams and increase the temperature of net effluent streams. In some embodiments, a feed/effluent heat exchanger is located downstream from the feed dryer and upstream of the SA alkylation reactor system with respect to the flow direction of the hydrocarbon feed stream. In some embodiments, one or more new feed/effluent heat exchangers are added or provided in a converted SA alkylation unit. In some embodiments, the feed/effluent heat exchanger is a shell and tube heat exchanger.

A pumped-flow HF alkylation unit (UOP HF alkylation unit) typically comprises one or more HF acid circulation pumps to circulate the HF acid recycle stream within the reaction section. In some embodiments, no HF acid circulation pump is retained from an HF alkylation unit as an emulsion pump for the converted SA alkylation unit. In some embodiments, the one or more HF acid circulation pumps in an existing HF alkylation unit are decommissioned.

Figure 14:
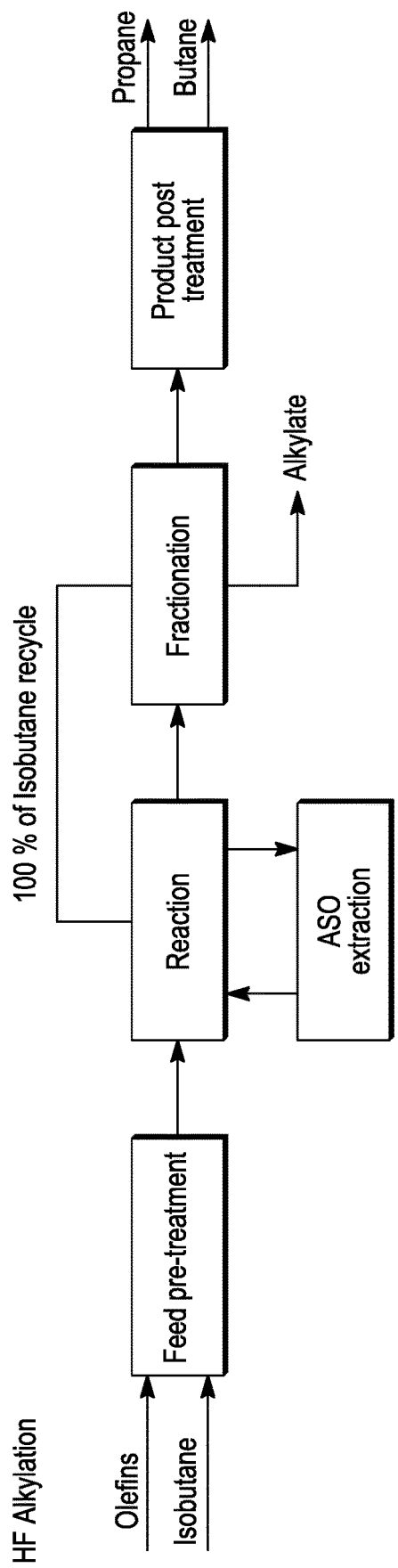
FIG. 14 shows an overall process flow of a HF catalyzed alkylation unit.

In alkylation, a large recycle flow of isobutane to the reaction section is required to promote the desirable alkylation reaction and suppress polymerization reactions that can negatively impact acid consumption and alkylate quality. As shown in FIGS. 14 and 15, in an HF alkylation unit, all of this isobutane recycle flow is from the fractionation section, while in a converted SA alkylation unit, in some embodiments, only about 50% of the isobutane flow is from the fractionation section and the other 50% is from the refrigeration section. Therefore, it is possible to double the effective capacity of the alkylation unit without requiring significant changes to the fractionation section equipment, making the conversion more cost-effective.

In some embodiments, the amount of the isobutane recycled from the refrigeration section to the reaction section in a converted SA alkylation unit is in the range of from about 30% to about 70% comparing with the total amount of isobutane recycled from both the refrigeration section and the fractionation section to the reaction section. In some embodiments, the amount of the isobutane recycled from the refrigeration section to the reaction section in a converted SA alkylation unit is in the range of from about 40% to about 60% comparing with the total amount of isobutane recycled from both the refrigeration section and the fractionation section to the reaction section.

In some embodiments, after converting an HF alkylation unit to a SA alkylation unit, the capacity of the converted SA alkylation unit is increased by at least 50% comparing with the capacity of the HF alkylation unit. In some embodiments, the capacity is increased by at least 75%. In some embodiments, the capacity is increased by at least 100%. In some embodiments, the capacity is increased by at least 125%.

In some embodiments, the HF acid relief neutralizer vessel in an existing HF alkylation unit is retained or modified to provide a blowdown vapor scrubber in a converted SA alkylation unit. The blowdown vapor scrubber in a converted SA alkylation unit is used to neutralize any acidic vapors from the unit before they go to the relief (flare) header to prevent corrosion in the relief (flare) piping. In some embodiments, an aqueous KOH (potassium hydroxide) solution is used in the HF acid relief neutralizer vessel for neutralization, and the conversion method further comprises substituting NaOH (sodium hydroxide) for KOH to be used as a caustic solution in the blowdown vapor scrubber to neutralize acidic vapors.

In some embodiments, the existing HF alkylation unit further comprises an HF alkylation waste treatment system comprising an HF acid neutralization pit, and said HF acid neutralization pit is retained or modified to provide a sulfuric acid neutralization basin in a sulfuric acid alkylation waste treatment system in the converted SA alkylation unit. The sulfuric acid neutralization basin is used to neutralize an acidic hydrocarbon drain or a sulfuric acid drain which may originate from an equipment such as a pump, a heat exchanger, a drum, or a vessel which needs to be drained of acidic hydrocarbon and/or sulfuric acid for maintenance or repair. Typically, a caustic solution (e.g., NaOH) is used as the neutralizing agent. In some embodiments, the caustic solution used in the blowdown vapor scrubber can be shared with the sulfuric acid neutralization basin. In some embodiments, a portion of the caustic solution from the bottom of the blowdown vapor scrubber can be introduced into the sulfuric acid neutralization basin. In some embodiments, the caustic solution is an aqueous NaOH solution. In some embodiments, an aqueous KOH solution is used in the HF acid neutralization pit, and the conversion method further comprises substituting NaOH for KOH to be used in the sulfuric acid neutralization basin to neutralize acidic hydrocarbon and/or sulfuric acid. The term "acidic hydrocarbon", as used herein, means a hydrocarbon stream containing sulfuric acid.

In some embodiments, the existing HF alkylation unit further comprises at least one propane defluorinator, and said at least one propane defluorinator is retained or modified to provide at least one propane purification vessel in the converted SA alkylation unit. In some embodiments, there are two or more propane defluorinators in an existing HF alkylation unit. One of such propane defluorinator can be retained or modified to provide a caustic wash vessel to purify the propane product in the converted SA alkylation unit. In some embodiments, the caustic solution used in the blowdown vapor scrubber can be directed to such caustic wash vessel. Another propane defluorinator can be retained or modified to provide a water wash vessel to purify the propane product in the converted SA alkylation unit. Typically, the water wash vessel is downstream from the caustic wash vessel.

In some embodiments, the existing HF alkylation unit further comprises an HF alkylation propane stripper, and said HF alkylation propane stripper is decommissioned. Typically, an HF alkylation propane stripper is a small reboiled stripping column utilizing steam as the heating medium. It is used to recover HF present in a propane product stream.

In some embodiments, the existing HF alkylation unit further comprises an HF acid recontactor, and said HF acid recontactor is retained or modified to provide a sulfuric acid coalescer (e.g., 1701 in FIG. 21) in the converted SA alkylation unit. The sulfuric acid coalescer is used to remove sulfuric acid from a hydrocarbon stream such as a net effluent. In some embodiments, the sulfuric acid coalescer comprises a coalescing media inside. In some embodiments, the HF acid recontactor is decommissioned.

In some embodiments, the existing HF alkylation unit further comprises a propane KOH treater and/or a n-butane KOH treater, and said propane KOH treater and/or said n-butane KOH treater is retained or modified to provide a net effluent purification vessel for removing sulfur-containing contaminants from the net effluent in the converted SA alkylation unit. In some embodiments, the net effluent purification vessel is a dry alumina adsorption vessel (e.g., 1705 in FIG. 21) containing dry alumina (e.g., activated alumina) to adsorb or remove sulfur-containing contaminants from the net effluent. In some embodiments, the net effluent purification vessel contains a purifying agent comprising an adsorbent selected from the group consisting of alumina, bauxite, aluminosilicate, zeolite, inorganic silicates, zinc oxide, and combinations thereof. In some embodiments, a sulfuric acid coalescer is upstream of the net effluent purification vessel with respect to the net effluent flow direction. In some embodiments, the propane KOH treater is decommissioned. In some embodiments, the n-butane KOH treater is decommissioned. In some embodiments, a new dry alumina adsorption vessel is provided to the converted SA alkylation unit. In some embodiments, the propane KOH treater and/or the n-butane KOH treater in the HF alkylation unit is retained or modified to provide propane treater(s) in the converted SA alkylation unit to purify propane product.

In some embodiments, the existing HF alkylation unit further comprises an alumina treater to remove residual HF acid in the propane product stream and/or the n-butane product stream, and said alumina treater is retained or modified to provide a dry alumina adsorption vessel in the converted SA alkylation unit.

When a dry alumina adsorption vessel containing dry alumina is used to purify the net effluent, the resulting net effluent is dry. The recycle isobutane stream separated out from the dry net effluent in a fractionator is also dry. In such embodiments, a converted SA alkylation unit can operate without feed dryer(s) and/or feed coalescer(s) since a SA alkylation reaction is relatively insensitive to the small amount of water contained in the olefin feed and makeup isobutane. Also in such embodiments, the olefin feed flowrate can be increased for the capacity expansion of the unit without requiring any modification to the existing feed dryer(s). In some embodiments, with a dry recycle isobutane, the existing feed dryer(s) and/or feed coalescer(s) can be decommissioned. In some embodiments, the existing feed dryer(s) and/or feed coalescer(s) can be retained to remove the relatively small amount of water in the olefin feed stream to further decrease the sulfuric acid consumption in the alkylation process.

In some embodiments, the acid settling zone in the sulfuric acid alkylation reactor system is sufficient to separate the hydrocarbon phase from the sulfuric acid phase, and the converted sulfuric acid alkylation unit comprises no sulfuric acid settler other than the acid settling zone inside the reactor system. In some embodiments, the converted SA alkylation unit comprises no sulfuric acid after settler or secondary sulfuric acid settler downstream of the acid settling zone for further separation.

In some embodiments, the existing HF alkylation unit further comprises an ASO/KOH separator, and said ASO/

KOH separator is retained or modified to provide a sulfuric acid blowdown drum (e.g., 1709 in FIG. 21) in the converted SA alkylation unit.

In some embodiments, the existing HF alkylation unit further comprises an ASO washer and an ASO surge drum. The ASO washer washes the acid soluble oil (ASO) with a caustic solution (e.g., an aqueous KOH solution) to neutralize residual HF acid contained therein. The ASO surge drum collects ASO where it is continuously circulated and exported in batch. The ASO needs to be continuously circulated to prevent solidification. In some embodiments, the ASO washer is retained or repurposed as spent acid aftersettler (e.g., 1707 in FIG. 21) in the converted SA alkylation unit to further recover hydrocarbons contained in the spent acid before it is purged. In some embodiments, the ASO surge drum is retained or repurposed as sulfuric acid blowdown drum (e.g., 1709 in FIG. 21) in the converted SA alkylation unit.

Figure 21:
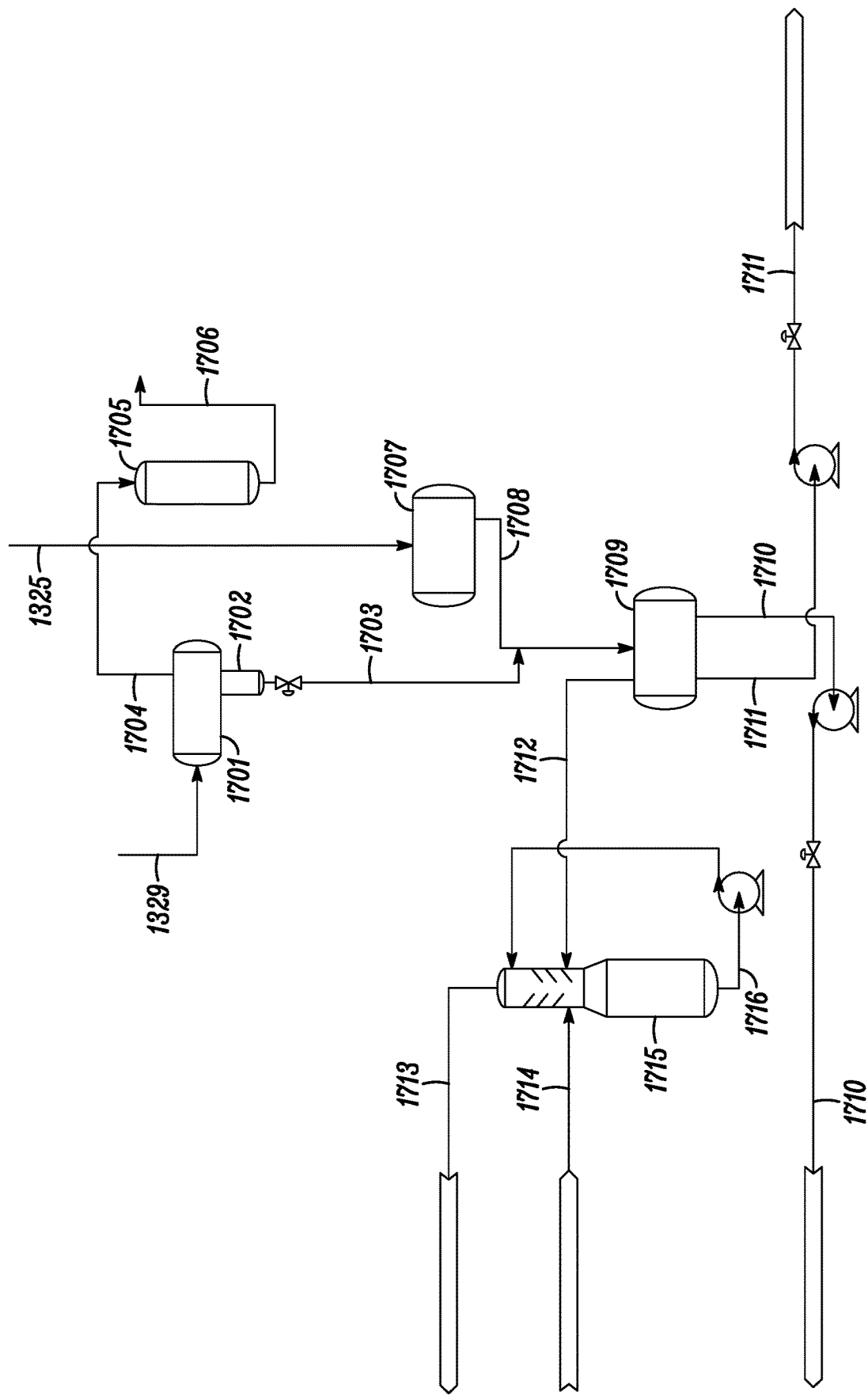
FIG. 21 is a schematic process flow diagram of the net effluent treatment section and the sulfuric acid blowdown section of the converted SA alkylation unit of FIG. 16.
Figure 22:
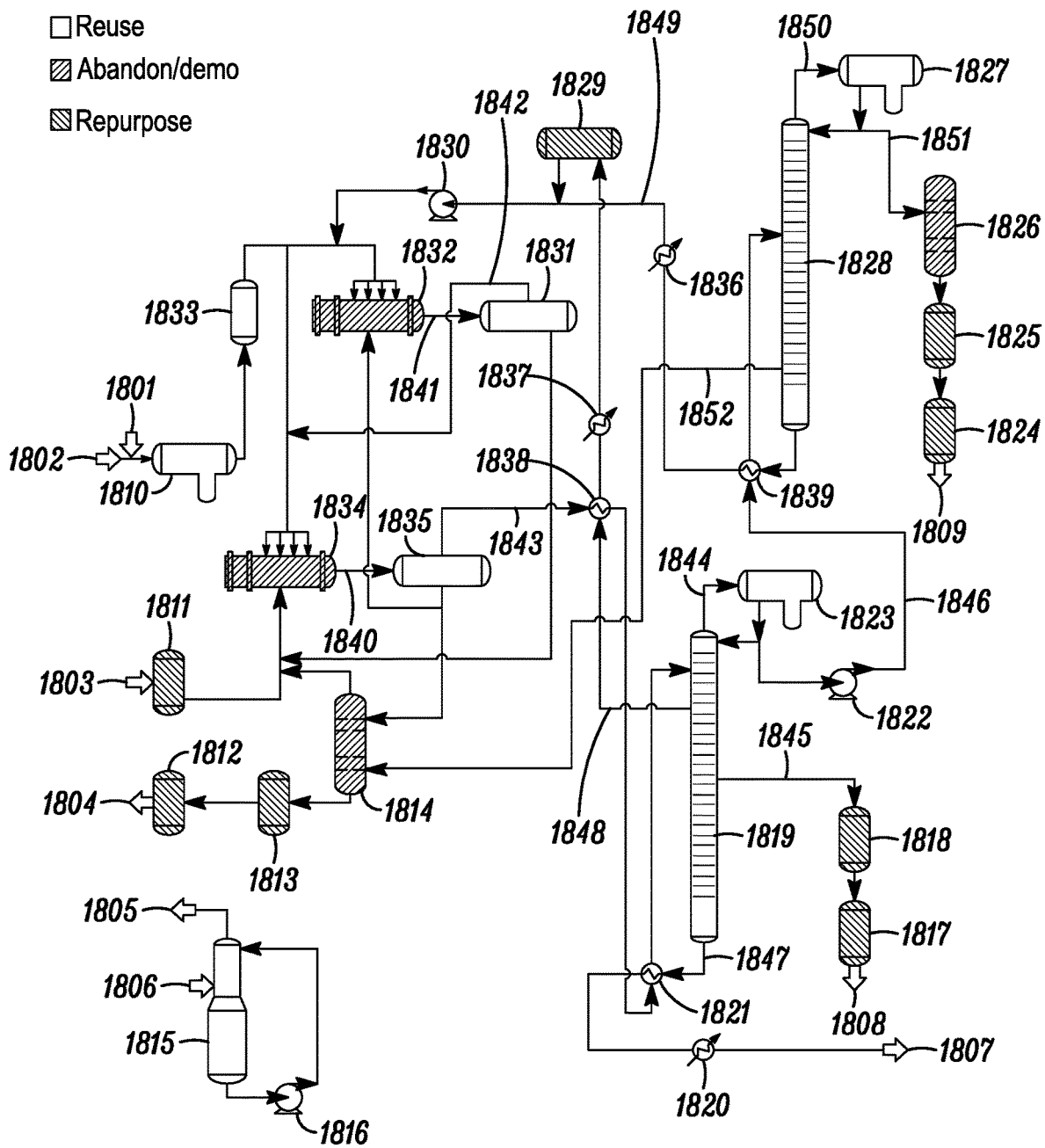
FIG. 22 shows a simplified process flow diagram of an original HF alkylation unit which uses HF as the reaction catalyst to produce alkylate.

In some embodiments, the existing HF alkylation unit further comprises a tar neutralizer (e.g., 1812 in FIG. 22) and a polymer surge drum (e.g., 1813 in FIG. 22). The tar neutralizer neutralizes residual HF acid contained in ASO, and the polymer surge drum collects ASO and sends it to the tar neutralizer. In some embodiments, the tar neutralizer is retained. In some embodiments, the tar neutralizer is retained or repurposed as spent acid aftersettler (e.g., 1707 in FIG. 21) in the converted SA alkylation unit to further recover hydrocarbons contained in the spent acid before it is purged. In some embodiments, the polymer surge drum is retained. In some embodiments, the polymer surge drum is retained or repurposed as acid blowdown drum (e.g., 1709 in FIG. 21) in the converted SA alkylation unit.

In some embodiments, the existing HF alkylation unit further comprises a n-butane defluorinator and/or a propane defluorinator. In some embodiments, the n-butane defluorinator and/or the propane defluorinator is decommissioned. In some embodiments, the n-butane defluorinator and/or the propane defluorinator is retained or modified to provide a net effluent purification vessel (e.g., a dry alumina adsorption vessel) for removing sulfur-containing contaminants from the net effluent in the converted SA alkylation unit.

In some embodiments, the existing HF alkylation unit further comprises KOH regeneration facilities. In some embodiments, the KOH regeneration facilities are decommissioned. In some embodiments, the KOH regeneration facilities are retained or modified to provide NaOH or KOH regeneration facilities in the converted SA alkylation unit.

In some embodiments, the existing HF alkylation unit further comprises at least one ASO neutralization vessel. In some embodiments, the at least one ASO neutralization vessel is decommissioned. In some embodiments, the at least one ASO neutralization vessel comprises one or more static mixer(s) (e.g., the static mixer 1181 in FIG. 12). In some embodiments, the at least one ASO neutralization vessel can be retained or modified to provide one or more propane purification vessel(s) (e.g., an in-line static mixer) in the converted SA alkylation unit. In some embodiments, an ASO neutralization vessel is retained or modified to provide a caustic wash vessel to purify the propane product in the converted SA alkylation unit. In some embodiments, an ASO neutralization vessel is retained or modified to provide a water wash vessel to purify the propane product in the converted SA alkylation unit.

The present disclosure also provides a converted sulfuric acid alkylation unit comprising a sulfuric acid alkylation reactor system or a split sulfuric acid alkylation reactor system as disclosed in this disclosure. In some embodiments, the converted sulfuric acid alkylation unit comprises two or more alkylation reactor systems disposed in sequence, wherein the spent acid solution from at least one non-final alkylation reactor system is sent to the immediately subsequent alkylation reactor system as part or all of the sulfuric acid solution therein. In some embodiments, the spent acid solution from each non-final alkylation reactor system is sent to the immediately subsequent alkylation reactor system as part or all of the sulfuric acid solution therein. Such acid staging process can reduce acid consumption and improve alkylate quality by staging the SA flow through the unit.

A portion of the spent acid solution from the final alkylation reactor system can be sent to the sulfuric acid blowdown section of the converted SA alkylation unit to be purged. Fresh sulfuric acid can be fed into the first alkylation reactor system. In some embodiments, fresh sulfuric acid can be fed into each non-final alkylation reactor system.

The present disclosure further provides an alkylation process performed in a converted sulfuric acid alkylation unit as disclosed in this disclosure. In some embodiments, the converted sulfuric acid alkylation unit comprises two or more alkylation reactor systems disposed in sequence, and the alkylation process comprises directing a portion of the spent acid solution generated in a non-final alkylation reactor system to the immediately subsequent alkylation reactor system as part or all of the sulfuric acid solution therein. In some embodiments, the alkylation process comprises directing a portion of the spent acid solution generated in each non-final alkylation reactor system to the immediately subsequent alkylation reactor system as part or all of the sulfuric acid solution therein.

In some embodiments, the alkylation process comprises directing a portion of the spent acid solution generated in the final alkylation reactor system to the sulfuric acid blowdown section of the converted SA alkylation unit to be purged. In some embodiments, the alkylation process comprises feeding a fresh sulfuric acid into the first alkylation reactor system. In some embodiments, the alkylation process comprises feeding a fresh sulfuric acid into each non-final alkylation reactor system.

DETAILED DESCRIPTION OF THE FIGURES

FIG. 1 shows one embodiment of the reactor system and the associated alkylation process. The reactor system 100 comprises a closed horizontal reactor vessel comprising a shell 11, a vapor outlet 12 equipped with a demister 13, an emulsion outlet 32, a first partition baffle 18, a coalescing media 19, a second partition baffle 22, a spent acid outlet 20, and a net effluent outlet 21. The internal static mixer 14 is composed of two static mixers connected in a head-to-tail fashion. The distributor 15 extends from the internal static mixer 14 substantially along the bottom interior surface of the reactor vessel. Both the internal static mixer 14 and the distributor 15 are located at the lower portion of the reaction zone A.

The outlet end of the external static mixer 16 is directly connected with the inlet end of the internal static mixer 14. The emulsion pump 17 is directly connected with the emulsion outlet 32 and the spent acid pump 34, and the spent acid pump 34 is directly connected with the spent acid outlet 20. The first partition baffle 18, the second partition baffle 22 and the coalescing media 19 respectively extends upwardly from the bottom of the reactor vessel. The coalescing media 19 and the second partition baffle 22 define a reaction zone A, an acid settling zone B, and an effluent zone C inside the reactor vessel.

During an alkylation process, the hydrocarbon feed 23 is fed into the inlet end of the internal static mixer 14. The hydrocarbon feed 23 may comprise olefin, recycled isoparaffin, and optionally makeup isoparaffin. The refrigerant recycle stream 25 comprising isoparaffin can be fed into the inlet end of the external static mixer 16. The spent acid pump 34 sends at least a portion of the spent acid 28 exiting the spent acid outlet 20 to the emulsion pump 17. In some embodiments, a portion of the spent acid 29 can be purged or sent to the acid blowdown section. In some embodiments, in an acid staging process wherein two or more alkylation reactor systems are disposed in sequence, a portion of the spent acid 29 can be sent to an immediately subsequent alkylation reactor system as part or all of the sulfuric acid solution therein. In some embodiments, a fresh acid 27 is directed to the emulsion pump 17 to replenish the consumed sulfuric acid. In some embodiments, in an acid staging process wherein two or more alkylation reactor systems are disposed in sequence, spent acid from an immediately preceding alkylation reactor system can be directed to the emulsion pump 17. A portion of the emulsion 33 exiting the emulsion outlet 32 is recycled through the emulsion pump 17. The emulsion recycle stream 33, fresh acid 27 and spent acid recycle stream 28 are mixed in the emulsion pump 17, and the resulting mixture stream 26 is sent to the external static mixer 16 to be further mixed with the refrigerant recycle stream 25. The resulting mixture stream 24 egressing from the external static mixer 16 is sent to the internal static mixer 14 to be further mixed with the hydrocarbon feed 23 to form an emulsion. The emulsion flows into the distributor 15 and is injected into the reaction zone A through the perforations on the distributor 15 in the form of a plurality of jets. A portion of the emulsion 33 exits the reactor vessel and is recycled. The portion of the emulsion not recycled can flow over the top of the first partition baffle 18 and then pass through the coalescing media 19 moving from the reaction zone A to the acid settling zone B. In the acid settling zone B, the emulsion separates into a sulfuric acid phase at the bottom and a liquid hydrocarbon phase above the sulfuric acid phase. At least a portion of the sulfuric acid phase can be recycled as the spent acid recycle stream 28. In some embodiments, a portion of the sulfuric acid phase can be purged or sent to the acid blowdown section as spent acid 29. The liquid hydrocarbon phase in the acid settling zone B can flow over the top of the second partition baffle 22 to enter the effluent zone C. At least a portion of the liquid hydrocarbon phase in the effluent zone C can leave the reactor vessel through net effluent outlet 21 and be sent to a net effluent treatment section as net effluent stream 30.

During the alkylation process, emulsion in the reaction zone A is partially flashed to generate vapor bubbles which rise to the upper portion of the reaction zone A and form the vapor phase at the upper portion of the reactor vessel. The vapor stream 31 which comprises isoparaffin leaves the reactor vessel through the vapor outlet 12 and is directed to a refrigeration section. In some embodiments, suspended liquid droplets entrained in the vapor stream 31 can be removed by the demister 13.

Figure 2:
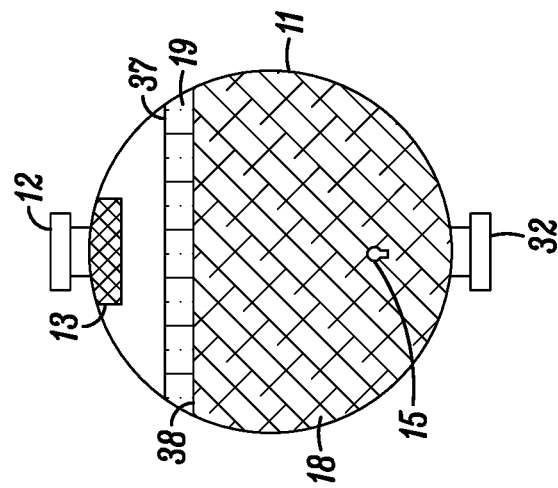
FIG. 2 is a cross-sectional view of the reactor vessel of FIG. 1 taken along the line "X-X" shown in FIG. 1.

FIG. 2 is a cross-sectional view of the reactor vessel of FIG. 1 taken along the line "X-X" shown in FIG. 1. It shows the first partition baffle 18 extending through the shell at the lower portion of the reactor vessel. The first partition baffle 18 is a transverse baffle having a horizontal top 38. The top 38 has a distance below the top interior surface of the reactor vessel.

Figure 3:
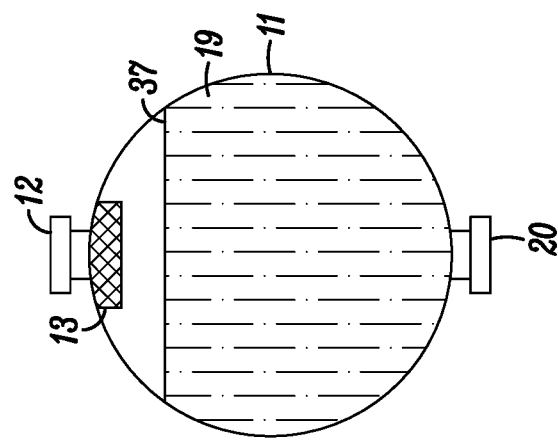
FIG. 3 is a cross-sectional view of the reactor vessel of FIG. 1 taken along the line "Y-Y" shown in FIG. 1.

FIG. 3 is a cross-sectional view of the reactor vessel of FIG. 1 taken along the line "Y-Y" shown in FIG. 1. It shows the coalescing media 19 extending through the shell at the lower portion of the reactor vessel. The coalescing media 19 is a transverse coalescing media having a horizontal top 37. The top 37 has a distance below the top interior surface of the reactor vessel. FIG. 2 shows the top 37 of the coalescing media 19 is at a higher elevation than the top 38 of the first partition baffle 18. In some embodiments, the top 37 of the coalescing media 19 can be at the substantially same elevation as the top 38 of the first partition baffle 18.

Figure 4:
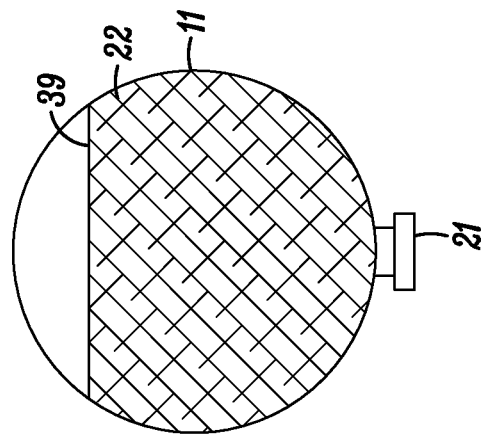
FIG. 4 is a cross-sectional view of the reactor vessel of FIG. 1 taken along the line "Z-Z" shown in FIG. 1.

FIG. 4 is a cross-sectional view of the reactor vessel of FIG. 1 taken along the line "Z-Z" shown in FIG. 1. It shows the second partition baffle 22 extending through the shell at the lower portion of the reactor vessel. The second partition baffle 22 is a transverse baffle having a horizontal top 39. The top 39 has a distance below the top interior surface of the reactor vessel. In some embodiments, the top 39 of the second partition baffle 22 is at the substantially same elevation as the top 38 of the first partition baffle 18. In some embodiments, the top 39 of the second partition baffle 22 is at a lower elevation than the top 38 of the first partition baffle 18.

Figure 5:
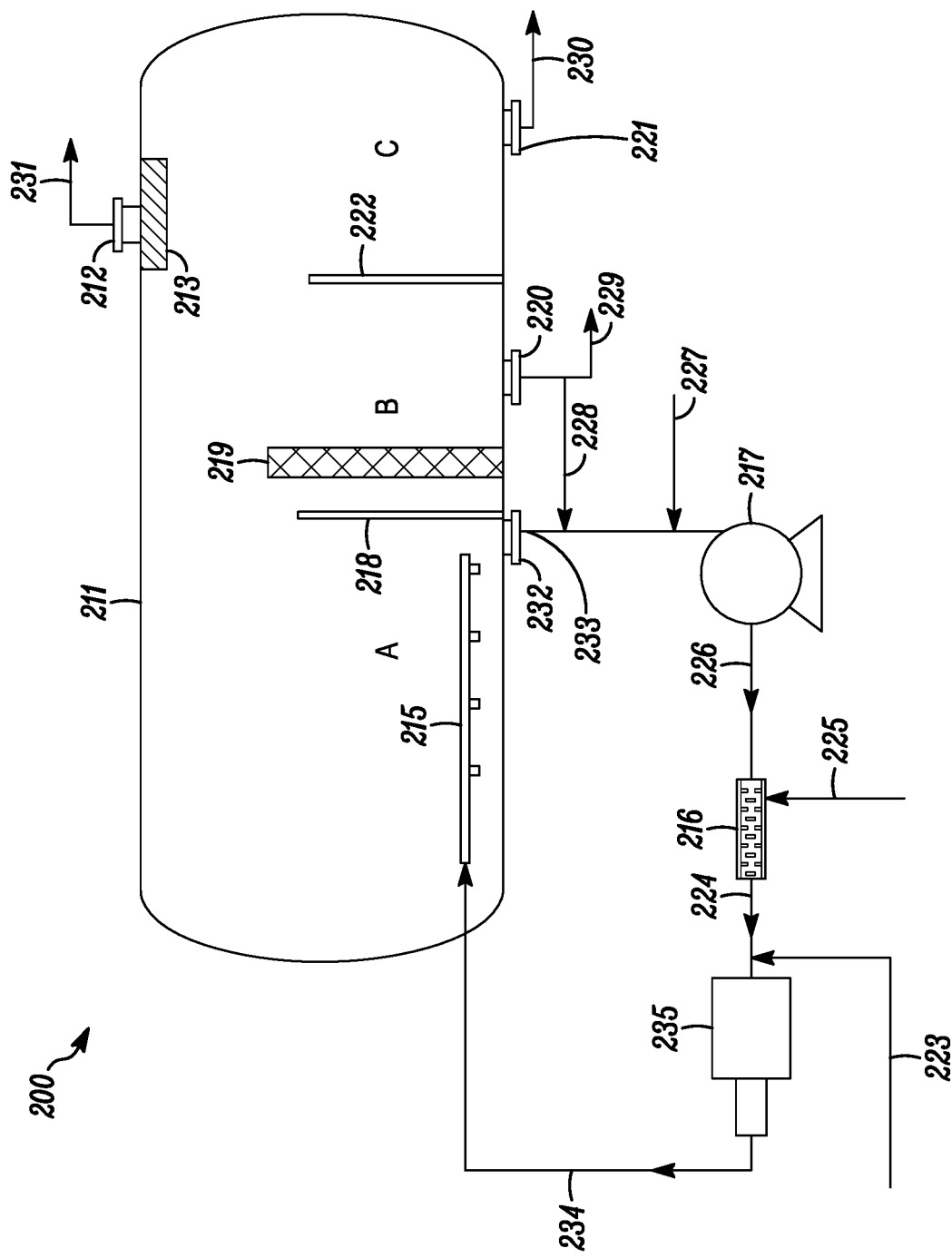
FIG. 5 is a schematic illustration of another sulfuric acid alkylation reactor system with a closed horizontal reactor vessel.

FIG. 5 shows another embodiment of the reactor system and the associated alkylation process. The reactor system 200 comprises a closed horizontal reactor vessel comprising a shell 211, a vapor outlet 212 equipped with a demister 213, an emulsion outlet 232, a first partition baffle 218, a coalescing media 219, a second partition baffle 222, a spent acid outlet 220, and a net effluent outlet 221. The in-line rotor stator mixer 235 is directly connected with the distributor 215 which is located at the lower portion of the reaction zone A and extends along the bottom interior surface of the reactor vessel.

The outlet end of the external static mixer 216 is directly connected with the inlet of the in-line rotor stator mixer 235, and the inlet end of the external static mixer 216 is directly connected with the emulsion pump 217. The emulsion pump 217 is directly connected with the emulsion outlet 232 and the spent acid outlet 220. The first partition baffle 218, the second partition baffle 222 and the coalescing media 219 respectively extends upwardly from the bottom of the reactor vessel. The coalescing media 219 and the second partition baffle 222 define a reaction zone A, an acid settling zone B, and an effluent zone C inside the reactor vessel.

During an alkylation process, the hydrocarbon feed 223 is fed into the connecting conduit between the in-line rotor stator mixer 235 and the external static mixer 216. In some embodiments, the hydrocarbon feed 223 can be fed into the in-line rotor stator mixer 235. The hydrocarbon feed 223 may comprise olefin, recycled isoparaffin, and optionally makeup isoparaffin. The refrigerant recycle stream 225 comprising isoparaffin can be fed into the inlet end of the external static mixer 216. At least a portion of the spent acid 228 exiting the spent acid outlet 220 is sent to the emulsion pump 217. In some embodiments, a portion of the spent acid 229 can be purged or sent to the acid blowdown section. In some embodiments, in an acid staging process wherein two or more alkylation reactor systems are disposed in sequence, a portion of the spent acid 229 can be sent to an immediately subsequent alkylation reactor system as part or all of the sulfuric acid solution therein. In some embodiments, a fresh acid 227 is directed to the emulsion pump 217 to replenish the consumed sulfuric acid. In some embodiments, in an acid staging process wherein two or more alkylation reactor systems are disposed in sequence, spent acid from an immediately preceding alkylation reactor system can be directed to the emulsion pump 217. A portion of the emulsion 233 exiting the emulsion outlet 232 is recycled through the emulsion pump 217. The emulsion recycle stream 233, fresh acid 227 and spent acid recycle stream 228 are mixed in the emulsion pump 217, and the resulting mixture stream 226 is sent to the external static mixer 216 to be further mixed with the refrigerant recycle stream 225. The resulting mixture stream 224 egressing from the external static mixer 216 is sent to the in-line rotor stator mixer 235 to be further mixed with the hydrocarbon feed 223 to form an emulsion. The emulsion 234 flows into the distributor 215 and is injected into the reaction zone A through the perforations on the distributor 215 in the form of a plurality of jets. A portion of the emulsion 233 exits the reactor vessel and is recycled. The portion of the emulsion not recycled can flow over the top of the first partition baffle 218 and then pass through the coalescing media 219 moving from the reaction zone A to the acid settling zone B. In the acid settling zone B, the emulsion separates into a sulfuric acid phase at the bottom and a liquid hydrocarbon phase above the sulfuric acid phase. At least a portion of the sulfuric acid phase can be recycled as the spent acid recycle stream 228. In some embodiments, a portion of the sulfuric acid phase can be purged or sent to the acid blowdown section as waste spent acid 229. The liquid hydrocarbon phase in the acid settling zone B can flow over the top of the second partition baffle 222 to enter the effluent zone C. At least a portion of the liquid hydrocarbon phase in the effluent zone C can leave the reactor vessel through net effluent outlet 221 and be sent to a net effluent treatment section as net effluent stream 230.

During the alkylation process, emulsion in the reaction zone A is partially flashed to generate vapor bubbles which rise to the upper portion of the reaction zone A and form the vapor phase at the upper portion of the reactor vessel. The vapor stream 231 which comprises isoparaffin leaves the reactor vessel through the vapor outlet 212 and is directed to a refrigeration section. In some embodiments, suspended liquid droplets entrained in the vapor stream 231 can be removed by the demister 213.

Figure 6:
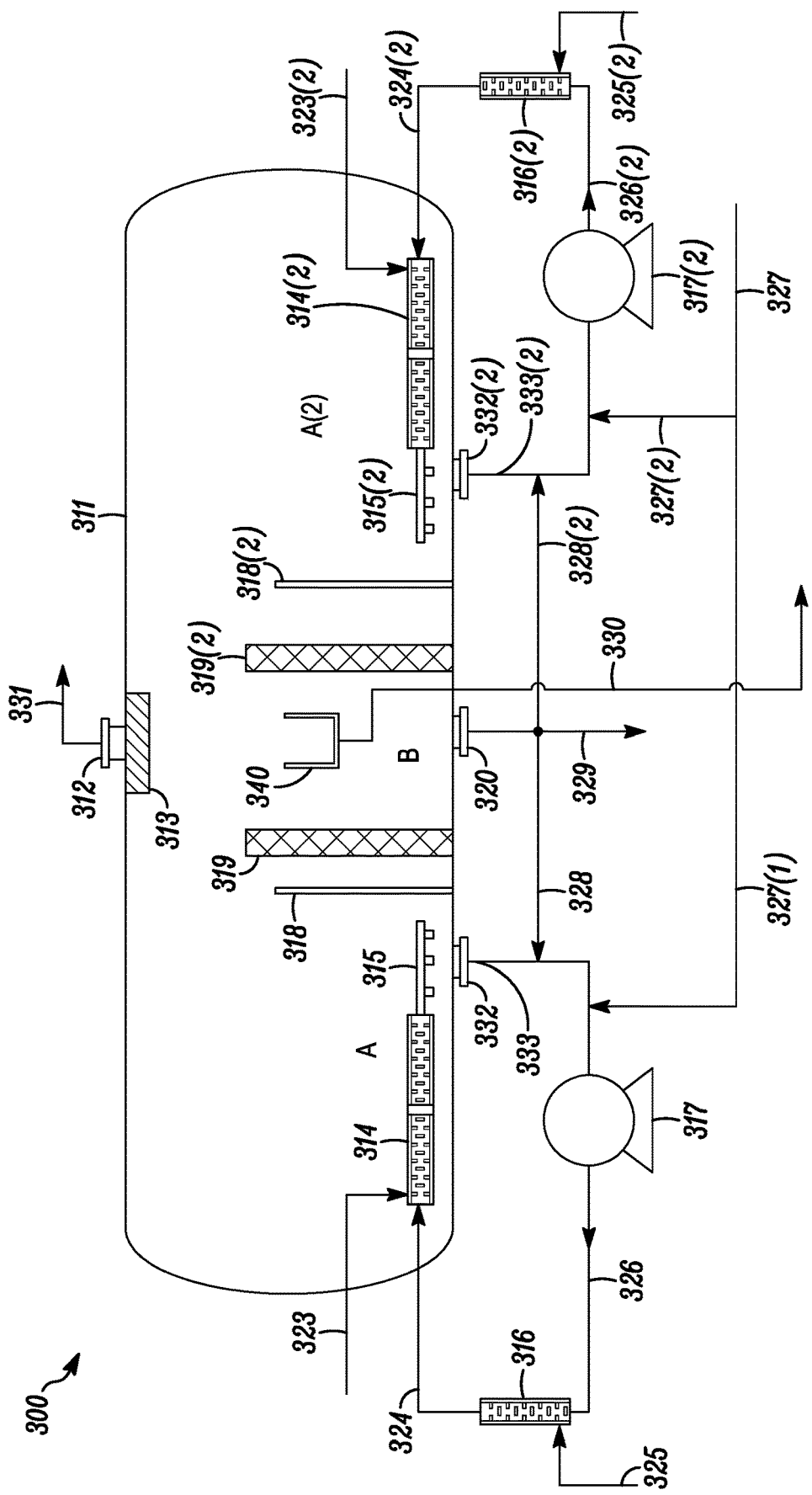
FIG. 6 is a schematic illustration of another sulfuric acid alkylation reactor system with a closed split horizontal reactor vessel.

FIG. 6 shows one embodiment of the split reactor system and the associated alkylation process. The reactor system 300 comprises a closed horizontal reactor vessel comprising a shell 311, a vapor outlet 312 equipped with a demister 313, a first emulsion outlet 332, a second emulsion outlet 332(2), a first partition baffle 318, a first coalescing media 319, a second partition baffle 318(2), a second coalescing media 319(2), and a spent acid outlet 320. The first internal static mixer 314 is composed of two static mixers connected in a head-to-tail fashion. The first distributor 315 extends from the first internal static mixer 314 substantially along the bottom interior surface of the reactor vessel. Both the first internal static mixer 314 and the first distributor 315 are located at the lower portion of the first reaction zone A. The second internal static mixer 314(2) is composed of two static mixers connected in a head-to-tail fashion. The second distributor 315(2) extends from the second internal static mixer 314(2) substantially along the bottom interior surface of the reactor vessel. Both the second internal static mixer 314(2) and the second distributor 315(2) are located at the lower portion of the second reaction zone A(2).

The outlet end of the first external static mixer 316 is directly connected with the inlet end of the first internal static mixer 314. The first emulsion pump 317 is directly connected with the first emulsion outlet 332 and the spent acid outlet 320. The outlet end of the second external static mixer 316(2) is directly connected with the inlet end of the second internal static mixer 314(2). The second emulsion pump 317(2) is directly connected with the second emulsion outlet 332(2) and the spent acid outlet 320. The first partition baffle 318, the first coalescing media 319, the second partition baffle 318(2) and the second coalescing media 319(2) respectively extends upwardly from the bottom of the reactor vessel. The first coalescing media 319 and the second coalescing media 319(2) define a first reaction zone A, an acid settling zone B, and a second reaction zone A(2). In some embodiments, the reactor system further comprises a raised sump 340 having an open top and an outlet.

During an alkylation process, on one side of the split reactor system, the first hydrocarbon feed 323 is fed into the inlet end of the first internal static mixer 314. The first hydrocarbon feed 323 may comprise a first olefin, a first recycled isoparaffin, and optionally a first makeup isoparaffin. The first refrigerant recycle stream 325 comprising isoparaffin can be fed into the inlet end of the first external static mixer 316. Spent acid exiting the spent acid outlet 320 can be split into a first spent acid 328 and a second spent acid 328(2). The first spent acid 328 is sent to the first emulsion pump 317. In some embodiments, a portion of the spent acid 329 can be purged or sent to the acid blowdown section. In some embodiments, in an acid staging process wherein two or more alkylation reactor systems are disposed in sequence, a portion of the spent acid 329 can be sent to an immediately subsequent alkylation reactor system as part or all of the sulfuric acid solution therein. Fresh acid 327 can be split into two portions. One portion is the first fresh acid 327(1) which is directed to the first emulsion pump 317 to replenish the consumed sulfuric acid. A portion of the first emulsion 333 exiting the first emulsion outlet 332 is recycled through the first emulsion pump 317. The first emulsion recycle stream 333, first fresh acid 327(1) and first spent acid recycle stream 328 are mixed in the first emulsion pump 317, and the resulting mixture stream 326 is sent to the first external static mixer 316 to be further mixed with the first refrigerant recycle stream 325. The resulting mixture stream 324 egressing from the first external static mixer 316 is sent to the first internal static mixer 314 to be further mixed with the first hydrocarbon feed 323 to form the first emulsion. The first emulsion flows into the first distributor 315 and is injected into the first reaction zone A through the perforations on the first distributor 315 in the form of a plurality of jets. A portion of the first emulsion 333 exits the reactor vessel and is recycled. The portion of the first emulsion not recycled can flow over the top of the first partition baffle 318 and then pass through the first coalescing media 319 moving from the first reaction zone A to the acid settling zone B. In the acid settling zone B, the first emulsion separates into a first sulfuric acid phase at the bottom and a first liquid hydrocarbon phase above the first sulfuric acid phase. In some embodiments, in an acid staging process wherein two or more alkylation reactor systems are disposed in sequence, spent acid from an immediately preceding alkylation reactor system can be directed to the first emulsion pump 317.

On the other side of the split reactor system, the second hydrocarbon feed 323(2) is fed into the inlet end of the second internal static mixer 314(2). The second hydrocarbon feed 323(2) may comprise a second olefin, a second recycled isoparaffin, and optionally a second makeup isoparaffin. The second refrigerant recycle stream 325(2) comprising isoparaffin can be fed into the inlet end of the second external static mixer 316(2). The second spent acid 328(2) is sent to the second emulsion pump 317(2). The second fresh acid 327(2)

is directed to the second emulsion pump 317(2) to replenish the consumed sulfuric acid. A portion of the second emulsion 333(2) exiting the second emulsion outlet 332(2) is recycled through the second emulsion pump 317(2). The second emulsion recycle stream 333(2), second fresh acid 327(2) and second spent acid recycle stream 328(2) are mixed in the second emulsion pump 317(2), and the resulting mixture stream 326(2) is sent to the second external static mixer 316(2) to be further mixed with the second refrigerant recycle stream 325(2). The resulting mixture stream 324(2) egressing from the second external static mixer 316(2) is sent to the second internal static mixer 314(2) to be further mixed with the second hydrocarbon feed 323(2) to form the second emulsion. The second emulsion flows into the second distributor 315(2) and is injected into the second reaction zone A(2) through the perforations on the second distributor 315(2) in the form of a plurality of jets. A portion of the second emulsion 333(2) exits the reactor vessel and is recycled. The portion of the second emulsion not recycled can flow over the top of the second partition baffle 318(2) and then pass through the second coalescing media 319(2) moving from the second reaction zone A(2) to the acid settling zone B. In the acid settling zone B, the second emulsion separates into a second sulfuric acid phase at the bottom and a second liquid hydrocarbon phase above the second sulfuric acid phase. The first sulfuric acid phase and the second sulfuric acid phase are mixed to form the sulfuric acid phase in the acid settling zone B. The first liquid hydrocarbon phase and the second liquid hydrocarbon phase are mixed to form the liquid hydrocarbon phase in the acid settling zone B. In some embodiments, in an acid staging process wherein two or more alkylation reactor systems are disposed in sequence, spent acid from an immediately preceding alkylation reactor system can be directed to the second emulsion pump 317(2).

In some embodiments, the reactor system comprises a raised sump 340 inside the reactor vessel. The raised sump 340 has an open top and an outlet. The liquid hydrocarbon phase in the acid settling zone B can flow over the top of the raised sump 340 to enter the raised sump 340. Typically, the top of the raised sump 340 is just below the liquid level of the hydrocarbon phase. In some embodiments, the outlet of the raised sump 340 is directly connected with a net effluent outlet (not shown), and at least a portion of the liquid hydrocarbon phase collected in the raised sump 340 can leave the reactor vessel through the net effluent outlet (not shown) and be sent to a net effluent treatment section as net effluent stream 330.

During the alkylation process, the first emulsion in the first reaction zone A and the second emulsion in the second reaction zone A(2) are respectively partially flashed to generate vapor bubbles which rise to the upper portion of the reaction zones and form the vapor phase at the upper portion of the reactor vessel. The vapor stream 331 which comprises isoparaffin leaves the reactor vessel through the vapor outlet 312 and is directed to a refrigeration section. In some embodiments, suspended liquid droplets entrained in the vapor stream 331 can be removed by the demister 313.

Figure 7:
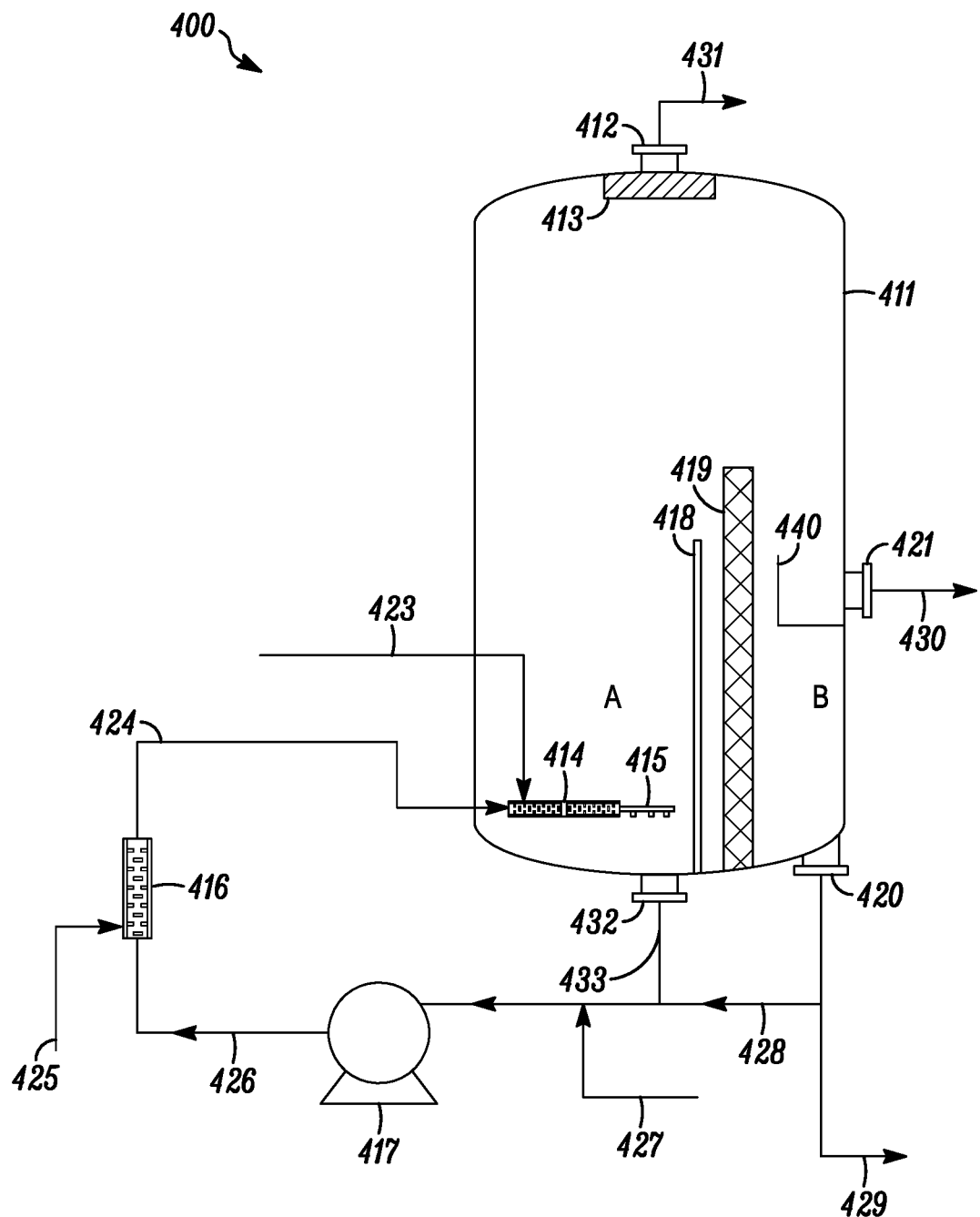
FIG. 7 is a schematic illustration of another sulfuric acid alkylation reactor system with a closed vertical reactor vessel.

FIG. 7 shows another embodiment of the reactor system and the associated alkylation process. The reactor system 400 comprises a closed vertical reactor vessel comprising a shell 411, a vapor outlet 412 equipped with a demister 413, an emulsion outlet 432, a partition baffle 418, a coalescing media 419, a spent acid outlet 420, and a net effluent outlet 421. The internal static mixer 414 is composed of two static mixers connected in a head-to-tail fashion. The distributor 415 extends from the internal static mixer 414 substantially along the bottom interior surface of the reactor vessel. Both the internal static mixer 414 and the distributor 415 are located at the lower portion of the reaction zone A.

The outlet end of the external static mixer 416 is directly connected with the inlet end of the internal static mixer 414. The emulsion pump 417 is directly connected with the emulsion outlet 432 and the spent acid outlet 420. The partition baffle 418 and the coalescing media 419 respectively extends upwardly from the bottom of the reactor vessel. The coalescing media 419 defines a reaction zone A and an acid settling zone B inside the reactor vessel.

During an alkylation process, the hydrocarbon feed 423 is fed into the inlet end of the internal static mixer 414. The hydrocarbon feed 423 may comprise olefin, recycled isoparaffin, and optionally makeup isoparaffin. The refrigerant recycle stream 425 comprising isoparaffin can be fed into the inlet end of the external static mixer 416. At least a portion of the spent acid 428 exiting the spent acid outlet 420 is sent to the emulsion pump 417. In some embodiments, a portion of the spent acid 429 can be purged or sent to the acid blowdown section. In some embodiments, in an acid staging process wherein two or more alkylation reactor systems are disposed in sequence, a portion of the spent acid 429 can be sent to an immediately subsequent alkylation reactor system as part or all of the sulfuric acid solution therein. In some embodiments, a fresh acid 427 is directed to the emulsion pump 417 to replenish the consumed sulfuric acid. In some embodiments, in an acid staging process wherein two or more alkylation reactor systems are disposed in sequence, spent acid from an immediately preceding alkylation reactor system can be directed to the emulsion pump 417. A portion of the emulsion 433 exiting the emulsion outlet 432 is recycled through the emulsion pump 417. The emulsion recycle stream 433, fresh acid 427 and spent acid recycle stream 428 are mixed in the emulsion pump 417, and the resulting mixture stream 426 is sent to the external static mixer 416 to be further mixed with the refrigerant recycle stream 425. The resulting mixture stream 424 egressing from the external static mixer 416 is sent to the internal static mixer 414 to be further mixed with the hydrocarbon feed 423 to form an emulsion. The emulsion flows into the distributor 415 and is injected into the reaction zone A through the perforations on the distributor 415 in the form of a plurality of jets. A portion of the emulsion 433 exits the reactor vessel and is recycled. The portion of the emulsion not recycled can flow over the top of the partition baffle 418 and then pass through the coalescing media 419 moving from the reaction zone A to the acid settling zone B. In the acid settling zone B, the emulsion separates into a sulfuric acid phase at the bottom and a liquid hydrocarbon phase above the sulfuric acid phase. At least a portion of the sulfuric acid phase can be recycled as the spent acid recycle stream 428. In some embodiments, a portion of the sulfuric acid phase can be purged or sent to the acid blowdown section as waste spent acid 429.

In some embodiments, the reactor system comprises a raised sump 440 inside the reactor vessel. The raised sump 440 has an open top and an outlet. The liquid hydrocarbon phase in the acid settling zone B can flow over the top of the raised sump 440 to enter the raised sump 440. Typically, the top of the raised sump 440 is just below the liquid level of the hydrocarbon phase in the acid settling zone B. In some embodiments, the outlet of the raised sump 440 is the net effluent outlet 421, and at least a portion of the liquid hydrocarbon phase collected in the raised sump 440 can leave the reactor vessel through the net effluent outlet 421 and be sent to a net effluent treatment section as net effluent stream 430.

During the alkylation process, emulsion in the reaction zone A is partially flashed to generate vapor bubbles which rise to the upper portion of the reaction zone A and form the vapor phase at the upper portion of the reactor vessel. The vapor stream 431 which comprises isoparaffin leaves the reactor vessel through the vapor outlet 412 and is directed to a refrigeration section. In some embodiments, suspended liquid droplets entrained in the vapor stream 431 can be removed by the demister 413.

Figure 8:
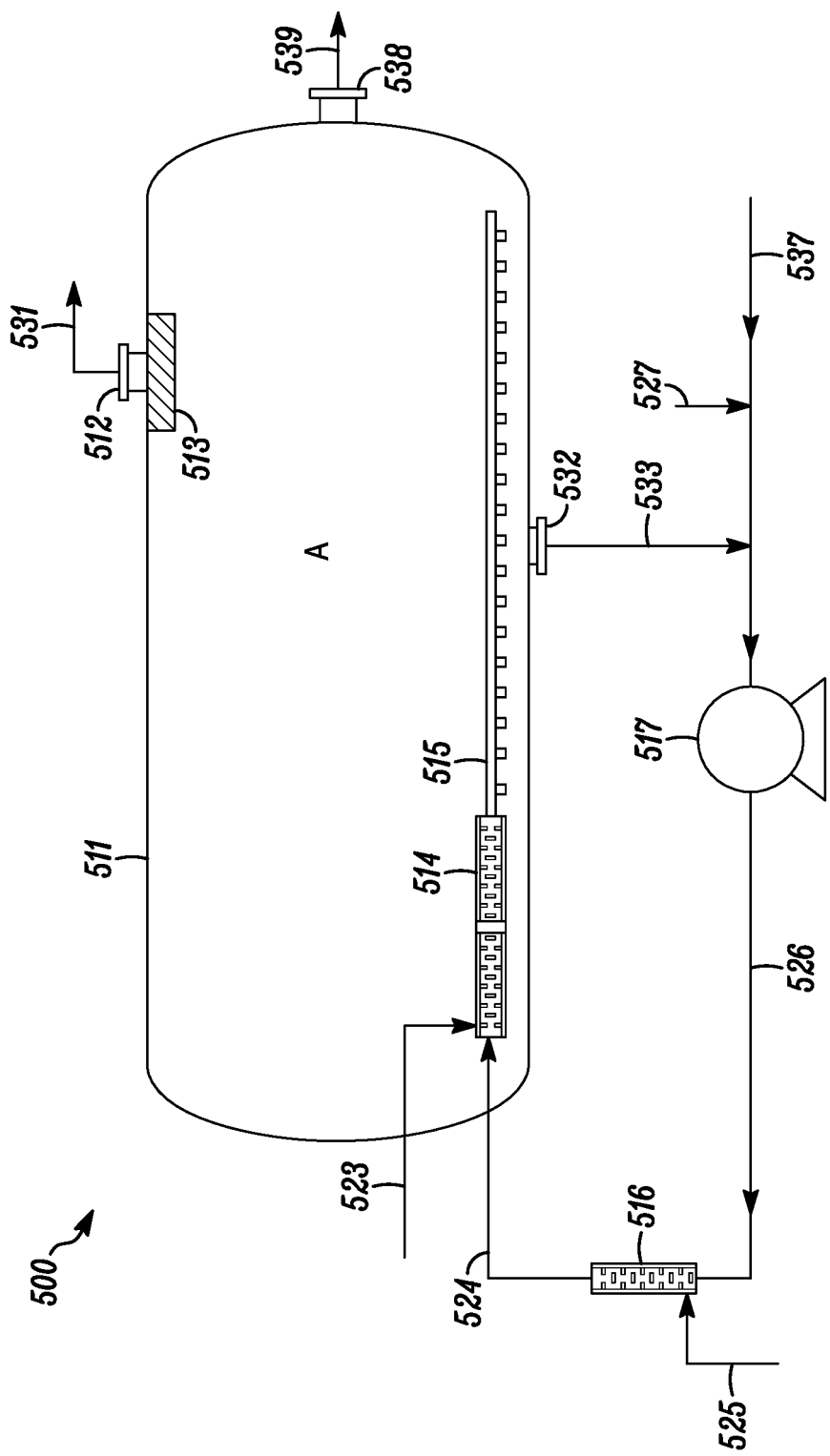
FIG. 8 is a schematic illustration of another sulfuric acid alkylation reactor system with a closed horizontal reactor vessel.

FIG. 8 shows another embodiment of the reactor system and the associated alkylation process. The reactor system 500 comprises a closed horizontal reactor vessel comprising a shell 511, a vapor outlet 512 equipped with a demister 513, a first emulsion outlet 532 and a second emulsion outlet 538. The internal static mixer 514 is composed of two static mixers connected in a head-to-tail fashion. The distributor 515 extends from the internal static mixer 514 substantially along the bottom interior surface of the reactor vessel. Both the internal static mixer 514 and the distributor 515 are located at the lower portion of the reaction zone A. The outlet end of the external static mixer 516 is directly connected with the inlet end of the internal static mixer 514. The emulsion pump 517 is directly connected with the first emulsion outlet 532. In some embodiments, there can be two or more first emulsion outlets 532 along the bottom of the reactor vessel, and the emulsion pump 517 is directly connected with each of them.

During an alkylation process, the hydrocarbon feed 523 is fed into the inlet end of the internal static mixer 514. The hydrocarbon feed 523 may comprise olefin, recycled isoparaffin, and optionally makeup isoparaffin. The refrigerant recycle stream 525 comprising isoparaffin can be fed into the inlet end of the external static mixer 516. A portion of the emulsion 533 exiting the first emulsion outlet 532 is recycled through the emulsion pump 517. The portion of the emulsion not recycled can exit the reactor vessel through the second emulsion outlet 538 and be sent to a sulfuric acid settler outside the reactor vessel wherein the emulsion is separated into a liquid hydrocarbon phase and a sulfuric acid phase (i.e., spent acid). The sulfuric acid phase (i.e., spent acid) can be sent back to the emulsion pump 517 as a spent acid recycle stream 537. In some embodiments, in an acid staging process wherein two or more alkylation reactor systems are disposed in sequence, a portion of the sulfuric acid phase (i.e., spent acid) can be sent to an immediately subsequent alkylation reactor system as part or all of the sulfuric acid solution therein.

In some embodiments, a fresh acid 527 is directed to the emulsion pump 517 to replenish the consumed sulfuric acid. In some embodiments, in an acid staging process wherein two or more alkylation reactor systems are disposed in sequence, spent acid from an immediately preceding alkylation reactor system can be directed to the emulsion pump 517. The emulsion recycle stream 533, fresh acid 527 and spent acid recycle stream 537 are mixed in the emulsion pump 517, and the resulting mixture stream 526 is sent to the external static mixer 516 to be further mixed with the refrigerant recycle stream 525. The resulting mixture stream 524 egressing from the external static mixer 516 is sent to the internal static mixer 514 to be further mixed with the hydrocarbon feed 523 to form an emulsion. The emulsion flows into the distributor 515 and is injected into the reaction zone A through the perforations on the distributor 515 in the form of a plurality of jets.

During the alkylation process, emulsion in the reaction zone A is partially flashed to generate vapor bubbles which rise to the upper portion of the reactor vessel to form a vapor phase there. The vapor stream 531 which comprises isoparaffin leaves the reactor vessel through the vapor outlet 512 and is directed to a refrigeration section. In some embodiments, suspended liquid droplets entrained in the vapor stream 531 can be removed by the demister 513.

Figure 9:
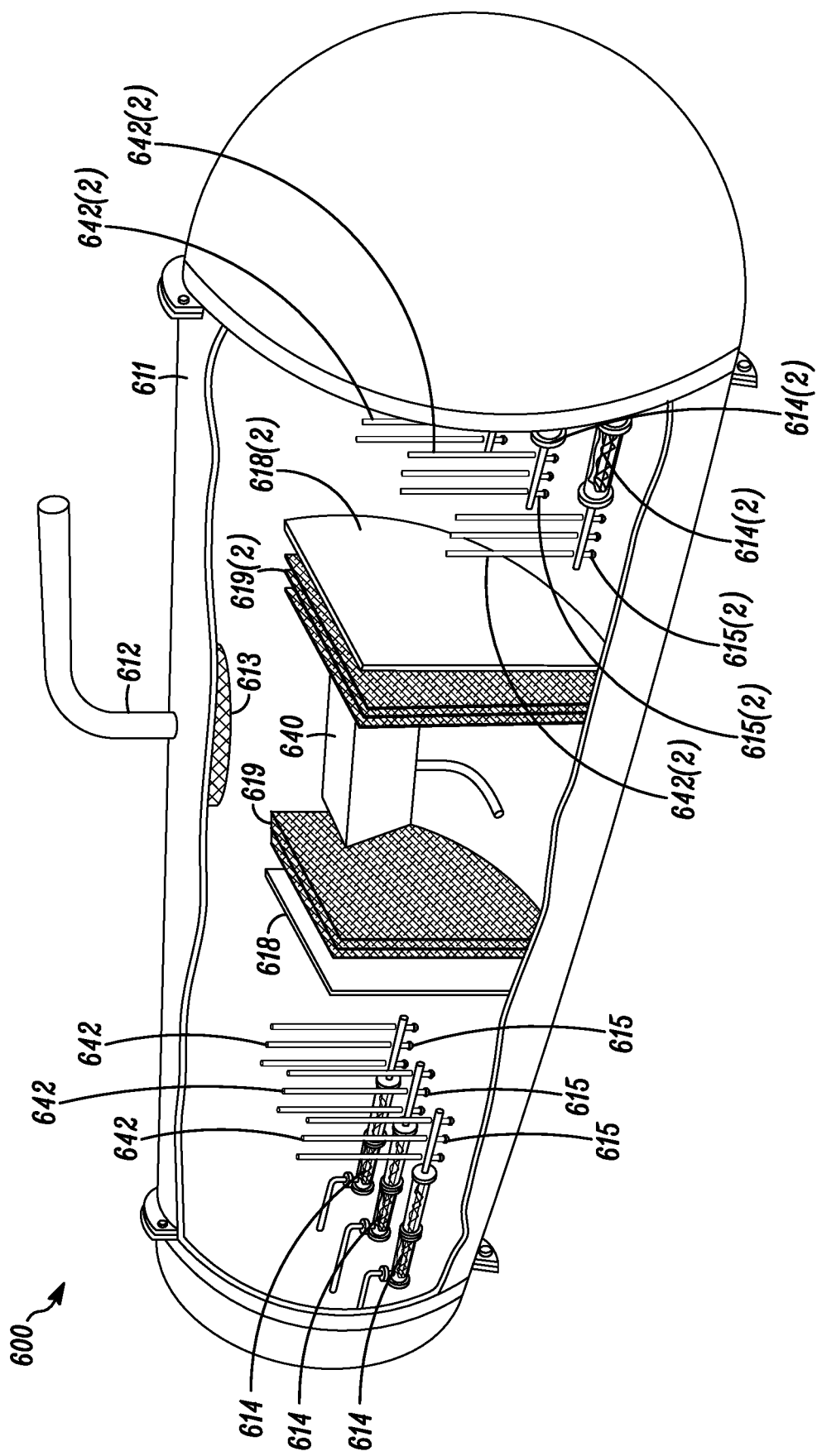
FIG. 9 is a perspective of a closed split horizontal reactor vessel.

FIG. 9 is a perspective of a closed split horizontal reactor vessel. The reactor system 600 comprises a closed horizontal reactor vessel comprising a shell 611, a vapor outlet 612 equipped with a demister 613, a first partition baffle 618, a first coalescing media 619, a second partition baffle 618(2), and a second coalescing media 619(2). There are three sets of first internal static mixers 614 and first distributors 615 at one side of the reactor vessel, each set has one internal static mixer and one distributor directly connected with each other. There are three sets of first draft tubes 642 extending upwardly from above the three first distributors 615 respectively. There are also three sets of second internal static mixers 614(2) and second distributors 615(2) at the other side of the reactor vessel, each set has one internal static mixer and one distributor directly connected with each other. There are three sets of second draft tubes 642(2) extending upwardly from above the three second distributors 615(2) respectively.

The first partition baffle 618, the first coalescing media 619, the second partition baffle 618(2) and the second coalescing media 619(2) respectively extends upwardly from the bottom of the reactor vessel. They all respectively extend through the shell at the lower portion of the reactor vessel. The first partition baffle 618 and the second partition baffle 618(2) are transverse baffles having horizontal tops respectively. The tops respectively have a distance below the top interior surface of the reactor vessel. The first coalescing media 619 and the second coalescing media 619(2) are transverse coalescing media having horizontal tops respectively. The tops also respectively have a distance below the top interior surface of the reactor vessel. The reactor system also comprises a raised sump 640 at the acid settling zone between the first coalescing media 619 and the second coalescing media 619(2). The raised sump 640 has an open top and an outlet.

Figure 10:
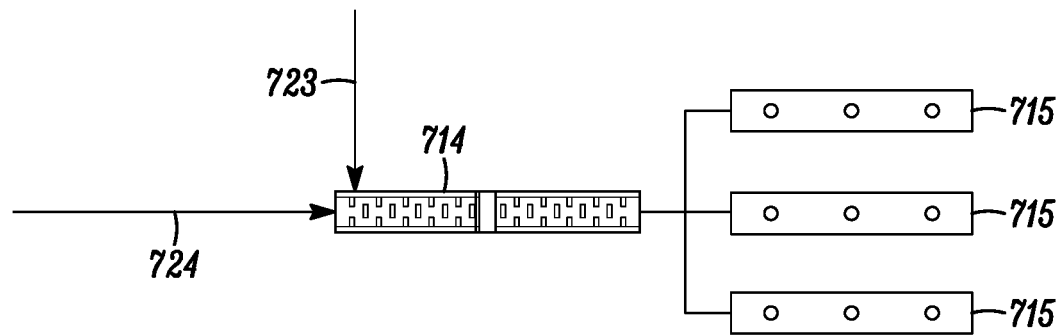
FIG. 10 shows a combination of one internal static mixer with three distributors.

FIG. 10 shows one internal static mixer 714 is directly connected with three distributors 715 through connecting conduits. The internal static mixer 714 is composed of two static mixers connected in a head-to-tail fashion. In some embodiments, the three distributors 715 can be mounted directly on the outlet end of the internal static mixer 714. This internal static mixer/distributor combination can be installed in a reactor vessel or at one side of the split reactor vessel. During an alkylation process, the hydrocarbon feed 723 and the mixture stream 724 from an external static mixer (not shown) can be mixed in the internal static mixer 714 to form an emulsion. The resulting emulsion can be fed into the distributors 715 and injected into a reactor vessel (not shown).

Figure 11:
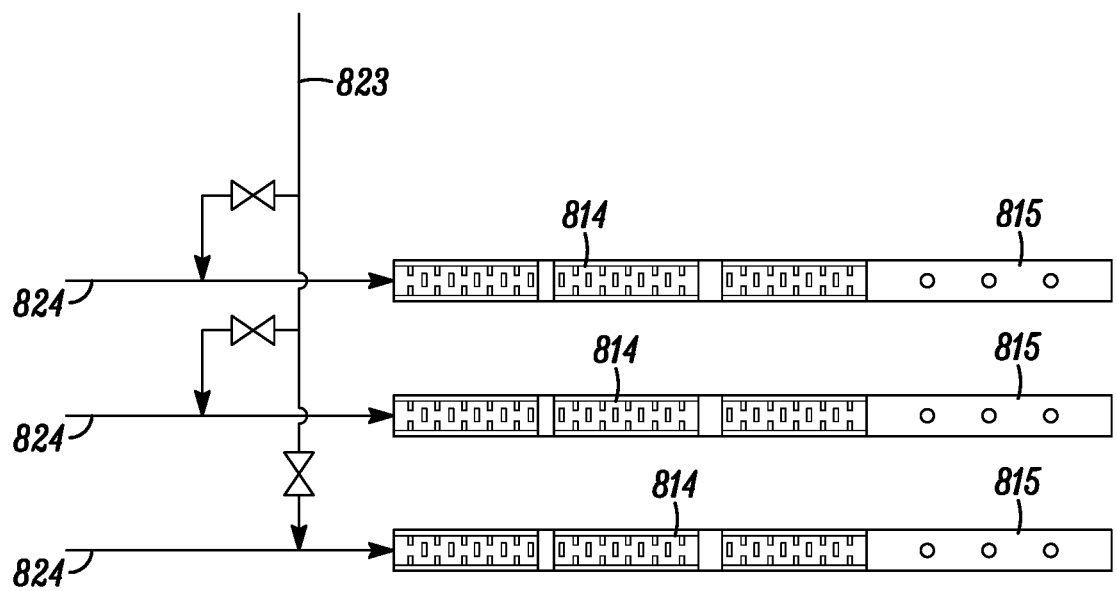
FIG. 11 shows three sets of internal static mixer and distributor.

FIG. 11 shows three sets of internal static mixers 814 and distributors 815. Each of the internal static mixer 814 is composed of three static mixers connected in a head-to-tail fashion. The three distributors 815 are mounted on the outlet end of the three internal static mixers 814 respectively. Such three sets of internal static mixer/distributor combination can be installed in a reactor vessel or at one side of the split reactor vessel. During an alkylation process, the hydrocarbon feed 823 is split into three portions to be fed into the three internal static mixers 814 respectively. In some embodiments, each set of internal static mixer 814 and distributor 815 is directly connected with a different external static mixer (not shown), and the mixture streams 824 from the three external static mixers can be mixed with the three hydrocarbon feeds 823 respectively in the three internal static mixers 814 to form three emulsions. The three emulsions can be fed into the three distributors 815 and injected into a reactor vessel (not shown) respectively.

Figure 12:
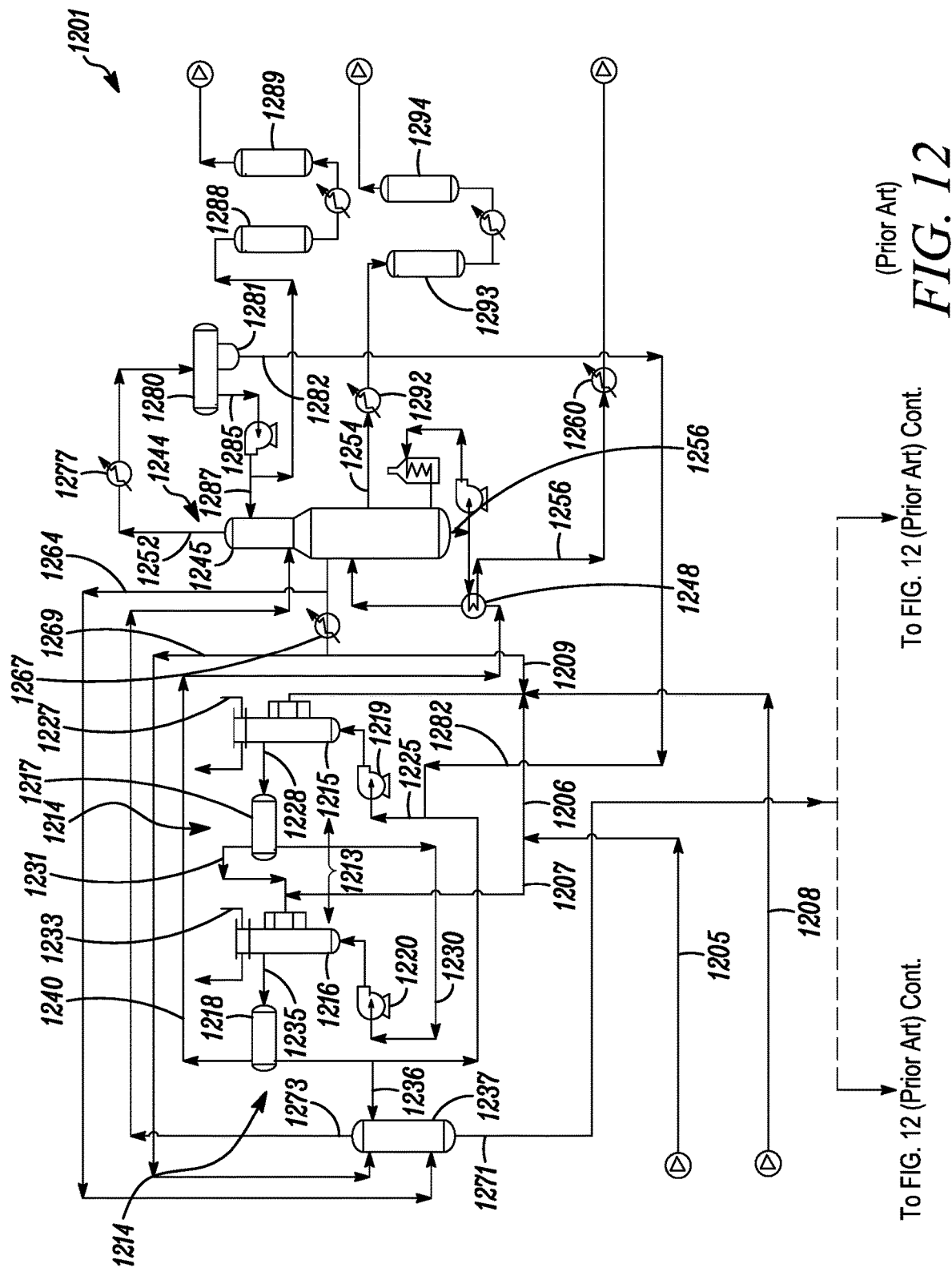
FIG. 12 is a schematic process flow diagram of a UOP HF alkylation unit which uses HF as the reaction catalyst to produce alkylate.

The present disclosure provides a method for converting an HF alkylation unit which utilizes HF as a reaction catalyst to a sulfuric acid (SA) alkylation unit which utilizes SA as a reaction catalyst. One example of the HF alkylation unit is depicted in FIG. 12 which is a simplified process flow diagram of a UOP HF alkylation unit 1201. An olefin feed stream 1205 containing olefins, propane and n-butane is split into a first reactor hydrocarbon feed stream 1206 and a second reactor hydrocarbon feed stream 1207. Isobutane from a make-up isobutane feed stream 1208 and a recycle isobutane stream 1209 is mixed with the first reactor hydrocarbon feed stream 1206.

The UOP HF alkylation unit 1201 includes a reaction section 1213 and a settling section 1214. The reaction section 1213 comprises a first reactor 1215 and a second reactor 1216. The settling section 1214 comprises a first HF acid settler 1217 and a second HF acid settler 1218. The UOP HF alkylation unit 1201 further comprises a first HF acid circulation pump 1219 and a second HF acid circulation pump 1220. The first reactor 1215 and the second reactor 1216 generally comprise vertically aligned tube and shell heat exchangers. In some embodiments, the heat exchangers may also be aligned horizontally or in other alignments. HF is introduced into the bottom of the shell side of the first reactor 1215 from a first HF acid recycle stream 1225. The hydrocarbon mixture of first reactor hydrocarbon feed stream 1206, make-up isobutane feed stream 1208 and recycle isobutane stream 1209 is introduced into the shell of the first reactor 1215 through several nozzles (not shown) positioned at various heights in the shell. These nozzles cause the hydrocarbon mixture to be jetted into the HF acid in the first reactor 1215 to promote mixing and to form an HF reaction emulsion. The HF reaction emulsion generally comprises isobutane and olefins uniformly dispersed throughout the HF acid.

The HF reaction emulsion is maintained at a preferred temperature of approximately 80° to 110° F. by passing cooling water in a first reactor cooling stream 1227 through the tube side of the tube and shell heat exchanger which functions as cooling means. In the first reactor 1215, the olefins react with the isobutane in the presence of HF acid in the HF reaction emulsion to produce alkylate.

The HF reaction emulsion from the first reactor 1215 is transferred to the first HF acid settler 1217 through first reactor effluent stream 1228. In the first HF acid settler 1217 the HF reaction emulsion is allowed to separate into a hydrocarbon phase (comprising primarily alkylate, isobutane, propane and n-butane) and an HF acid phase (comprising primarily HF). The HF acid phase flows from the bottom of the first HF acid settler 1217 through a second HF acid recycle stream 1230 and into the bottom of the second reactor 1216 on the shell side. The hydrocarbon phase from the first HF acid settler 1217 flows from the top of the first HF acid settler 1217 through a first HF acid settler hydrocarbon effluent stream 1231 into the second reactor hydrocarbon feed stream 1207 such that the olefins in the second reactor feed stream 1207 mix with the isobutane, propane, n-butane and alkylate in the first HF acid settler hydrocarbon effluent stream 1231. The hydrocarbon mixture of the effluent stream 1231 and the second reactor feed stream 1207 is then introduced into the shell of the second reactor 1216 through several nozzles (not shown) positioned at various heights in the shell to form an HF reaction emulsion with the HF acid in the second reactor 1216. The HF reaction emulsion is maintained at a preferred temperature of approximately 80° to 110° F. by passing cooling water in a second reactor cooling stream 1233 through the tube side of the tube and shell heat exchanger. Again, with HF acting as a catalyst, the isobutane and olefins in the HF reaction emulsion in the second reactor 1216 react to produce alkylate. Isoalkyl fluorides are produced as a by-product of the alkylation reactions in both the first reactor 1215 and the second reactor 1216.

The HF reaction emulsion from the second reactor 1216 is directed to the second HF acid settler 1218 through a second reactor effluent stream 1235. In the second HF acid settler 1218 the HF reaction emulsion separates into the HF acid phase comprising primarily HF and the hydrocarbon phase comprising primarily alkylate, isobutane, propane and n-butane with some HF and isoalkyl fluorides entrained therein. The HF acid phase from the second HF acid settler 1218 flows from the bottom of the second HF acid settler 1218 in the first HF acid recycle stream 1225. A portion of HF in the first acid recycle stream 1225 is drawn off in a HF slip stream 1236 and is directed to HF regenerator 1237. The first HF acid recycle stream 1225 is directed through the first HF acid circulation pump 1219 and into the first reactor 1215 under pressure. The second HF acid recycle stream 1230 is similarly directed through second HF acid circulation pump 1220 and directed into the second reactor 1216 under pressure.

The hydrocarbon phase from the second HF acid settler 1218 flows through a hydrocarbon effluent stream 1240 to a fractionation section 1244 comprising a main fractionator 1245. The hydrocarbon effluent stream 1240 passes through the shell side of a feed/bottom heat exchanger 1248 to preheat the hydrocarbon effluent stream 1240 prior to entry into the main fractionator 1245. The main fractionator 1245 separates hydrocarbons in the hydrocarbon effluent stream 1240 into four fractions: a top stream 1252 which comprises a mixture of HF and propane; the recycle isobutane stream 1209 which comprises mainly isobutane and which is recycled to the first reactor 1215; a vapor side stream 1254 which comprises primarily n-butane; and a bottom stream 1256 which comprises primarily alkylate.

The bottom stream 1256 passes through the tube side of the feed/bottom heat exchanger 1248 to preheat the hydrocarbon effluent stream 1240 prior to entry into the main fractionator 1245. The alkylate in the bottom stream 1256 is further cooled using an alkylate product cooler 1260 which uses cooling water as a coolant.

A first portion of isobutane in the recycle isobutane stream 1209 is diverted to the HF regenerator 1237 in isobutane stripping stream 1264. The isobutane in the isobutane stripping stream 1264 is used to strip HF from a mixture of HF and acid soluble oils in the HF regenerator 1237. After the first portion of isobutane is removed from the recycle isobutane stream 1209, the recycle isobutane stream 1209 passes through a recycle isobutane cooler 1267 which uses cooling water as a coolant to cool the recycle isobutane stream 1209. After the recycle isobutane stream 1209 is cooled in the recycle isobutane cooler 1267, a second portion of isobutane is separated from the recycle isobutane stream 1209 and directed to the HF regenerator 1237 in isobutane reflux stream 1269 to facilitate stripping of acid soluble oils from the mixture of HF and acid soluble oils.

The HF regenerator 1237 produces a top product comprising primarily HF and isobutane and a bottom product comprising primarily acid soluble oils. The acid soluble oils are removed from the HF regenerator 1237 in an acid soluble oil stream 1271. The HF and isobutane in the top product in the HF regenerator 1237 are directed to the main fractionator 1245 through a HF overhead stream 1273.

Separation means such as an HF stripper (not shown) is provided for separating the HF from the propane in the top stream 1252. FIG. 12 shows the top stream 1252 flowing through a propane condenser 1277 which uses cooling water to cool and condense the propane and HF in the top stream 1252. The cooled and condensed propane and HF enter a propane accumulator 1280 wherein the heavier HF accumulates in a boot 1281. The HF accumulated in the boot 1281 is drawn off through HF return stream 1282 and mixed with HF in the first HF acid recycle stream 1225. A propane overhead stream 1285 comprising primarily propane flows from the propane accumulator 1280. A portion of the propane overhead stream 1285 is directed to the main fractionator 1245 in a propane reflux stream 1287. The remainder of the propane overhead stream 1285 is directed through a propane defluorinator 1288 and a propane KOH treater 1289 to remove isoalkyl fluorides and HF respectively.

The n-butane rich vapor side stream 1254 is passed through a butane condenser 1292 and then an n-butane defluorinator 1293 and an n-butane KOH treater 1294 to remove isoalkyl fluorides and HF respectively.

In the UOP HF alkylation unit 1201 shown in FIG. 12, isobutane and HF flow through the first reactor 1215 and the second reactor 1216 in series while olefins flow through the first reactor 1215 and the second reactor 1216 in parallel. Although FIG. 12 discloses an UOP HF alkylation unit 1201 utilizing two reactors wherein isobutane flows therethrough in series and olefins flow through the reactors in parallel, UOP HF alkylation units 1201 using a single reactor can be utilized in plants with a relatively small capacity. In addition, some units utilize two reactors wherein both the olefins and the isobutane flow through the reactors in parallel.

When the purity of isobutane available for the make-up isobutane feed stream 1208 is relatively poor, the isobutane in the make-up isobutane feed stream 1208 is initially directed through the main fractionator 1245 and then to the reactor section 1213 through the recycle isobutane stream 1209 rather than directly to the reactor section.

The acid soluble oil stream 1271 is directed to a static mixer 1181 wherein the acid soluble oil (ASO) is mixed with an aqueous KOH solution 1188, and the acidic components contained in the ASO are neutralized. The ASO/KOH mixture 1182 is introduced into a ASO/KOH separator 1183 wherein ASO 1184 is allowed to separate from the aqueous KOH solution 1190 which is directed to an HF acid relief neutralizer 1191. The HF acid relief neutralizer 1191 in an HF alkylation unit is used to neutralize vapor streams and carryover liquids (if present) that may be received from an HF acid relief (flare) header 1186 during an upset when equipment in the HF alkylation unit needs to be rapidly depressurized. After the vapor streams and carryover liquids (if present) are neutralized by the aqueous KOH solution in the HF acid relief neutralizer 1191, a hydrocarbon stream 1185 comprising hydrocarbons contained in the vapor streams and carryover liquids (if present) exits the HF acid relief neutralizer 1191 and is directed to an HC relief (flare) header. The aqueous KOH solution 1187 can be recycled. A first portion of the recycle KOH solution 1188 is directed to the static mixer 1181. A second portion of the recycle KOH solution 1189 is combined with the aqueous KOH solution 1190 from the ASO/KOH separator 1183 to form a combined aqueous KOH solution stream 1192 which is introduced into the HF acid relief neutralizer 1191.

Figure 16:
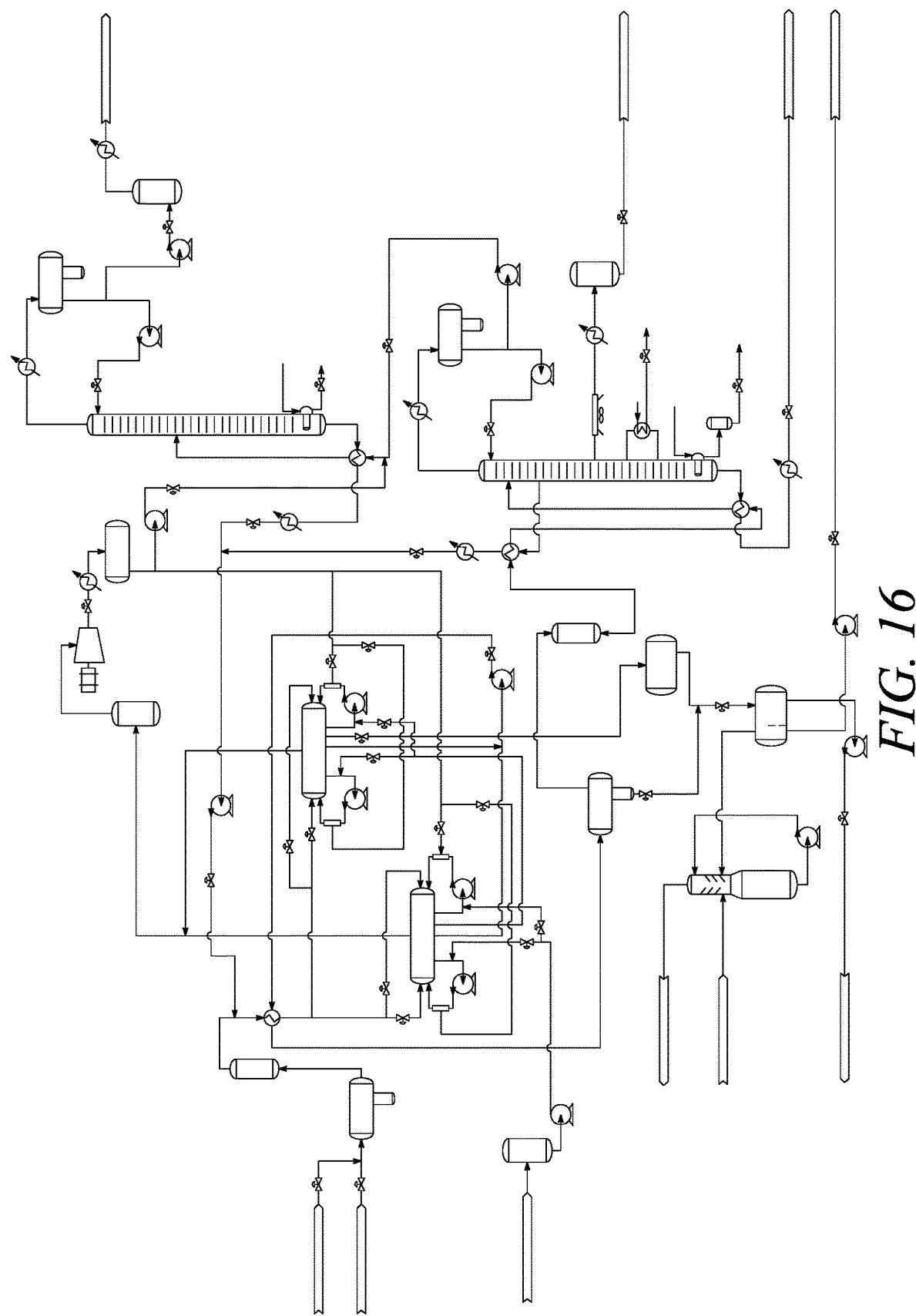
FIG. 16 is an overall schematic process flow diagram of a converted SA alkylation unit.
Figure 17:
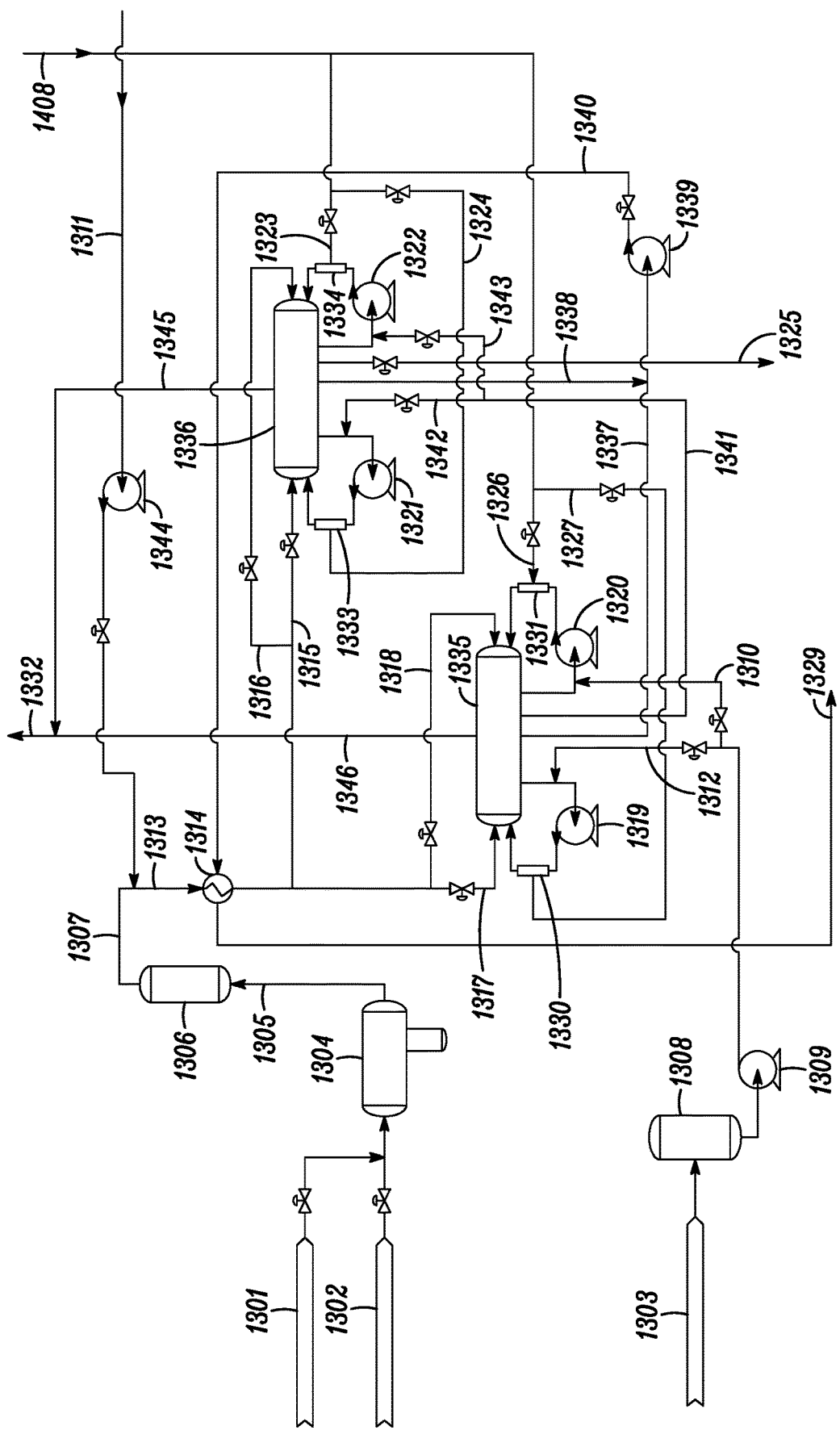
FIG. 17 is a schematic process flow diagram of the reaction section of the converted SA alkylation unit of FIG. 16.

FIGS. 16 to 21 depict an example of a converted SA alkylation unit which is converted from a pumped-flow HF alkylation unit. FIG. 17 is a schematic process flow diagram of the reaction section of the converted SA alkylation unit of FIG. 16. An olefin feed 1302 and a makeup isobutane feed 1301 are mixed and directed to a feed coalescer 1304 upstream of a feed dryer 1306. The feed coalescer 1304 is used to remove suspended water droplets entrained in the olefin and makeup isobutane feed streams. The resulting olefin/makeup isobutane mixture passes through the feed dryer 1306 to form the dried feed mixture 1307. A recycle isobutane stream 1311 is received by the reaction section through the isobutane recycle pump 1344 which can be retained from the existing HF alkylation unit. The recycle isobutane stream 1311 is mixed with the dried feed mixture 1307, and the resulting feed mixture 1313 passes through a feed/effluent heat exchanger 1314 to transfer heat to a net effluent stream 1340.

The cooled feed mixture is split into four hydrocarbon feed streams 1315, 1316, 1317 and 1318. In FIG. 17 the two split SA alkylation reactor systems are disposed in sequence to carry out an acid staging alkylation process. The hydrocarbon feed streams 1317 and 1318 are respectively fed into the two sides of a closed horizontal reactor vessel 1335 in a first split SA alkylation reactor system. The hydrocarbon feed streams 1315 and 1316 are respectively fed into the two sides of a closed horizontal reactor vessel 1336 in a second split SA alkylation reactor system.

The refrigerant recycle stream 1408 comprising isobutane is also split into four streams 1323, 1324, 1326 and 1327. The refrigerant recycle streams 1326 and 1327 are respectively directed to the two sides of the first split SA alkylation reactor system, and the refrigerant recycle streams 1323 and 1324 are respectively directed to the two sides of the second split SA alkylation reactor system. Fresh acid 1303, which can be stored in the acid storage drum 1308, is sent to the two sides of the first split SA alkylation reactor system via fresh acid pump 1309. In some embodiments, the acid storage drum 1308 is retained from the existing HF alkylation unit, and the fresh acid pump 1309 is a new equipment added or provided to the converted SA alkylation unit.

In the first split SA alkylation reactor system, emulsion exiting from the left side of the reactor vessel 1335 is mixed with fresh acid 1312. In some embodiments, a portion of spent acid 1341 exiting the reactor vessel 1335 can also be mixed with the emulsion and the fresh acid 1312. The resulting emulsion/acid mixture is sent to an external static mixer 1330 via an emulsion pump 1319. The emulsion/acid mixture is mixed with the refrigerant recycle stream 1327 in the external static mixer 1330 to form an emulsion which is fed into the reactor vessel 1335. On the other side of the first split SA alkylation reactor system, emulsion exiting from the right side of the reactor vessel 1335 is mixed with fresh acid 1310. In some embodiments, a portion of spent acid 1341 exiting the reactor vessel 1335 can also be mixed with the emulsion and the fresh acid 1310. The resulting emulsion/acid mixture is sent to an external static mixer 1331 via an emulsion pump 1320. The emulsion/acid mixture is mixed with the refrigerant recycle stream 1326 in the external static mixer 1331 to form an emulsion which is fed into the reactor vessel 1335.

The spent acid 1341 exiting the reactor vessel 1335 is sent to the second split SA alkylation reactor system via two streams 1342 and 1343. In the second split SA alkylation reactor system, emulsion exiting from the left side of the reactor vessel 1336 is mixed with spent acid 1342 from the first reactor system. In some embodiments, a portion of spent acid 1325 exiting the reactor vessel 1336 can also be mixed with the emulsion and the spent acid 1342. The resulting emulsion/acid mixture is sent to an external static mixer 1333 via an emulsion pump 1321. The emulsion/acid mixture is mixed with the refrigerant recycle stream 1324 in the external static mixer 1333 to form an emulsion which is fed into the reactor vessel 1336. On the other side of the second split SA alkylation reactor system, emulsion exiting from the right side of the reactor vessel 1336 is mixed with spent acid 1343 from the first reactor system. In some embodiments, a portion of spent acid 1325 exiting the reactor vessel 1336 can also be mixed with the emulsion and the spent acid 1343. The resulting emulsion/acid mixture is sent to an external static mixer 1334 via an emulsion pump 1322. The emulsion/acid mixture is mixed with the refrigerant recycle stream 1323 in the external static mixer 1334 to form an emulsion which is fed into the reactor vessel 1336.

Figure 18:
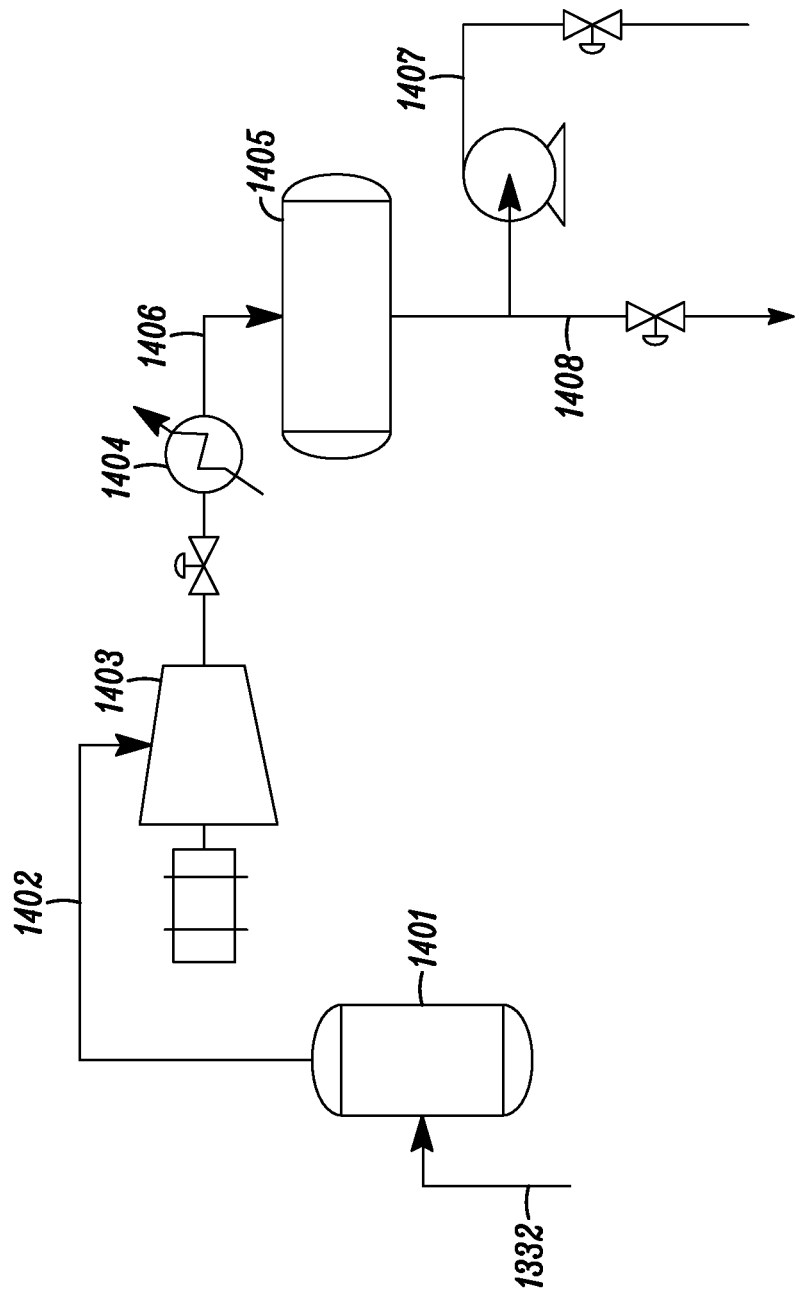
FIG. 18 is a schematic process flow diagram of the refrigeration section of the converted SA alkylation unit of FIG. 16.

Spent acid 1325 is sent to the SA blowdown section as shown in FIG. 21. The net effluent stream 1337 from the reactor vessel 1335 is combined with the net effluent stream 1338 from the reactor vessel 1336. The combined net effluent stream 1340 is directed to the feed/effluent heat exchanger 1314 via the net effluent pump 1339. The heated net effluent 1329 is directed to the net effluent treatment section as shown in FIG. 21. The vapor stream 1346 from the reactor vessel 1335 is combined with the vapor stream 1345 from the reactor vessel 1336. The combined vapor stream 1332 is sent to the refrigeration section as shown in FIG. 18. In some embodiments, the net effluent pump 1339 is a new equipment added or provided to the converted SA alkylation unit. In some embodiments, the emulsion pumps 1319, 1320, 1321 and 1322 are new equipment added or provided to the converted SA alkylation unit.

Figure 20:
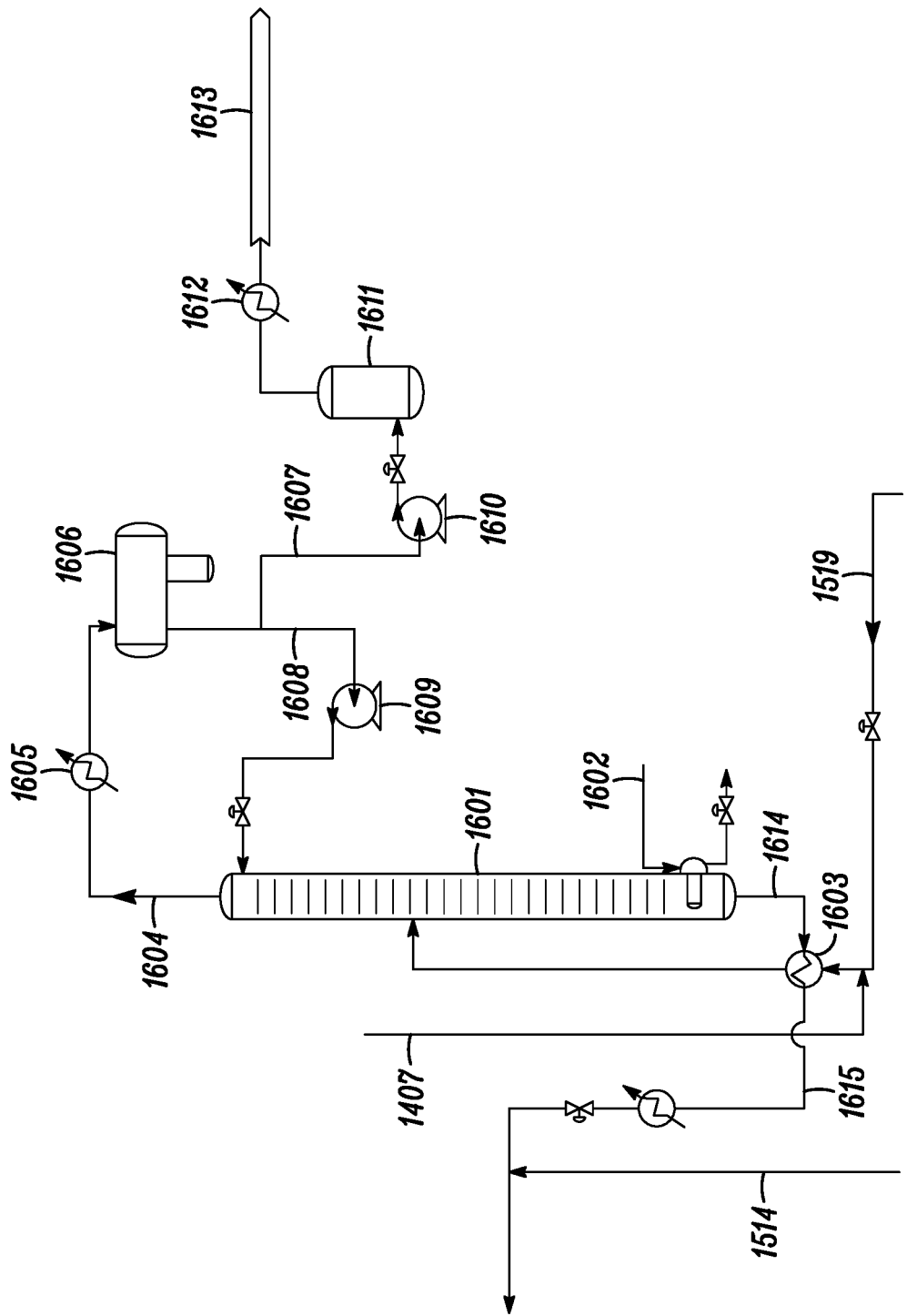
FIG. 20 is a schematic process flow diagram of another part of the fractionation section of the converted SA alkylation unit of FIG. 16.

FIG. 18 is a schematic process flow diagram of the refrigeration section of the converted SA alkylation unit of FIG. 16. The vapor stream 1332 is introduced into a compressor K/O (knockout) drum 1401 to remove suspended liquid droplets entrained in the vapor stream 1332. The resulting vapor stream 1402 from the compressor K/O drum 1401 is compressed by a refrigerant compressor 1403 and then condensed in a refrigerant condenser 1404. The refrigerant condensate 1406 is collected in a refrigerant accumulator 1405. A portion of the refrigerant condensate 1407 is directed to a depropanizer 1601 in the fractionation section as shown in FIG. 20. The remaining refrigerant condensate 1408 is directed to the reactor systems as a refrigerant recycle stream. In some embodiments, the refrigeration section further comprises a refrigerant recycle pump (not shown) downstream of the refrigerant accumulator to send the refrigerant recycle stream to the reactor system.

Figure 19:
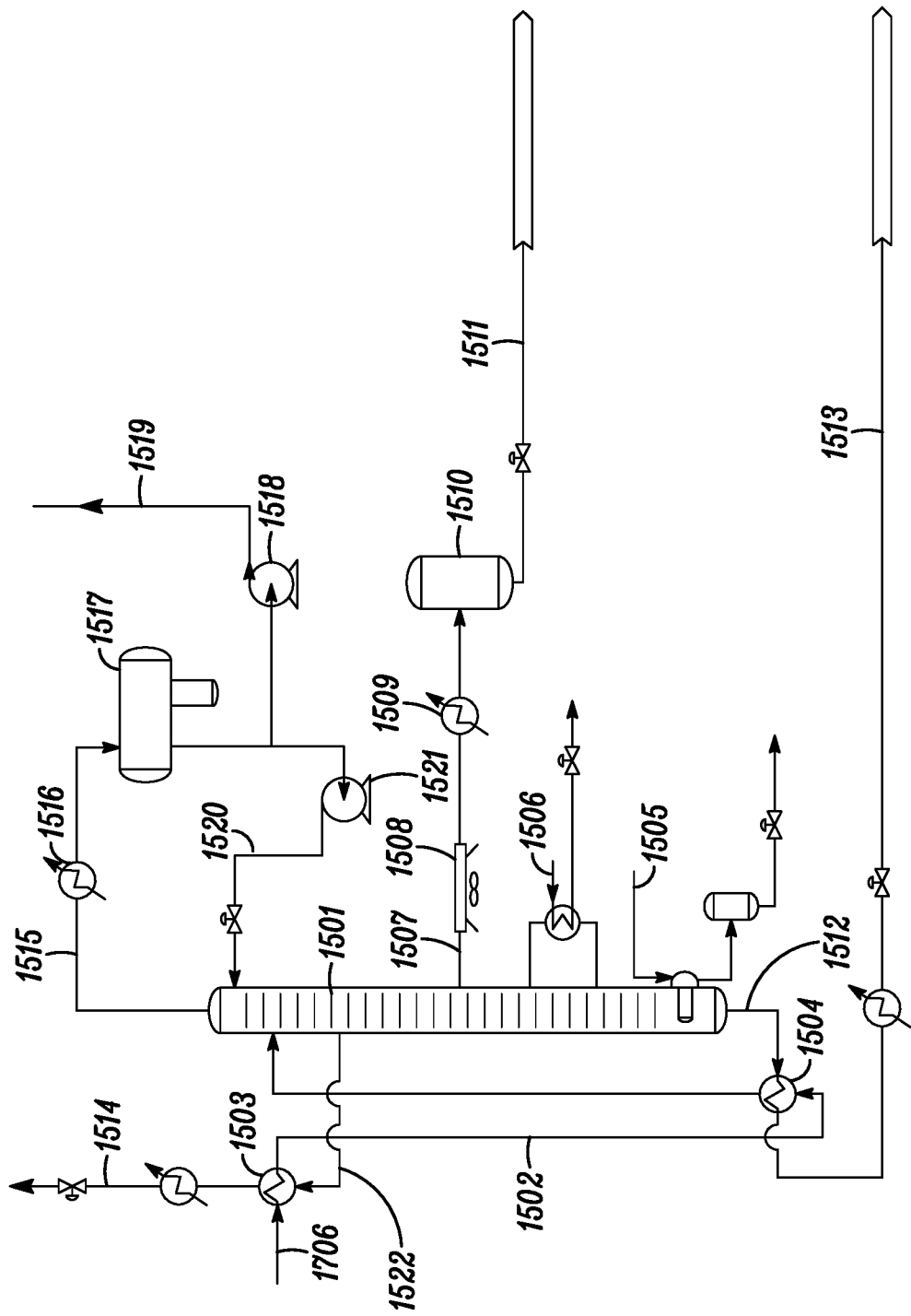
FIG. 19 is a schematic process flow diagram of a part of the fractionation section of the converted SA alkylation unit of FIG. 16.

FIG. 19 is a schematic process flow diagram of a part of the fractionation section of the converted SA alkylation unit of FIG. 16. The purified net effluent 1706 from the net effluent treatment section is fed into an isostripper column 1501 after being heated by the heat exchangers 1503 and 1504. The isostripper 1501 uses steams 1505 and 1506 as the heating medium to generate four fractions. The top stream 1515 comprising propane and isobutane is cooled in a condenser 1516, and the resulting condensate is collected in an isostripper reflux accumulator 1517. In some embodiments, the condenser 1516 and/or the isostripper reflux accumulator 1517 is retained from the existing HF alkylation unit. A portion of the top stream condensate 1520 is directed back into the isostripper 1501 by using an isostripper reflux pump 1521. The remainder of the top stream condensate 1519 is sent to a depropanizer column 1601 as shown in FIG. 20 via a depropanizer charge pump 1518. In some embodiments, the isostripper reflux pump 1521 and/or the depropanizer charge pump 1518 is retained from the existing HF alkylation unit.

An isobutane fraction exits the isostripper through the side draw 1522. The isobutane fraction is cooled by the isostripper feed/recycle isobutane heat exchanger 1503, and the cooled isobutane fraction 1514 is sent to the reactor system as a recycle isobutane stream. In some embodiments, the isostripper feed/recycle isobutane heat exchanger 1503 is retained from the existing HF alkylation unit. A n-butane fraction exits the isostripper through the side draw 1507 and is cooled by a n-butane condenser 1508 and a n-butane product trim cooler 1509. The cooled n-butane fraction is sent to a n-butane draw vapor/liquid separator 1510, and the liquid n-butane product 1511 is sent to a storage vessel (not shown). In some embodiments, the n-butane condenser 1508, the n-butane product trim cooler 1509 and/or the n-butane draw vapor/liquid separator 1510 is retained from the existing HF alkylation unit.

A bottom stream 1512 from the isostripper 1501 comprises primarily alkylate. The bottom stream 1512 is cooled by passing through an isostripper feed/bottoms heat exchanger 1504 to transfer heat to the purified net effluent stream 1706. The cooled bottom stream 1513 can be collected as an alkylate product. In some embodiments, the isostripper feed/bottoms heat exchanger 1504 is retained from the existing HF alkylation unit.

FIG. 20 is a schematic process flow diagram of another part of the fractionation section of the converted SA alkylation unit of FIG. 16. The refrigerant condensate 1407 from the refrigeration section and the top stream condensate 1519 from the isostripper column 1501 are combined to pass through the depropanizer feed/bottoms heat exchanger 1603 and fed into the depropanizer column 1601. The depropanizer 1601 uses steam 1602 as the heating medium to generate two fractions. The top stream 1604 comprising propane is cooled in a depropanizer condenser 1605, and the resulting condensate is collected in a depropanizer reflux accumulator 1606. In some embodiments, the depropanizer feed/bottoms heat exchanger 1603, the depropanizer condenser 1605 and/or the depropanizer reflux accumulator 1606 is retained from the existing HF alkylation unit. A portion of the top stream condensate 1608 is directed back into the depropanizer 1601 by using a depropanizer reflux pump 1609. The remainder of the top stream condensate 1607 is sent to a propane treater 1611 via a pump 1610. In some embodiments, the propane treater 1611 comprises a propane defluorinator and/or a propane KOH treater. The purified top stream condensate is cooled by a propane product cooler 1612 and collected as a propane product 1613. In some embodiments, the depropanizer reflux pump 1609, the propane defluorinator, the propane KOH treater and/or the propane product cooler 1612 is retained from the existing HF alkylation unit.

A bottom stream 1614 from the depropanizer 1601 comprises primarily isobutane. The bottom stream 1614 is cooled by passing through the depropanizer feed/bottoms heat exchanger 1603. The cooled bottom stream 1615 is combined with the cooled isobutane fraction 1514 from the isostripper 1501 to be sent to the reactor system as a recycle isobutane stream.

FIG. 21 is a schematic process flow diagram of the net effluent treatment section and the sulfuric acid blowdown section of the converted SA alkylation unit of FIG. 16. The net effluent 1329 from the reaction section is introduced into a sulfuric acid coalescer 1701 to remove residual sulfuric acid from the net effluent 1329. The resulting net effluent 1704 is further purified in a dry alumina adsorption vessel 1705. The purified net effluent stream 1706 is sent to the isostripper column 1501 as shown in FIG. 19. Sulfuric acid accumulated in the boot 1702 is drawn off through spent acid stream 1703 and sent to an acid blowdown drum 1709.

Spent acid 1325 from the reaction section is introduced into a spent acid aftersettler 1707 to remove residual hydrocarbons from the spent acid stream 1325. The hydrocarbons separated out in the spent acid aftersettler 1707 can exit from an outlet (not shown) to be recycled to the reactor systems. The resulting spent acid stream 1708 is combined with the spent acid stream 1703, and the combined spent acid stream is introduced into the acid blowdown drum 1709. Residual hydrocarbons contained in the spent acid can be flashed in the sulfuric acid blowdown drum 1709 to form an acidic hydrocarbon vapor effluent 1712. The acidic hydrocarbon vapor effluent 1712 is sent to a blowdown vapor scrubber 1715 wherein the acidic hydrocarbon vapor is contacted with a circulating caustic solution 1716. In some embodiments, the caustic solution is an aqueous sodium hydroxide (NaOH) solution. Liquid hydrocarbons 1711 are recovered at the bottom of one side of the sulfuric acid blowdown drum 1709. Spent acid 1710 is recovered at the bottom of the other side of the sulfuric acid blowdown drum 1709 and sent to a spent acid storage through a spent acid pump.

The acidic hydrocarbon vapor effluent 1712 is scrubbed by the caustic solution 1716 in the blowdown vapor scrubber 1715. Another acidic vapor stream 1714 comprising hydrocarbons from a sulfuric acid relief (flare) header is also introduced into the blowdown vapor scrubber 1715 to be scrubbed therein. A hydrocarbon stream 1713 comprising hydrocarbons exits the blowdown vapor scrubber 1715 and is directed to a hydrocarbon relief (flare) header.

Many aspects and embodiments have been described above and are merely exemplary and not limiting. After reading this specification, skilled artisans appreciate that other aspects and embodiments are possible without departing from the scope of the invention.

EXAMPLES

The concepts described herein will be further described in the following examples, which do not limit the scope of the invention described in the claims.

Example 1

Example 1 converted an HF alkylation unit which utilizes HF as a reaction catalyst to a SA alkylation unit. The original HF alkylation unit was a pumped-flow HF alkylation unit with horizontal HF acid settlers (1831 and 1835 in FIG. 22). FIG. 22 depicts a simplified process flow diagram of the original HF alkylation unit.

An olefin feed stream 1802 and a makeup isobutane feed 1801 are mixed and introduced into a feed coalescer 1810 to remove suspended water droplets entrained in the olefin and makeup isobutane feed streams. The resulting olefin/makeup isobutane mixture passes through the feed dryer 1833 to be further dried and is then split into two feed streams: one is mixed with recycle isobutane streams 1848 and 1849 to be fed into the first reactor 1832, and the other is mixed with a first HF acid settler hydrocarbon effluent stream 1842 to be fed into the second reactor 1834. Fresh HF acid 1803 which can be stored in an acid storage drum 1811 is combined with an HF acid recycle stream from the first HF acid settler 1831 and a regenerated HF acid from the top of the HF regenerator 1814, and the combined HF acid stream is introduced into the second reactor 1834.

The HF reaction emulsion 1841 from the first reactor 1832 is introduced into the first HF acid settler 1831 wherein the HF reaction emulsion is allowed to separate into a hydrocarbon phase and an HF acid phase. The HF acid phase flows from the bottom of the first HF acid settler 1831 as the HF acid recycle stream and is combined with the fresh HF acid 1803 and the regenerated HF acid to be fed into the second reactor 1834. The hydrocarbon phase flows from the top of the first HF acid settler 1831 and is mixed with the feed stream as the first HF acid settler hydrocarbon effluent stream 1842. The HF reaction emulsion 1840 from the second reactor 1834 is introduced into the second HF acid settler 1835 wherein the HF reaction emulsion separates into an HF acid phase and a hydrocarbon phase. A portion of the HF acid phase is sent to the first reactor 1832, and the remainder is sent to the HF regenerator 1814. The hydrocarbon phase 1843 is fed into an isostripper column 1819 after being heated by the heat exchangers 1838 and 1821.

The HF regenerator 1814 produces a top product (regenerated HF acid) comprising primarily HF and isobutane and a bottom product comprising primarily acid soluble oils (ASO). The acid soluble oils are sent to the polymer surge drum 1813 and the tar neutralizer 1812 to form tar product 1804.

The isostripper 1819 generates four fractions. The top stream 1844 comprising propane and isobutane is collected in an isostripper reflux accumulator 1823. A portion of the top stream 1846 is sent to a depropanizer column 1828 via a depropanizer charge pump 1822. An isobutane fraction 1848 is cooled by the isostripper feed/recycle isobutane heat exchanger 1838, and the cooled isobutane fraction is sent to an isostripper receiver 1829 acting as a surge drum for the isobutane recycle pump 1830. A n-butane fraction 1845 is purified by alumina treater 1818 and n-butane KOH treater 1817 to form n-butane product 1808. A bottom stream 1847 from the isostripper 1819 comprises primarily alkylate. The bottom stream 1847 is cooled the isostripper feed/bottoms heat exchanger 1821. The cooled bottom stream can be further cooled by an alkylate product cooler 1820 to form an alkylate product 1807.

The top stream 1846 from the isostripper column 1819 is heated by a depropanizer feed/bottoms heat exchanger 1839 and then fed into the depropanizer column 1828. The top stream 1850 generated in the depropanizer 1828 comprises propane and is collected in a depropanizer reflux accumulator 1827. A portion of the top stream 1851 is directed to an HF stripper 1826 to remove residual HF contained therein. Alumina treater 1825 and propane KOH treater 1824 further purify the top stream 1851 to form a propane product 1809. A bottom stream from the depropanizer 1828 comprises primarily isobutane. The bottom stream is cooled by the depropanizer feed/bottoms heat exchanger 1839 and sent to the isobutane recycle pump 1830 as the recycle isobutane stream 1849.

The original HF alkylation unit further comprises an HF acid relief neutralizer 1815 and an acid relief neutralizer circulation pump 1816. The HF acid relief neutralizer 1815 is used to neutralize vapor streams and carryover liquids (if present) that may be received from an HF acid relief (flare) header 1806. A hydrocarbon stream comprising hydrocarbons contained in the vapor streams and carryover liquids (if present) from the top of the HF acid relief neutralizer 1815 is directed to an HC relief (flare) header 1805.

In the original HF alkylation unit, the depropanizer 1828 supplies approximately 30% of the recycle isobutane to the reaction section, and the Isostripper 1819 supplies the remaining 70% of the recycle isobutane to the reaction section. This HF alkylation unit was originally designed to produce 10,500 bpsd (Barrel Per Stream Day) of alkylate product with a feed comprising FCC butylene and propylene.

Figure 23:
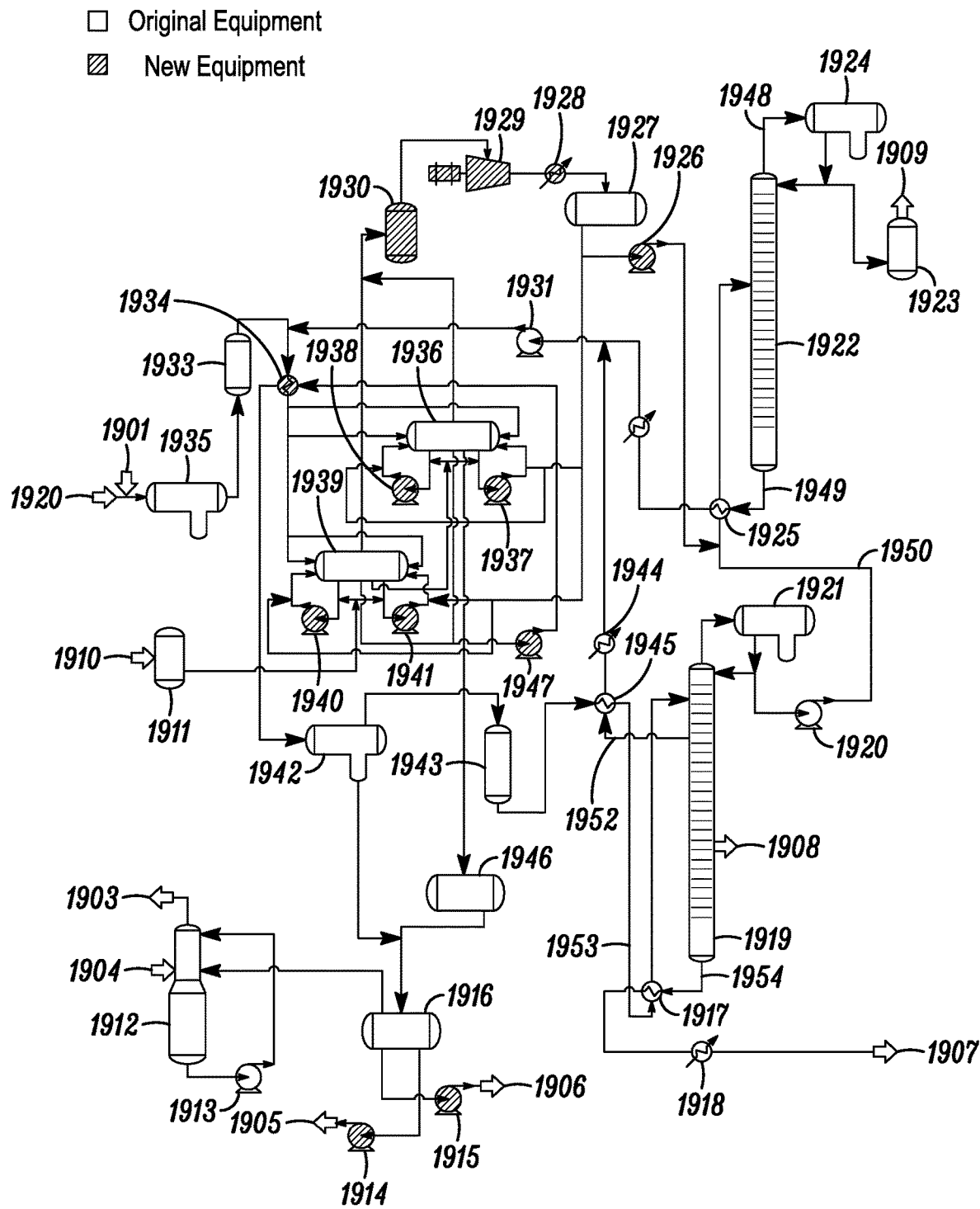
FIG. 23 shows a simplified process flow diagram of the converted SA alkylation unit which is converted from the original HF alkylation unit shown in FIG. 22.

FIG. 23 shows a simplified process flow diagram of the converted SA alkylation unit which is converted from the original HF alkylation unit shown in FIG. 22. The converted SA alkylation unit comprises two split SA alkylation reactor systems wherein the closed horizontal reactor vessels 1936 and 1939 are modified from the horizontal HF acid settlers 1831 and 1835 (FIG. 22) respectively. The four new emulsion pumps 1937, 1938, 1940 and 1941 are added in or provided to the reactor systems for emulsion recycle. The feed coalescer 1810 and the feed dryer 1833 in the HF alkylation unit (FIG. 22) are retained to provide the feed coalescer 1935 and the feed dryer 1933 in the converted SA alkylation unit for drying the olefin feed 1920 and the makeup isobutane feed 1901. A new feed/effluent heat exchanger 1934 is added or provided in the converted SA alkylation unit to reduce the temperature of hydrocarbon feed stream and increase the temperature of net effluent stream. The acid storage drum 1811 in the HF alkylation unit (FIG. 22) is retained or repurposed to provide an acid storage drum 1911 in the converted SA alkylation unit for storing fresh sulfuric acid 1910.

A refrigeration section is provided for the converted SA alkylation unit. The refrigeration section comprises a compressor K/O drum 1930, a refrigerant compressor 1929, a refrigerant condenser 1928 and a refrigerant accumulator 1927. The compressor K/O drum 1930, the refrigerant compressor 1929 and the refrigerant condenser 1928 are new equipment added or provided in the converted SA alkylation unit. The isostripper receiver 1829 in the HF alkylation unit (FIG. 22) is retained or repurposed to provide the refrigerant accumulator vessel 1927 for the refrigeration section in the converted SA alkylation unit.

The converted SA alkylation unit further comprises a sulfuric acid coalescer 1942 and a dry alumina adsorption vessel 1943 to purify the net effluent. A suitable vessel in the HF alkylation unit, such as an HF acid recontactor, can be retained or repurposed to provide the sulfuric acid coalescer 1942. A suitable vessel in the HF alkylation unit, such as an alumina treater 1818 or 1825 (FIG. 22), a propane defluorinator 1288 or an n-butane defluorinator 1293 (FIG. 12), can be retained or repurposed to provide the dry alumina adsorption vessel 1943.

The converted SA alkylation unit further comprises a spent acid aftersettler 1946, a sulfuric acid blowdown drum 1916, a blowdown vapor scrubber 1912 and a blowdown vapor scrubber circulation pump 1913. A suitable vessel in the HF alkylation unit, such as a remote HF storage tank, a remote HF blowdown drum, an ASO washer or a tar neutralizer (e.g., 1812 in FIG. 22) can be retained or modified to provide the spent acid aftersettler 1946 to remove the residual hydrocarbons from the spent acid. A suitable vessel in the HF alkylation unit, such as a remote HF storage tank, a remote HF blowdown drum, an ASO/KOH separator (e.g., 1183 in FIG. 12), an ASO surge drum or a polymer surge drum (e.g., 1813 in FIG. 22) can be retained or modified to provide the sulfuric acid blowdown drum 1916. The HF acid relief neutralizer 1815 (FIG. 22) in the HF alkylation unit is retained or modified to provide the blowdown vapor scrubber 1912. The acid relief neutralizer circulation pump 1816 (FIG. 22) in the HF alkylation unit is retained or modified to provide the blowdown vapor scrubber circulation pump 1913. In FIG. 23, 1903 indicates the hydrocarbon stream (e.g., 1713 in FIG. 21) which is directed to a hydrocarbon (HC) relief (flare) header, 1904 indicates the acidic vapor stream (e.g., 1714 in FIG. 21) from a sulfuric acid relief (flare) header, 1905 indicates the spent acid (e.g., 1710 in FIG. 21) which is sent to a spent acid storage through a spent acid pump 1914, and 1906 indicates liquid hydrocarbons (e.g., 1711 in FIG. 21) which are recovered at the bottom of one side of the sulfuric acid blowdown drum 1916.

The converted SA alkylation unit further comprises a fractionation section comprising an isostripper 1919 and a depropanizer 1922. The purified net effluent 1953 from the net effluent treatment section is fed into the isostripper column 1919 after being heated by an isostripper feed/recycle isobutane heat exchanger 1945 and an isostripper feed/bottoms heat exchanger 1917. The isostripper 1919 generates four fractions: a top stream comprising propane and isobutane, an isobutane fraction 1952, a n-butane fraction 1908 and a bottom stream 1954 comprising primarily alkylate. The isostripper 1819 in the HF alkylation unit (FIG. 22) is retained to provide the isostripper 1919. The depropanizer 1828 in the HF alkylation unit (FIG. 22) is retained to provide the depropanizer 1922. The isostripper feed/recycle isobutane heat exchanger 1838 in the HF alkylation unit (FIG. 22) is retained to provide the isostripper feed/recycle isobutane heat exchanger 1945. The isostripper feed/bottoms heat exchanger 1821 in the HF alkylation unit (FIG. 22) is retained to provide the isostripper feed/bottoms heat exchanger 1917.

The converted SA alkylation unit further comprises an isostripper reflux accumulator 1921, a depropanizer charge pump 1920 and an alkylate product cooler 1918 to cool the alkylate product 1907. The isostripper reflux accumulator 1823 in the HF alkylation unit (FIG. 22) is retained to provide the isostripper reflux accumulator 1921. The depropanizer charge pump 1822 in the HF alkylation unit (FIG. 22) is retained to provide the depropanizer charge pump 1920. The alkylate product cooler 1820 in the HF alkylation unit (FIG. 22) is retained to provide the alkylate product cooler 1918.

The top stream 1950 from the isostripper column 1919 is heated by a depropanizer feed/bottoms heat exchanger 1925 and then fed into the depropanizer column 1922 to generate a top stream 1948 comprising propane and a bottom stream 1949 comprising primarily isobutane. The isobutane streams from the isostripper column 1919 and the depropanizer column 1922 are recycled to the reaction section via an isobutane recycle pump 1931. The depropanizer feed/bottoms heat exchanger 1839 in the HF alkylation unit (FIG. 22) is retained to provide the depropanizer feed/bottoms heat exchanger 1925. The isobutane recycle pump 1830 in the HF alkylation unit (FIG. 22) is retained to provide the isobutane recycle pump 1931.

The converted SA alkylation unit further comprises a depropanizer reflux accumulator 1924 and a propane treater 1923 to generate purified propane product 1909. The depropanizer reflux accumulator 1827 in the HF alkylation unit (FIG. 22) is retained to provide the depropanizer reflux accumulator 1924. The propane KOH treater (e.g., 1289 in FIGS. 12 and 1824 in FIG. 22) and/or the n-butane KOH treater (e.g., 1294 in FIGS. 12 and 1817 in FIG. 22) in the HF alkylation unit is retained or modified to provide propane treater 1923 to purify propane product.

Table 1 provides a list of retained and new major equipment in the SA alkylation unit. As will be appreciated by those skilled in the art, when referring to an equipment or vessel in an HF alkylation unit, or describing an HF alkylation process or an HF alkylation unit, the terms "HF", "HF acid" and "acid" can be used interchangeably. When referring to an equipment or vessel in a SA alkylation unit, or describing a SA alkylation process or a SA alkylation unit, the terms "sulfuric acid" and "acid" can be used interchangeably. Most modern HF alkylation units have remote HF acid storage tanks and remote HF acid blowdown drums. Depending on the location of these vessels and the requirements of the conversion solution offered, these may be retained as spent acid aftersettlers, acid blowdown drums, or they may be modified to provide the closed reactor vessels in the sulfuric acid alkylation reactor system. Potential opportunities to retain or reuse these vessels will be determined on a case-by-case basis. To maximize product quality and minimize acid consumption, the SA alkylation process utilizing the converted SA alkylation unit can be designed to segregate olefin feed and to stage acid flows between reactor systems.

TABLE 1

Major Equipment List

| Existing Equipment Retained or Repurposed | New Equipment Added for Conversion | Existing Equipment Decommissioned |
|---|---|---|
| Acid Blowdown Drum (Remote) | Emulsion Pumps | HF Acid Circulation Pump |
| Acid Neutralization Pit | Compressor K/O Drum | HF Regenerator |
| Acid Settlers | Feed/Effluent Heat Exchangers | HF Regenerator Condenser |
| Acid Storage Tanks | Fresh Acid Pumps | HF Regenerator IC4 Superheater |
| Alkylate Cooler | Net Effluent Pumps | HF Regenerator Overhead Pump |
| Alkylate Flush Pump | Propane Purge Pumps | HF Alkylation Reactors |
| Alkylate Product Coolers | Refrigerant Condensers | HF Stripper |
| Depropanizer | Refrigerant Compressor | Settled Acid Pump |
| Depropanizer Reflux Accumulator | Spent Acid Pumps | |
| Depropanizer Bottoms Cooler | | |
| Depropanizer Charge Pumps | | |
| Depropanizer Condensers | | |
| Depropanizer Feed/Bottoms Heat Exchangers | | |
| Depropanizer Reboiler | | |
| Depropanizer Reflux Pumps | | |
| Feed Coalescer | | |
| Feed Dryers | | |
| Isobutane Recycle Pumps | | |
| Isostripper | | |
| Isostripper Reflux Accumulator | | |
| Isostripper Condensers | | |
| Isostripper Feed/Bottoms Heat Exchangers | | |
| Isostripper Feed/Recycle IC4 Heat Exchangers | | |
| Isostripper Reboiler | | |
| Isostripper Receiver | | |
| Isostripper Reflux Pumps | | |
| Isostripper Side Stream Cooler | | |
| KOH Pumps | | |
| n-Butane Condensers | | |
| n-Butane Defluorinators | | |
| n-Butane Draw Vapor/Liquid Separator | | |
| n-Butane KOH Treaters | | |
| n-Butane Product Trim Cooler | | |
| Polymer Surge Drums | | |
| Propane Defluorinators | | |
| Propane KOH Treaters | | |
| Acid Relief Neutralizer | | |
| Acid Relief Neutralizer Circulation Pump | | |
| Tar Neutralizer | | |

Since the isostripper and depropanizer are designed to supply 100% of the recycle isobutane in the HF alkylation unit, a significant capacity increase of 96% is achieved with the addition of a refrigeration section which provides approximately 50% of the total recycle isobutane requirement as a refrigerant recycle stream. Table 2 provides a summary of feed and product streams for the conversion methods of this Example. Table 3 provides a summary of alkylate properties. Table 4 provides examples of capacity expansion including Example 1 disclosed above. HF unit means the existing HF alkylation unit, and SA unit means the converted SA alkylation unit.

TABLE 2

Feed and Product Streams

| | Olefin Feed | Isobutane Feed | Propane Product | n-Butane Product | Alkylate Product |
|---|---|---|---|---|---|
| Volume Flow (bpsd) | 19,795 | 9,564 | 2,334 | 1,270 | 20,569 |
| Composition (vol %) | | | | | |
| Ethane | 0.03 | | 0.23 | | |
| Propane | 9.51 | 1.99 | 97.50 | | |
| i-Butane | 21.78 | 95.00 | 2.26 | 16.71 | 0.20 |
| n-Butane | 6.98 | 3.01 | 0.02 | 82.29 | 3.03 |
| i-Pentane | 2.60 | | | 0.98 | 7.11 |
| n-Pentane | 0.72 | | | 0.02 | 0.70 |
| Propylene | 24.61 | | | | |
| Butylene | 33.07 | | | | |
| Amylene | 0.71 | | | | |
| C6+ | 0.00 | | | | 88.96 |

TABLE 3

Alkylate Properties

| | |
|---|---|
| % Propylene/Total Olefins (Feed) | 42.1 |
| % Isobutylene/Total Olefins (Feed) | 18.4 |
| RON | 93.5-94.0 |
| (R + M)/2 | 92.7-93.2 |
| D-86 T90, ° F. (° C.) | <290 (143) |
| D-86 EP, ° F. (° C.) | <400 (204) |
| Acid Consumption, lbs acid/gal alkylate | 0.45-0.50 |
| Alkylate Reid Vapor Pressure (RVP), psia | 5.0 |
| Alkylate Sulfur, ppm | <2 |

TABLE 4

Capacity Expansion

| Example | Feed Type | HF Unit Capacity (bpsd) | SA Unit Capacity (bpsd) | Capacity Increase |
|---|---|---|---|---|
| 1 | FCC $C_3^=/C_4^=$ | 10,500 | 20,569 | +96% |
| 2 | MTBE $C_3^=/C_4^=$ | 13,500 | 22,600 | +68% |
| 3 | FCC $C_3^=/C_4^=$ | 10,000 | 27,810 | +178% |
| 4 | MTBE $C_4^=$ | 13,500 | 24,435 | +81% |
| 5 | FCC $C_4^=$ | 20,500 | 43,865 | +114% |
| 6 | FCC $C_3^=/C_4^=$ | 10,000 | 24,309 | +143% |

Note that not all of the activities described above in the general description or the examples are required, that a portion of a specific activity may not be required, and that one or more further activities may be performed in addition to those described. Still further, the order in which activities are listed are not necessarily the order in which they are performed.

In the foregoing specification, the concepts have been described with reference to specific embodiments. However, one of ordinary skill in the art appreciates that various modifications and changes can be made without departing from the scope of the invention as set forth in the claims below. Accordingly, the specification is to be regarded in an illustrative rather than a restrictive sense, and all such modifications are intended to be included within the scope of invention.

Benefits, other advantages, and solutions to problems have been described above with regard to specific embodiments. However, the benefits, advantages, solutions to problems, and any feature(s) that may cause any benefit, advantage, or solution to occur or become more pronounced are not to be construed as a critical, required, or essential feature of any or all the claims.

It is to be appreciated that certain features are, for clarity, described herein in the context of separate embodiments, may also be provided in combination in a single embodiment. Conversely, various features that are, for brevity, described in the context of a single embodiment, may also be provided separately or in any subcombination.

Embodiments

For further illustration, additional non-limiting embodiments of the present disclosure are set forth below.

For example, embodiment 1 is a sulfuric acid alkylation reactor system comprising: (a) a closed reactor vessel comprising a shell, a vapor outlet, and an emulsion outlet; (b) a distributor located at the lower portion of the reactor vessel; (c) a mixer fluidly connected with the distributor; and (d) an emulsion pump fluidly connected with the mixer and the emulsion outlet; wherein the emulsion pump is located outside the reactor vessel.

Embodiment 2 is a sulfuric acid alkylation reactor system as set forth in embodiment 1, wherein the sulfuric acid alkylation reactor system is part of a sulfuric acid alkylation unit, the sulfuric acid alkylation unit comprises a refrigeration section comprising a refrigerant recycle pump.

Embodiment 3 is a sulfuric acid alkylation reactor system as set forth in embodiment 2, wherein the vapor outlet is fluidly connected with the refrigeration section.

Embodiment 4 is a sulfuric acid alkylation reactor system as set forth in one of embodiments 1-3, wherein the distributor is substantially horizontal.

Embodiment 5 is a sulfuric acid alkylation reactor system as set forth in one of embodiments 1-3, wherein the distributor extends substantially along the bottom interior surface of the reactor vessel.

Embodiment 6 is a sulfuric acid alkylation reactor system as set forth in one of embodiments 1-5, wherein the mixer is an internal static mixer located at the lower portion of the reactor vessel, the distributor is downstream of the internal static mixer and is directly connected with the internal static mixer.

Embodiment 7 is a sulfuric acid alkylation reactor system as set forth in embodiment 6, wherein the distributor extends from the internal static mixer. Embodiment 8 is a sulfuric acid alkylation reactor system as set forth in one of embodiments 6-7 further comprising an external static mixer fluidly connected with the internal static mixer and the emulsion pump, wherein the external static mixer is located outside the reactor vessel.

Embodiment 9 is a sulfuric acid alkylation reactor system as set forth in embodiment 8, wherein the external static mixer is directly connected with the internal static mixer and is also directly connected with the emulsion pump.

Embodiment 10 is a sulfuric acid alkylation reactor system as set forth in one of embodiments 6-9, wherein the internal static mixer is fluidly connected with an olefin source.

Embodiment 11 is a sulfuric acid alkylation reactor system as set forth in one of embodiments 6-10, wherein the internal static mixer is fluidly connected with a recycled isoparaffin source.

Embodiment 12 is a sulfuric acid alkylation reactor system as set forth in one of embodiments 8-11, wherein the external static mixer is fluidly connected with the refrigerant recycle pump.

Embodiment 13 is a sulfuric acid alkylation reactor system as set forth in one of embodiments 6-12, wherein the reactor system comprises one to three internal static mixers in combination with one to ten distributors.

Embodiment 14 is a sulfuric acid alkylation reactor system as set forth in one of embodiments 1-5, wherein the mixer is a homogenizer fluidly connected with the distributor, and the homogenizer is located outside the reactor vessel and is upstream of the distributor.

Embodiment 15 is a sulfuric acid alkylation reactor system as set forth in embodiment 14, wherein the homogenizer is an in-line rotor stator mixer.

Embodiment 16 is a sulfuric acid alkylation reactor system as set forth in embodiment 15 further comprising an external static mixer fluidly connected with the in-line rotor stator mixer and the emulsion pump, wherein the external static mixer is located outside the reactor vessel.

Embodiment 17 is a sulfuric acid alkylation reactor system as set forth in embodiment 16, wherein the external static mixer is directly connected with the in-line rotor stator mixer and is also directly connected with the emulsion pump, and the in-line rotor stator mixer is directly connected with the distributor.

Embodiment 18 is a sulfuric acid alkylation reactor system as set forth in one of embodiments 15-17, wherein the in-line rotor stator mixer is fluidly connected with an olefin source upstream of the in-line rotor stator mixer with respect to the flow direction of olefin.

Embodiment 19 is a sulfuric acid alkylation reactor system as set forth in one of embodiments 15-18, wherein the in-line rotor stator mixer is fluidly connected with a recycled isoparaffin source upstream of the in-line rotor stator mixer.

Embodiment 20 is a sulfuric acid alkylation reactor system as set forth in one of embodiments 16-19, wherein the external static mixer is fluidly connected with the refrigerant recycle pump.

Embodiment 21 is a sulfuric acid alkylation reactor system as set forth in one of embodiments 1-20, wherein the reactor vessel further comprises a second emulsion outlet fluidly connected with a sulfuric acid settler outside the reactor vessel.

Embodiment 22 is a sulfuric acid alkylation reactor system as set forth in embodiment 21, wherein the emulsion pump is also fluidly connected with the sulfuric acid settler outside the reactor vessel.

Embodiment 23 is a sulfuric acid alkylation reactor system as set forth in one of embodiments 1-20, wherein the reactor vessel further comprises a partition baffle, a coalescing media, a spent acid outlet, and a net effluent outlet; the partition baffle and the coalescing media extend upwardly from the bottom of the reactor vessel respectively, the coalescing media is downstream of the partition baffle and defines a reaction zone and an acid settling zone inside the reactor vessel, the reaction zone is upstream of the coalescing media, the acid settling zone is downstream of the coalescing media, the emulsion pump is also fluidly connected with the spent acid outlet, and the distributor is located at the reaction zone.

Embodiment 24 is a sulfuric acid alkylation reactor system as set forth in embodiment 23, wherein the reactor system further comprises a spent acid pump directly connected with the spent acid outlet, the spent acid pump is upstream of the emulsion pump and is fluidly connected with the emulsion pump.

Embodiment 25 is a sulfuric acid alkylation reactor system as set forth in embodiments 23 or 24, wherein the partition baffle and the coalescing media are substantially parallel to each other and extend through the shell respectively at the lower portion of the reactor vessel.

Embodiment 26 is a sulfuric acid alkylation reactor system as set forth in one of embodiments 23-25, wherein the reactor vessel further comprises a second partition baffle extending upwardly from the bottom of the reactor vessel, the second partition baffle is downstream of the coalescing media and defines an effluent zone downstream of the second partition baffle.

Embodiment 27 is a sulfuric acid alkylation reactor system as set forth in embodiment 26, wherein the second partition baffle is substantially parallel to the coalescing media and extends through the shell at the lower portion of the reactor vessel.

Embodiment 28 is a sulfuric acid alkylation reactor system as set forth in any of the preceding embodiments, wherein the emulsion pump is also fluidly connected with a fresh acid source.

Embodiment 29 is a sulfuric acid alkylation reactor system as set forth in any of the preceding embodiments, wherein the vapor outlet is at the top of the reactor vessel.

Embodiment 30 is a sulfuric acid alkylation reactor system as set forth in any of the preceding embodiments, wherein the reactor system further comprises a plurality of draft tubes extending upwardly from above the distributor.

Embodiment 31 is a sulfuric acid alkylation reactor system as set forth in one of embodiments 1-30, wherein the reactor vessel is a horizontal reactor vessel.

Embodiment 32 is a sulfuric acid alkylation reactor system as set forth in one of embodiments 1-30, wherein the reactor vessel is a vertical reactor vessel.

Embodiment 33 is a split sulfuric acid alkylation reactor system comprising: (a) a closed horizontal reactor vessel comprising a shell, a vapor outlet, a first emulsion outlet, a second emulsion outlet, a first partition baffle, a first coalescing media, a second partition baffle, a second coalescing media, a spent acid outlet, and a net effluent outlet; (b) a first distributor located at the lower portion of the reactor vessel; (c) a second distributor located at the lower portion of the reactor vessel; (d) a first mixer fluidly connected with the first distributor; (e) a second mixer fluidly connected with the second distributor; (f) a first emulsion pump fluidly connected with the first mixer, the first emulsion outlet, and the spent acid outlet; and (g) a second emulsion pump fluidly connected with the second mixer, the second emulsion outlet, and the spent acid outlet; wherein the first partition baffle, the second partition baffle, the first coalescing media, and the second coalescing media extend upwardly from the bottom of the reactor vessel respectively, the first coalescing media is downstream of the first partition baffle, the second coalescing media is downstream of the second partition baffle, the first coalescing media and the second coalescing media define a first reaction zone, a second reaction zone and an acid settling zone inside the reactor vessel, the first reaction zone is upstream of the first coalescing media, the second reaction zone is upstream of the second coalescing media, the acid settling zone is between the first coalescing media and the second coalescing media, the first distributor is located at the first reaction zone, the second distributor is located at the second reaction zone, the first emulsion pump and the second emulsion pump are located outside the reactor vessel.

Embodiment 34 is a split sulfuric acid alkylation reactor system as set forth in embodiment 33, wherein the split sulfuric acid alkylation reactor system is part of a sulfuric acid alkylation unit, the sulfuric acid alkylation unit comprises a refrigeration section comprising a refrigerant recycle pump.

Embodiment 35 is a split sulfuric acid alkylation reactor system as set forth in embodiment 34, wherein the vapor outlet is fluidly connected with the refrigeration section.

Embodiment 36 is a split sulfuric acid alkylation reactor system as set forth in one of embodiments 33-35, wherein both the first distributor and the second distributor are substantially horizontal.

Embodiment 37 is a split sulfuric acid alkylation reactor system as set forth in one of embodiments 33-35, wherein both the first distributor and the second distributor extend substantially along the bottom interior surface of the reactor vessel.

Embodiment 38 is a split sulfuric acid alkylation reactor system as set forth in one of embodiments 33-37, wherein the first mixer is a first internal static mixer located at the lower portion of the first reaction zone, the first distributor is downstream of the first internal static mixer and is directly connected with the first internal static mixer, the second mixer is a second internal static mixer located at the lower portion of the second reaction zone, the second distributor is downstream of the second internal static mixer and is directly connected with the second internal static mixer.

Embodiment 39 is a split sulfuric acid alkylation reactor system as set forth in embodiment 38, wherein the first distributor extends from the first internal static mixer, and the second distributor extends from the second internal static mixer.

Embodiment 40 is a split sulfuric acid alkylation reactor system as set forth in one of embodiments 38-39 further comprising a first external static mixer fluidly connected with the first internal static mixer and the first emulsion pump, and a second external static mixer fluidly connected with the second internal static mixer and the second emulsion pump, wherein both the first external static mixer and the second external static mixer are located outside the reactor vessel.

Embodiment 41 is a split sulfuric acid alkylation reactor system as set forth in embodiment 40, wherein the first external static mixer is directly connected with the first internal static mixer and is also directly connected with the first emulsion pump, and the second external static mixer is directly connected with the second internal static mixer and is also directly connected with the second emulsion pump.

Embodiment 42 is a split sulfuric acid alkylation reactor system as set forth in one of embodiments 38-41, wherein the first internal static mixer and the second internal static mixer are fluidly connected with an olefin source.

Embodiment 43 is a split sulfuric acid alkylation reactor system as set forth in one of embodiments 38-42, wherein the first internal static mixer and the second internal static mixer are fluidly connected with a recycled isoparaffin source.

Embodiment 44 is a split sulfuric acid alkylation reactor system as set forth in one of embodiments 40-43, wherein the first external static mixer and the second external static mixer are fluidly connected with the refrigerant recycle pump.

Embodiment 45 is a split sulfuric acid alkylation reactor system as set forth in one of embodiments 38-44, wherein the reactor system comprises one to three first internal static mixers in combination with one to ten first distributors, and one to three second internal static mixers in combination with one to ten second distributors.

Embodiment 46 is a split sulfuric acid alkylation reactor system as set forth in one of embodiments 33-37, wherein the first mixer is a first homogenizer fluidly connected with the first distributor, the second mixer is a second homogenizer fluidly connected with the second distributor, the first homogenizer is located outside the reactor vessel and is upstream of the first distributor, and the second homogenizer is located outside the reactor vessel and is upstream of the second distributor.

Embodiment 47 is a split sulfuric acid alkylation reactor system as set forth in embodiment 46, wherein the first homogenizer is a first in-line rotor stator mixer, and the second homogenizer is a second in-line rotor stator mixer.

Embodiment 48 is a split sulfuric acid alkylation reactor system as set forth in embodiment 47 further comprising a first external static mixer fluidly connected with the first in-line rotor stator mixer and the first emulsion pump, and a second external static mixer fluidly connected with the second in-line rotor stator mixer and the second emulsion pump, wherein both the first external static mixer and the second external static mixer are located outside the reactor vessel.

Embodiment 49 is a split sulfuric acid alkylation reactor system as set forth in embodiment 48, wherein the first external static mixer is directly connected with the first in-line rotor stator mixer and is also directly connected with the first emulsion pump, the first in-line rotor stator mixer is directly connected with the first distributor, the second external static mixer is directly connected with the second in-line rotor stator mixer and is also directly connected with the second emulsion pump, the second in-line rotor stator mixer is directly connected with the second distributor.

Embodiment 50 is a split sulfuric acid alkylation reactor system as set forth in one of embodiments 47-49, wherein the first in-line rotor stator mixer is fluidly connected with an olefin source upstream of the first in-line rotor stator mixer with respect to the flow direction of olefin, and the second in-line rotor stator mixer is fluidly connected with an olefin source upstream of the second in-line rotor stator mixer with respect to the flow direction of olefin.

Embodiment 51 is a split sulfuric acid alkylation reactor system as set forth in one of embodiments 47-50, wherein the first in-line rotor stator mixer is fluidly connected with a recycled isoparaffin source upstream of the first in-line rotor stator mixer, and the second in-line rotor stator mixer is fluidly connected with a recycled isoparaffin source upstream of the second in-line rotor stator mixer.

Embodiment 52 is a split sulfuric acid alkylation reactor system as set forth in one of embodiments 48-51, wherein the first external static mixer and the second external static mixer are fluidly connected with the refrigerant recycle pump.

Embodiment 53 is a split sulfuric acid alkylation reactor system as set forth in one of embodiments 33-52, wherein the reactor system further comprises a spent acid pump outside the reactor vessel directly connected with the spent acid outlet, the spent acid pump is upstream of the first emulsion pump and is fluidly connected with the first emulsion pump, the spent acid pump is also upstream of the second emulsion pump and is fluidly connected with the second emulsion pump.

Embodiment 54 is a split sulfuric acid alkylation reactor system as set forth in one of embodiments 33-53, wherein the first partition baffle and the first coalescing media are substantially parallel to each other and extend through the shell respectively at the lower portion of the reactor vessel, the second partition baffle and the second coalescing media are substantially parallel to each other and extend through the shell respectively at the lower portion of the reactor vessel.

Embodiment 55 is a split sulfuric acid alkylation reactor system as set forth in one of embodiments 33-54, wherein the first emulsion pump and the second emulsion pump are fluidly connected with a fresh acid source.

Embodiment 56 is a split sulfuric acid alkylation reactor system as set forth in one of embodiments 33-55, wherein the vapor outlet is at the top of the reactor vessel.

Embodiment 57 is a split sulfuric acid alkylation reactor system as set forth in one of embodiments 33-56, wherein the reactor system further comprises a plurality of first draft tubes extending upwardly from above the first distributor, and a plurality of second draft tubes extending upwardly from above the second distributor.

Embodiment 58 is a split sulfuric acid alkylation reactor system as set forth in one of embodiments 33-57, wherein the reactor system further comprises a raised sump having an open top and an outlet, the raised sump is inside the reactor vessel, and the outlet either is the net effluent outlet or is directly connected with the net effluent outlet.

Embodiment 59 is a split sulfuric acid alkylation reactor system as set forth in one of embodiments 33-57, wherein the reactor system further comprises a third partition baffle and a fourth partition baffle, the third partition baffle and the fourth partition baffle extend upwardly from the bottom of the reactor vessel respectively, the third partition baffle is downstream of the first coalescing media, the fourth partition baffle is downstream of the second coalescing media, the third partition baffle and the fourth partition baffle define an effluent zone between the third partition baffle and the fourth partition baffle, the third partition baffle and the fourth partition baffle also separate the acid settling zone into a first acid settling zone and a second acid settling zone, the first acid settling zone is between the first coalescing media and the third partition baffle, the second acid settling zone is between the second coalescing media and the fourth partition baffle.

Embodiment 60 is a split sulfuric acid alkylation reactor system as set forth in embodiment 59, wherein the third partition baffle is substantially parallel to the first coalescing media, the fourth partition baffle is substantially parallel to the second coalescing media, the third partition baffle and the fourth partition baffle respectively extends through the shell at the lower portion of the reactor vessel.

Embodiment 61 is a split sulfuric acid alkylation reactor system as set forth in embodiments 59 or 60, wherein the spent acid outlet comprises a first spent acid outlet and a second spent acid outlet, the first spent acid outlet is at the lower end of the first acid settling zone, the second spent acid outlet is at the lower end of the second acid settling zone, the first emulsion pump is fluidly connected with the first spent acid outlet, the second emulsion pump is fluidly connected with the second spent acid outlet, the net effluent outlet is at the lower end of the effluent zone.

Embodiment 62 is an alkylation process comprising contacting an olefin with an isoparaffin in the presence of a sulfuric acid catalyst to produce a product mixture comprising an alkylate wherein the contacting is performed in the reactor system as set forth in any of the preceding embodiments.

Embodiment 63 is an alkylation process as set forth in embodiment 62, wherein the molar ratio of isoparaffin to olefin introduced into the reactor system is in the range of from about 2:1 to about 50:1.

Embodiment 64 is an alkylation process as set forth in embodiments 62 or 63, wherein the acid strength of the sulfuric acid solution in the reactor vessel is in the range of about 80 wt % to about 99.5 wt %.

Embodiment 65 is an alkylation process as set forth in one of embodiments 62-64, wherein the volume percentage of the sulfuric acid solution in the reaction zone based on the total volume of sulfuric acid solution and hydrocarbons in the reaction zone ranges from about 5% to about 70%.

Embodiment 66 is an alkylation process as set forth in one of embodiments 62-65, wherein the temperature in the reactor vessel is in the range of from about 0° C. to about 30° C.

Embodiment 67 is an alkylation process as set forth in one of embodiments 62-66, wherein the pressure in the reactor vessel is in the range of from about 2 to about 50 psig.

Embodiment 68 is an alkylation process as set forth in one of embodiments 62-67, wherein the contacting is performed in the reactor system as set forth in embodiment 1, and the process comprises: (a) mixing the olefin and/or the isoparaffin with the sulfuric acid catalyst in the mixer to generate an emulsion; (b) directing the emulsion to the distributor and injecting the emulsion into the reactor vessel through the distributor; and (c) recycling a portion of the emulsion through the emulsion pump.

Embodiment 69 is an alkylation process as set forth in embodiment 68, wherein another portion of the emulsion is sent to a sulfuric acid settler outside the reactor vessel.

Embodiment 70 is an alkylation process as set forth in embodiment 68, wherein the contacting is performed in the reactor system as set forth in embodiment 23, and the process further comprises: (d) passing the portion of the emulsion not recycled over the partition baffle and through the coalescing media into the acid settling zone; (e) separating a hydrocarbon phase from a sulfuric acid phase in the acid settling zone; (f) recycling at least a portion of the sulfuric acid phase to the mixer and the reaction zone; and (g) directing at least a portion of the hydrocarbon phase to a net effluent treatment section.

Embodiment 71 is an alkylation process as set forth in embodiment 68, wherein the contacting is performed in the reactor system as set forth in embodiment 26, and the process further comprises: (d) passing the portion of the emulsion not recycled over the first partition baffle and through the coalescing media into the acid settling zone; (e) separating a hydrocarbon phase from a sulfuric acid phase in the acid settling zone; (f) recycling at least a portion of the sulfuric acid phase to the mixer and the reaction zone; (g) passing the hydrocarbon phase over the second partition baffle moving from the acid settling zone into the effluent zone; and (h) directing at least a portion of the hydrocarbon phase to a net effluent treatment section.

Embodiment 72 is an alkylation process as set forth in one of embodiments 68-71, wherein the mixer is selected from the group consisting of an internal static mixer, an external static mixer, a homogenizer, and combinations thereof.

Embodiment 73 is an alkylation process as set forth in one of embodiments 68-72 further comprising partially flashing the emulsion injected into the reactor vessel to form vapor bubbles.

Embodiment 74 is an alkylation process as set forth in embodiment 73, wherein the reactor system further comprises a plurality of draft tubes extending upwardly from above the distributor, and at least a portion of the vapor bubbles rise through the draft tubes.

Embodiment 75 is an alkylation process as set forth in one of embodiments 62-67, wherein the contacting is performed in the split sulfuric acid alkylation reactor system as set forth in embodiment 33, and the process comprises: (a) mixing a first olefin and/or a first isoparaffin with a first sulfuric acid catalyst in the first mixer to generate a first emulsion; (b) directing the first emulsion to the first distributor and injecting the first emulsion into the first reaction zone through the first distributor; (c) recycling a portion of the first emulsion to the first reaction zone through the first emulsion pump; (d) passing the portion of the first emulsion not recycled over the first partition baffle and through the first coalescing media into the acid settling zone; (e) mixing a second olefin and/or a second isoparaffin with a second sulfuric acid catalyst in the second mixer to generate a second emulsion; (f) directing the second emulsion to the second distributor and injecting the second emulsion into the second reaction zone through the second distributor; (g) recycling a portion of the second emulsion to the second reaction zone through the second emulsion pump; (h) passing the portion of the second emulsion not recycled over the second partition baffle and through the second coalescing media into the acid settling zone; (i) separating a hydrocarbon phase from a sulfuric acid phase in the acid settling zone; (j) recycling a portion of the sulfuric acid phase to the first mixer and the first reaction zone; (k) recycling another portion of the sulfuric acid phase to the second mixer and the second reaction zone; and (l) directing at least a portion of the hydrocarbon phase to a net effluent treatment section.

Embodiment 76 is an alkylation process as set forth in embodiment 75, wherein the first mixer and the second mixer are independently selected from the group consisting of an internal static mixer, an external static mixer, a homogenizer, and combinations thereof.

Embodiment 77 is an alkylation process as set forth in embodiments 75 or 76 further comprising partially flashing the first emulsion and the second emulsion injected into the reactor vessel to form vapor bubbles.

Embodiment 78 is an alkylation process as set forth in embodiment 77, wherein the reactor system further comprises a plurality of first draft tubes extending upwardly from above the first distributor, and at least a portion of the vapor bubbles rise through the first draft tubes.

Embodiment 79 is an alkylation process as set forth in embodiment 77, wherein the reactor system further comprises a plurality of second draft tubes extending upwardly from above the second distributor, and at least a portion of the vapor bubbles rise through the second draft tubes.

Embodiment 80 is an alkylation process as set forth in one of embodiments 68-79, wherein a vapor comprising isoparaffin is generated in the reactor vessel, and said vapor exits the reactor vessel through the vapor outlet and is directed to a refrigeration section.

Embodiment 81 is an alkylation process as set forth in one of embodiments 62-80, wherein the olefin is a $C_3$ to $C_5$ olefin selected from the group consisting of propene, butenes, pentenes, and combinations thereof.

Embodiment 82 is an alkylation process as set forth in one of embodiments 62-81, wherein the isoparaffin comprises isobutane.

Embodiment 83 is a method for converting a hydrogen fluoride alkylation unit which utilizes hydrogen fluoride as a reaction catalyst to a sulfuric acid alkylation unit, the method comprising: (a) substituting sulfuric acid for hydrogen fluoride as the reaction catalyst; and (b) modifying a suitable vessel in the hydrogen fluoride alkylation unit to provide a sulfuric acid alkylation reactor system as set forth in one of embodiments 1-32 or a split sulfuric acid alkylation reactor system as set forth in one of embodiments 33-61, wherein the suitable vessel is retained as the reactor vessel in the sulfuric acid alkylation reactor systems.

Embodiment 84 is a method as set forth in embodiment 83 wherein the suitable vessel is selected from the group consisting of HF acid settlers and HF storage tanks.

Embodiment 85 is a method as set forth in embodiment 84 wherein the suitable vessel is a horizontal HF acid settler or an HF storage tank.

Embodiment 86 is a method as set forth in embodiment 85 further comprising: providing a refrigeration section comprising a compressor K/O drum, a refrigerant compressor and a refrigerant condenser for condensing a vapor stream from the refrigerant compressor.

Embodiment 87 is a method as set forth in embodiment 85 further comprising: retaining one or more fractionators in the fractionation section of the existing HF alkylation unit.

Embodiment 88 is a method as set forth in embodiment 84 wherein the suitable vessel is a vertical HF acid settler or an HF storage tank.

Embodiment 89 is a method as set forth in embodiment 88 further comprising: providing a refrigeration section comprising a compressor K/O drum, a refrigerant compressor and a refrigerant condenser for condensing a vapor stream from the refrigerant compressor.

Embodiment 90 is a method as set forth in embodiment 88 further comprising: retaining one or more fractionators in the fractionation section of the existing HF alkylation unit.

Embodiment 91 is a method for converting a hydrogen fluoride alkylation unit which utilizes hydrogen fluoride as a reaction catalyst to a sulfuric acid alkylation unit, the method comprising: (a) substituting sulfuric acid for hydrogen fluoride as the reaction catalyst; and (b) providing a sulfuric acid alkylation reactor system as set forth in one of embodiments 1-32 or a split sulfuric acid alkylation reactor system as set forth in one of embodiments 33-61, wherein a new vessel is provided as the reactor vessel in the sulfuric acid alkylation reactor systems.

Embodiment 92 is a converted sulfuric acid alkylation unit comprising a sulfuric acid alkylation reactor system as set forth in one of embodiments 1-32 or a split sulfuric acid alkylation reactor system as set forth in one of embodiments 33-61.

Embodiment 93 is a converted sulfuric acid alkylation unit as set forth in embodiment 92 comprising two or more alkylation reactor systems disposed in sequence, wherein the spent acid solution from at least one non-final alkylation reactor system is sent to the immediately subsequent alkylation reactor system as part or all of the sulfuric acid solution therein.

Embodiment 94 is a converted sulfuric acid alkylation unit as set forth in embodiment 93 wherein the spent acid solution from each non-final alkylation reactor system is sent to the immediately subsequent alkylation reactor system as part or all of the sulfuric acid solution therein.

Embodiment 95 is an alkylation process performed in a converted sulfuric acid alkylation unit as set forth in one of embodiments 92-94.

What is claimed is:

1. A sulfuric acid alkylation reactor system comprising:
   (a) a closed reactor vessel comprising a shell, a vapor outlet, and an emulsion outlet;
   (b) a distributor located at the lower portion of the reactor vessel;
   (c) a mixer fluidly connected with the distributor; and
   (d) an emulsion pump fluidly connected with the mixer and the emulsion outlet;
   wherein the emulsion pump is located outside the reactor vessel.

2. The sulfuric acid alkylation reactor system of claim 1, wherein the mixer is an internal static mixer located at the lower portion of the reactor vessel, the distributor is downstream of the internal static mixer and is directly connected with the internal static mixer.

3. The sulfuric acid alkylation reactor system of claim 2 further comprising an external static mixer fluidly connected with the internal static mixer and the emulsion pump, wherein the external static mixer is located outside the reactor vessel.

4. The sulfuric acid alkylation reactor system of claim 1, wherein the mixer is an in-line rotor stator mixer fluidly connected with the distributor, and the in-line rotor stator mixer is located outside the reactor vessel and is upstream of the distributor.

5. The sulfuric acid alkylation reactor system of claim 4 further comprising an external static mixer fluidly connected with the in-line rotor stator mixer and the emulsion pump, wherein the external static mixer is located outside the reactor vessel.

6. The sulfuric acid alkylation reactor system of claim 1, wherein the reactor vessel further comprises a second emulsion outlet fluidly connected with a sulfuric acid settler outside the reactor vessel.

7. The sulfuric acid alkylation reactor system of claim 1, wherein the reactor vessel further comprises a partition baffle, a coalescing media, a spent acid outlet, and a net effluent outlet; the partition baffle and the coalescing media extend upwardly from the bottom of the reactor vessel respectively, the coalescing media is downstream of the partition baffle and defines a reaction zone and an acid settling zone inside the reactor vessel, the reaction zone is upstream of the coalescing media, the acid settling zone is downstream of the coalescing media, the emulsion pump is also fluidly connected with the spent acid outlet, and the distributor is located at the reaction zone.

8. The sulfuric acid alkylation reactor system of claim 7, wherein the reactor vessel further comprises a second partition baffle extending upwardly from the bottom of the reactor vessel, the second partition baffle is downstream of the coalescing media and defines an effluent zone downstream of the second partition baffle.

9. The sulfuric acid alkylation reactor system of claim 1, wherein the reactor system further comprises a plurality of draft tubes extending upwardly from above the distributor.

10. A split sulfuric acid alkylation reactor system comprising:
    (a) a closed horizontal reactor vessel comprising a shell, a vapor outlet, a first emulsion outlet, a second emulsion outlet, a first partition baffle, a first coalescing media, a second partition baffle, a second coalescing media, a spent acid outlet, and a net effluent outlet;
    (b) a first distributor located at the lower portion of the reactor vessel;
    (c) a second distributor located at the lower portion of the reactor vessel;
    (d) a first mixer fluidly connected with the first distributor;
    (e) a second mixer fluidly connected with the second distributor;
    (f) a first emulsion pump fluidly connected with the first mixer, the first emulsion outlet, and the spent acid outlet; and
    (g) a second emulsion pump fluidly connected with the second mixer, the second emulsion outlet, and the spent acid outlet;
    wherein the first partition baffle, the second partition baffle, the first coalescing media, and the second coalescing media extend upwardly from the bottom of the reactor vessel respectively, the first coalescing media is downstream of the first partition baffle, the second coalescing media is downstream of the second partition baffle, the first coalescing media and the second coalescing media define a first reaction zone, a second reaction zone and an acid settling zone inside the reactor vessel, the first reaction zone is upstream of the first coalescing media, the second reaction zone is upstream of the second coalescing media, the acid settling zone is between the first coalescing media and the second coalescing media, the first distributor is located at the first reaction zone, the second distributor is located at the second reaction zone, the first emulsion pump and the second emulsion pump are located outside the reactor vessel.

11. The split sulfuric acid alkylation reactor system of claim 10, wherein the first mixer is a first internal static mixer located at the lower portion of the first reaction zone, the first distributor is downstream of the first internal static mixer and is directly connected with the first internal static mixer, the second mixer is a second internal static mixer located at the lower portion of the second reaction zone, the second distributor is downstream of the second internal static mixer and is directly connected with the second internal static mixer.

12. The split sulfuric acid alkylation reactor system of claim 11 further comprising a first external static mixer fluidly connected with the first internal static mixer and the first emulsion pump, and a second external static mixer fluidly connected with the second internal static mixer and the second emulsion pump, wherein both the first external static mixer and the second external static mixer are located outside the reactor vessel.

13. The split sulfuric acid alkylation reactor system of claim 10, wherein the first mixer is a first in-line rotor stator mixer fluidly connected with the first distributor, the second mixer is a second in-line rotor stator mixer fluidly connected with the second distributor, the first in-line rotor stator mixer is located outside the reactor vessel and is upstream of the first distributor, and the second in-line rotor stator mixer is located outside the reactor vessel and is upstream of the second distributor.

14. The split sulfuric acid alkylation reactor system of claim 13 further comprising a first external static mixer fluidly connected with the first in-line rotor stator mixer and the first emulsion pump, and a second external static mixer fluidly connected with the second in-line rotor stator mixer and the second emulsion pump, wherein both the first external static mixer and the second external static mixer are located outside the reactor vessel.

15. The split sulfuric acid alkylation reactor system of claim 10, wherein the reactor system further comprises a plurality of first draft tubes extending upwardly from above the first distributor, and a plurality of second draft tubes extending upwardly from above the second distributor.

16. The split sulfuric acid alkylation reactor system of claim 10, wherein the reactor system further comprises a raised sump having an open top and an outlet, the raised sump is inside the reactor vessel, and the outlet either is the net effluent outlet or is directly connected with the net effluent outlet.

17. An alkylation process comprising contacting an olefin with an isoparaffin in the presence of a sulfuric acid catalyst to produce a product mixture comprising an alkylate wherein the contacting is performed in the reactor system of claim 1 or claim 10.

18. A method for converting a hydrogen fluoride alkylation unit which utilizes hydrogen fluoride as a reaction catalyst to a sulfuric acid alkylation unit, the method comprising:
(a) substituting sulfuric acid for hydrogen fluoride as the reaction catalyst; and
(b) modifying a suitable vessel in the hydrogen fluoride alkylation unit to provide a sulfuric acid alkylation reactor system as set forth in claim 1 or a split sulfuric acid alkylation reactor system as set forth in claim 10, wherein the suitable vessel is retained as the reactor vessel in the sulfuric acid alkylation reactor systems.

19. A method for converting a hydrogen fluoride alkylation unit which utilizes hydrogen fluoride as a reaction catalyst to a sulfuric acid alkylation unit, the method comprising:
(a) substituting sulfuric acid for hydrogen fluoride as the reaction catalyst; and
(b) providing a sulfuric acid alkylation reactor system as set forth in claim 1 or a split sulfuric acid alkylation reactor system as set forth in claim 10, wherein a new vessel is provided as the reactor vessel in the sulfuric acid alkylation reactor systems.

20. A converted sulfuric acid alkylation unit comprising a sulfuric acid alkylation reactor system as set forth in claim 1 or a split sulfuric acid alkylation reactor system as set forth in claim 10.

\* \* \* \* \*